(12) United States Patent
Zappacosta et al.

(10) Patent No.: US 10,925,750 B2
(45) Date of Patent: *Feb. 23, 2021

(54) STANDALONE INTERBODY IMPLANTS

(71) Applicant: GLOBUS MEDICAL, INC., Audubon, PA (US)

(72) Inventors: Jason Zappacosta, Philadelphia, PA (US); Michael Hunt, Austin, TX (US); Veronika Martynova, Aston, PA (US); Jason Gray, East Greenville, PA (US); Jody Seifert, Birdsboro, PA (US); Noah Hansell, King of Prussia, PA (US); David Paul, Phoenixville, PA (US); Nick Padovani, Wynnewood, PA (US)

(73) Assignee: Globus Medical Inc., Audubon, PA (US)

( * ) Notice: Subject to any disclaimer, the term of this patent is extended or adjusted under 35 U.S.C. 154(b) by 10 days.

This patent is subject to a terminal disclaimer.

(21) Appl. No.: 16/205,892

(22) Filed: Nov. 30, 2018

(65) Prior Publication Data

US 2019/0105175 A1    Apr. 11, 2019

Related U.S. Application Data

(60) Continuation of application No. 15/954,655, filed on Apr. 17, 2018, now Pat. No. 10,179,053, which is a (Continued)

(51) Int. Cl.
*A61F 2/44*    (2006.01)

(52) U.S. Cl.
CPC ............ *A61F 2/4455* (2013.01); *A61F 2/442* (2013.01); *A61F 2/447* (2013.01)

(58) Field of Classification Search
CPC .......... A61F 2/44; A61F 2/442; A61F 2/4455; A61F 2/446; A61F 2/4465; A61F 2/447
See application file for complete search history.

(56) References Cited

U.S. PATENT DOCUMENTS

| 1,673,630 A | 6/1928 | Madge |
| 4,349,921 A | 9/1982 | Kuntz |

(Continued)

FOREIGN PATENT DOCUMENTS

| FR | 2727003 A1 | 5/1996 |
| JP | 2011502708 A | 1/2011 |

(Continued)

OTHER PUBLICATIONS

Guidance Document: Intervertebral Body Fusion Device, U.S. Dept. of Health and Human Services, Food and Drug Administration (Jun. 12, 2007).

(Continued)

*Primary Examiner* — Eric S Gibson

(57) ABSTRACT

Stand-alone interbody fusion devices for engagement between adjacent vertebrae. The stand-alone interbody fusion devices may include a spacer or endplates and one or more inserts, members, or frames coupled to the spacer or endplates. The inserts, members, or frames may be configured and designed to provide the apertures which are designed to retain bone fasteners, such as screws or anchors, and secure the implant to the adjacent vertebrae.

18 Claims, 42 Drawing Sheets

Related U.S. Application Data division of application No. 14/509,634, filed on Oct. 8, 2014, now Pat. No. 9,968,461, which is a continuation-in-part of application No. 14/278,898, filed on May 15, 2014, now Pat. No. 9,545,320.

(56) References Cited

U.S. PATENT DOCUMENTS

| | | |
|---|---|---|
| 4,599,086 A | 7/1986 | Doty |
| 4,743,256 A | 5/1988 | Brantigan |
| 4,834,757 A | 5/1989 | Brantigan |
| 4,904,261 A | 2/1990 | Dove et al. |
| 4,917,704 A | 4/1990 | Frey |
| 4,955,908 A | 9/1990 | Frey |
| 5,002,576 A | 3/1991 | Fuhrmann et al. |
| 5,364,399 A | 11/1994 | Lowery et al. |
| 5,397,364 A | 3/1995 | Kozak et al. |
| 5,458,641 A | 10/1995 | Jimenez |
| 5,514,180 A | 5/1996 | Heggeness |
| 5,549,612 A | 8/1996 | Yapp et al. |
| 5,645,596 A | 7/1997 | Kim et al. |
| 5,861,041 A | 1/1999 | Tienboon |
| 5,888,223 A | 3/1999 | Bray, Jr. |
| 6,045,579 A | 4/2000 | Hochshuler |
| 6,066,175 A | 5/2000 | Henderson et al. |
| 6,146,421 A | 11/2000 | Gordon |
| 6,156,037 A | 12/2000 | LeHuec et al. |
| 6,200,347 B1 | 3/2001 | Anderson et al. |
| 6,206,922 B1 | 3/2001 | Zdeblick et al. |
| 6,231,610 B1 | 5/2001 | Geisler |
| 6,235,033 B1 | 5/2001 | Brace et al. |
| 6,235,059 B1 | 5/2001 | Benezech |
| 6,258,089 B1 | 7/2001 | Campbell et al. |
| 6,342,074 B1 | 1/2002 | Simpson |
| 6,364,880 B1 | 4/2002 | Michelson |
| 6,383,186 B1 | 5/2002 | Michelson |
| 6,425,920 B1 | 7/2002 | Hamada |
| 6,432,106 B1 | 8/2002 | Fraser |
| 6,468,311 B2 * | 10/2002 | Boyd .................. A61F 2/28 623/17.11 |
| 6,471,724 B2 | 10/2002 | Zdeblick |
| 6,482,233 B1 | 11/2002 | Aebi |
| 6,520,993 B2 | 2/2003 | James |
| 6,540,785 B1 | 4/2003 | Gill et al. |
| 6,558,387 B2 | 5/2003 | Errico |
| 6,558,423 B1 | 5/2003 | Michelson |
| 6,558,424 B2 | 5/2003 | Thalgott |
| 6,562,073 B2 | 5/2003 | Foley |
| 6,629,998 B1 | 10/2003 | Lin |
| 6,666,889 B1 | 12/2003 | Commarmond |
| 6,682,563 B2 | 1/2004 | Scharf |
| 6,709,458 B2 | 3/2004 | Michelson |
| 6,730,127 B2 | 5/2004 | Michelson |
| 6,740,118 B2 | 5/2004 | Eisermann et al. |
| 6,793,658 B2 | 9/2004 | Lehuec |
| 6,805,714 B2 | 10/2004 | Sutcliffe |
| 6,827,740 B1 | 12/2004 | Michelson |
| 6,835,206 B2 | 12/2004 | Jackson |
| 6,849,093 B2 | 2/2005 | Michelson |
| 6,887,272 B2 | 5/2005 | Shinomiya |
| 6,899,735 B2 | 5/2005 | Coates et al. |
| 6,972,019 B2 | 12/2005 | Michelson |
| 7,001,432 B2 | 2/2006 | Keller et al. |
| 7,025,787 B2 | 4/2006 | Bryan et al. |
| 7,044,972 B2 | 5/2006 | Mathys, Jr. |
| 7,137,997 B2 | 11/2006 | Paul |
| 7,147,665 B1 | 12/2006 | Bryan et al. |
| 7,153,325 B2 | 12/2006 | Kim et al. |
| 7,163,561 B2 | 1/2007 | Michelson |
| 7,172,627 B2 | 2/2007 | Fiere et al. |
| 7,192,447 B2 | 3/2007 | Rhoda |
| 7,232,464 B2 | 6/2007 | Mathieu et al. |
| 7,238,203 B2 | 7/2007 | Bagga et al. |
| 7,276,082 B2 | 10/2007 | Zdeblick et al. |
| 7,309,357 B2 | 12/2007 | Kim |
| 7,320,708 B1 | 1/2008 | Bernstein |
| 7,594,931 B2 | 9/2009 | Louis et al. |
| 7,618,456 B2 | 11/2009 | Mathieu et al. |
| 7,771,475 B2 | 8/2010 | Michelson |
| 7,794,502 B2 | 9/2010 | Michelson |
| 7,846,207 B2 | 12/2010 | Lechmann et al. |
| 7,850,731 B2 | 12/2010 | Brittain |
| 7,862,616 B2 | 1/2011 | Lechmann et al. |
| 7,875,076 B2 | 1/2011 | Mathieu et al. |
| 7,972,381 B2 | 7/2011 | Michelson |
| 8,100,976 B2 | 1/2012 | Bray et al. |
| 8,105,383 B2 | 1/2012 | Michelson |
| 8,114,162 B1 | 2/2012 | Bradley |
| 8,137,403 B2 | 3/2012 | Michelson |
| 8,137,405 B2 | 3/2012 | Kostuik et al. |
| 8,216,312 B2 | 7/2012 | Gray |
| 8,268,000 B2 | 9/2012 | Waugh et al. |
| 8,273,127 B2 * | 9/2012 | Jones .................. A61F 2/4465 623/17.16 |
| 8,323,343 B2 | 12/2012 | Michelson |
| 8,328,872 B2 | 12/2012 | Duffield et al. |
| 8,343,222 B2 | 1/2013 | Cope |
| 8,425,607 B2 | 4/2013 | Waugh et al. |
| 8,439,977 B2 | 5/2013 | Kostuik et al. |
| 8,486,149 B2 * | 7/2013 | Saidha ................. A61F 2/4455 623/17.16 |
| 8,540,774 B2 | 9/2013 | Kueenzi et al. |
| 9,149,365 B2 * | 10/2015 | Lawson ............... A61F 2/4455 |
| 9,237,957 B2 * | 1/2016 | Klimek ................. A61F 2/447 |
| 9,277,946 B2 * | 3/2016 | Hooper ................. A61F 2/447 |
| 9,364,340 B2 * | 6/2016 | Lawson ............... A61F 2/4455 |
| 9,402,738 B2 * | 8/2016 | Niemiec ............... A61F 2/447 |
| 9,486,327 B2 * | 11/2016 | Martynova ........... A61F 2/447 |
| 9,526,630 B2 * | 12/2016 | Klimek ............. A61B 17/8042 |
| 9,585,765 B2 * | 3/2017 | Niemiec ........... A61B 17/7097 |
| 10,179,053 B2 * | 1/2019 | Zappacosta .......... A61F 2/4455 |
| 2001/0005796 A1 | 6/2001 | Zdeblick |
| 2001/0034553 A1 | 10/2001 | Michelson |
| 2002/0004683 A1 | 1/2002 | Michelson |
| 2002/0010511 A1 | 1/2002 | Michelson |
| 2002/0016595 A1 | 2/2002 | Michelson |
| 2002/0082597 A1 | 6/2002 | Fraser |
| 2002/0138146 A1 | 9/2002 | Jackson |
| 2002/0143399 A1 | 10/2002 | Sutcliffe |
| 2002/0147450 A1 | 10/2002 | Lehuec |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2003/0181981 A1 | 9/2003 | Lemaire |
| 2004/0078078 A1 | 4/2004 | Shepard |
| 2004/0082998 A1 | 4/2004 | Shinomiya |
| 2004/0082999 A1 | 4/2004 | Robert, Jr. |
| 2004/0117018 A1 | 6/2004 | Michelson |
| 2004/0143270 A1 | 7/2004 | Zucherman et al. |
| 2004/0143332 A1 | 7/2004 | Krueger et al. |
| 2004/0176853 A1 | 9/2004 | Sennett et al. |
| 2004/0199253 A1 * | 10/2004 | Link ................... A61F 2/4425 623/17.11 |
| 2005/0055098 A1 | 3/2005 | Zdeblick et al. |
| 2005/0065607 A1 | 3/2005 | Gross |
| 2005/0149192 A1 | 7/2005 | Zuchermann et al. |
| 2005/0149193 A1 | 7/2005 | Zuchermann et al. |
| 2005/0159819 A1 | 7/2005 | McCormack et al. |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2006/0085071 A1 | 4/2006 | Lechmann et al. |
| 2006/0116767 A1 | 6/2006 | Magerl et al. |
| 2006/0129240 A1 | 6/2006 | Lessar et al. |
| 2006/0217809 A1 | 9/2006 | Albert et al. |
| 2007/0088441 A1 | 4/2007 | Duggal et al. |
| 2007/0106388 A1 | 5/2007 | Michelson |
| 2007/0123987 A1 | 5/2007 | Bernstein |
| 2007/0135923 A1 | 6/2007 | Peterman et al. |
| 2007/0162130 A1 | 7/2007 | Rashbaum et al. |

(56) References Cited

U.S. PATENT DOCUMENTS

| | | |
|---|---|---|
| 2007/0168032 A1 | 7/2007 | Muhanna et al. |
| 2007/0225806 A1 | 9/2007 | Squires et al. |
| 2007/0225810 A1 | 9/2007 | Colleran et al. |
| 2007/0225812 A1 | 9/2007 | Gill |
| 2007/0233253 A1 | 10/2007 | Bray et al. |
| 2007/0250167 A1 | 10/2007 | Bray et al. |
| 2007/0270961 A1 | 11/2007 | Ferguson |
| 2008/0046083 A1 | 2/2008 | Hewko |
| 2008/0051890 A1 | 2/2008 | Waugh et al. |
| 2008/0051907 A1 | 2/2008 | Marik |
| 2008/0133013 A1 | 6/2008 | Duggal et al. |
| 2008/0281425 A1* | 11/2008 | Thalgott ............. A61F 2/447 623/17.16 |
| 2008/0306596 A1* | 12/2008 | Jones ............. A61B 17/8042 623/17.16 |
| 2009/0076608 A1 | 3/2009 | Gordon et al. |
| 2009/0210062 A1 | 8/2009 | Thalgott et al. |
| 2010/0057206 A1* | 3/2010 | Duffield ............. A61F 2/4465 623/17.16 |
| 2010/0145460 A1 | 6/2010 | Mcdonough |
| 2010/0312345 A1* | 12/2010 | Duffield ............. A61F 2/4465 623/17.16 |
| 2010/0312346 A1* | 12/2010 | Kueenzi ............. A61F 2/44 623/17.16 |
| 2011/0087327 A1 | 4/2011 | Lechmann |
| 2011/0166658 A1 | 7/2011 | Garber et al. |
| 2011/0251689 A1 | 10/2011 | Seifert |
| 2012/0078371 A1 | 3/2012 | Gamache et al. |
| 2012/0078373 A1 | 3/2012 | Gamache et al. |
| 2012/0179259 A1* | 7/2012 | McDonough ............. A61F 2/4455 623/17.16 |
| 2012/0245690 A1 | 9/2012 | Cowan, Jr. et al. |
| 2013/0110247 A1 | 5/2013 | Doran et al. |
| 2014/0012380 A1 | 1/2014 | Laurence et al. |
| 2014/0039623 A1* | 2/2014 | Iott ............. A61F 2/4455 623/17.16 |
| 2014/0180422 A1* | 6/2014 | Klimek ............. A61F 2/30744 623/17.16 |
| 2014/0228957 A1* | 8/2014 | Niemiec ............. A61B 17/8605 623/17.16 |
| 2014/0228958 A1* | 8/2014 | Niemiec ............. A61F 2/30767 623/17.16 |
| 2014/0228959 A1* | 8/2014 | Niemiec ............. A61F 2/4455 623/17.16 |
| 2014/0243981 A1* | 8/2014 | Davenport ............. A61F 2/4455 623/17.16 |
| 2014/0257487 A1* | 9/2014 | Lawson ............. A61B 17/8042 623/17.16 |
| 2014/0277487 A1* | 9/2014 | Davenport ............. A61F 2/447 623/17.16 |
| 2014/0277488 A1* | 9/2014 | Davenport ............. A61F 2/442 623/17.16 |
| 2014/0277489 A1* | 9/2014 | Davenport ............. A61F 2/447 623/17.16 |
| 2014/0277497 A1* | 9/2014 | Bennett ............. A61F 2/4465 623/17.16 |
| 2014/0309741 A1 | 10/2014 | Ganter et al. |
| 2015/0328009 A1* | 11/2015 | Zappacosta ............. A61F 2/4455 623/17.16 |
| 2015/0328010 A1* | 11/2015 | Martynova ............. A61F 2/442 623/17.16 |
| 2016/0089246 A1* | 3/2016 | Klimek ............. A61F 2/30744 623/17.16 |
| 2016/0095714 A1* | 4/2016 | Spangler ............. A61F 2/447 623/17.16 |
| 2017/0014241 A1* | 1/2017 | Martynova ............. A61F 2/447 |
| 2017/0049579 A1* | 2/2017 | Quinlan ............. A61F 2/447 |
| 2018/0235772 A1* | 8/2018 | Zappacosta ............. A61F 2/4455 |
| 2019/0105175 A1* | 4/2019 | Zappacosta ............. A61F 2/442 |

FOREIGN PATENT DOCUMENTS

| | | |
|---|---|---|
| JP | 2013-540503 A | 11/2013 |
| WO | 1997023175 A1 | 7/1997 |
| WO | 1999063914 A1 | 12/1999 |
| WO | 2005007040 A1 | 1/2005 |
| WO | 2007098288 A2 | 8/2007 |
| WO | 2008014258 A2 | 1/2008 |
| WO | 2012115631 A1 | 8/2012 |
| WO | 2014138311 A1 | 9/2014 |

OTHER PUBLICATIONS

M. Spruit et al., The in vitro stabilizing effect of polyetheretherketone cages versus a titanium cage of similar design for anterior lumbar interbody fusion, 14(8) Eur. Spine J. 752, 752-758 (2005).

P. Schleicher et al., Biomechanical comparison of two different concepts for stand alone anterior lumbar interbody fusion, 17(12) EUR. Spine J. 1757, 1757-1765 (2008).

P.W. Pavlov et al., Anterior lumbar interbody fusion with threaded fusion cages and autologous bone grafts, 9 Eur. Spine J. 224, 224-229 (2000).

Synthes' SynFix Technique Guide device ("SynFix Technique Guide").

* cited by examiner

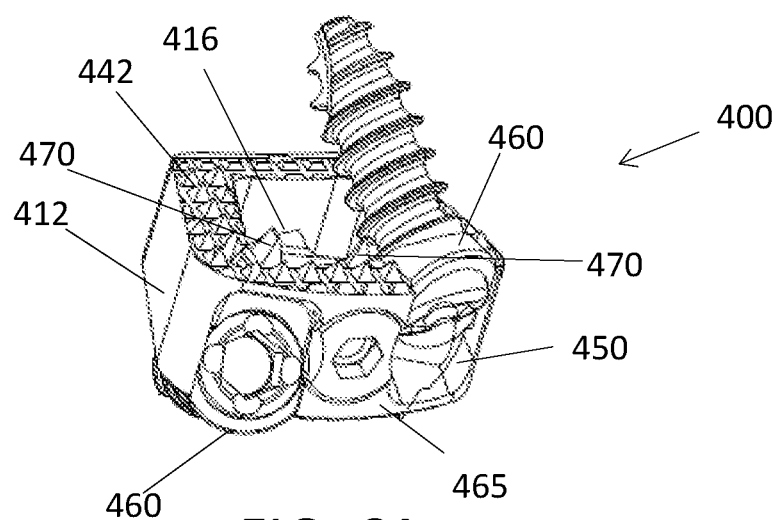
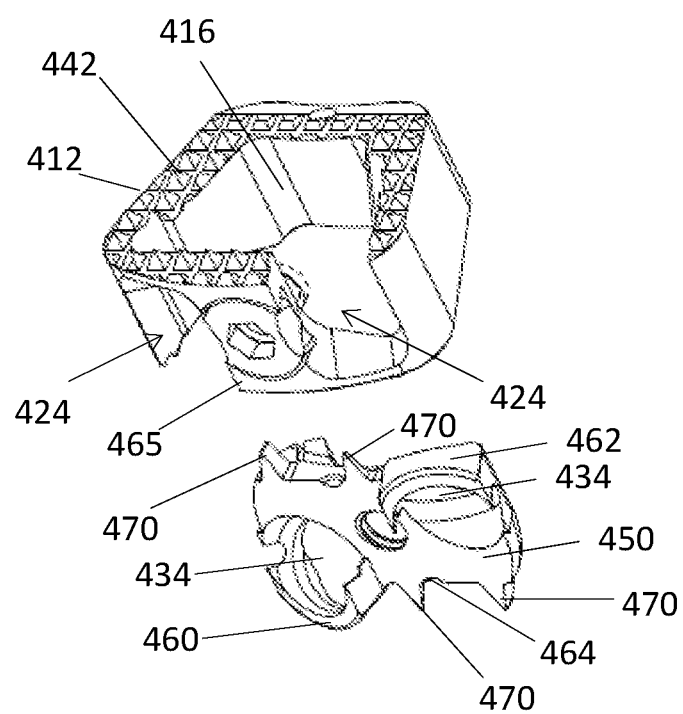
FIG. 6A
FIG. 6B

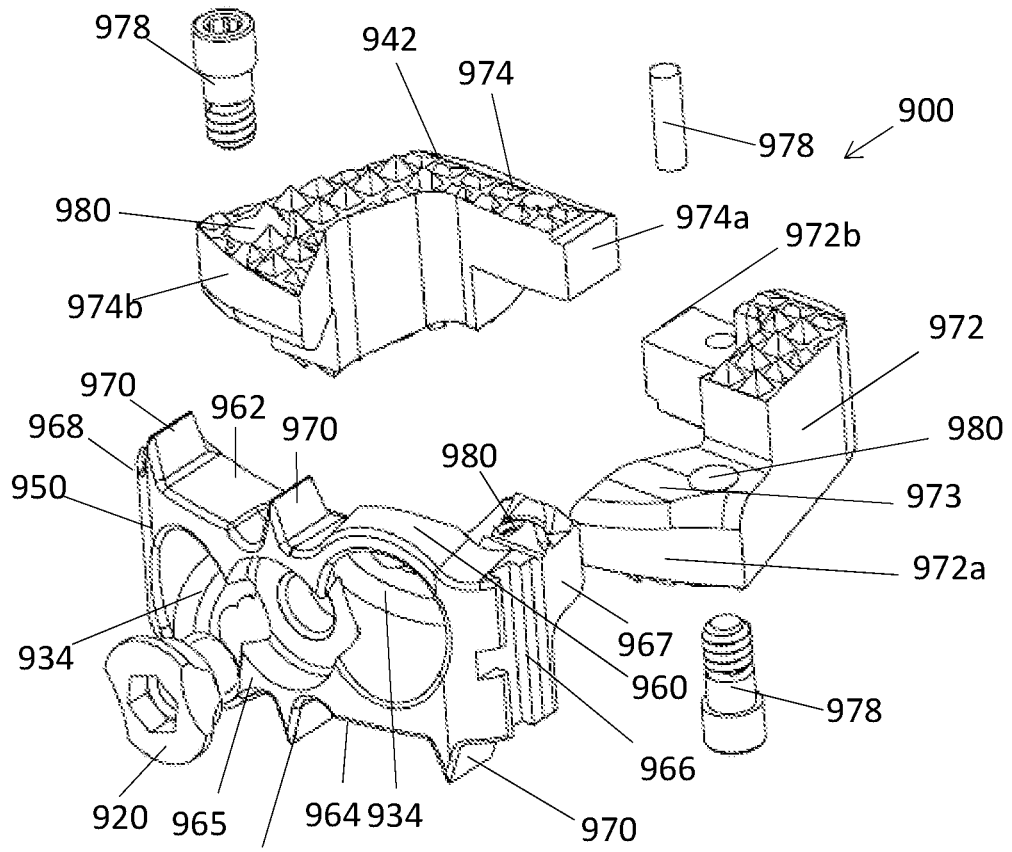
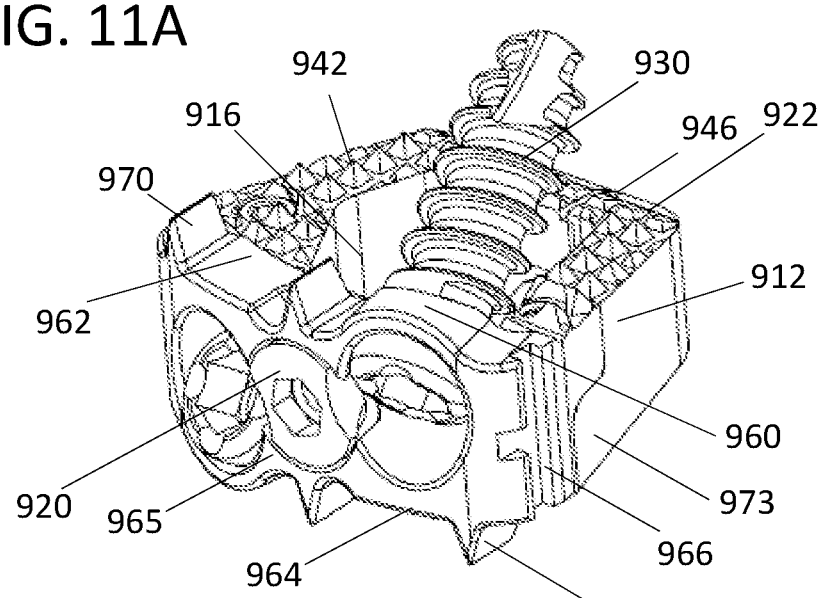
FIG. 11A
FIG. 11B

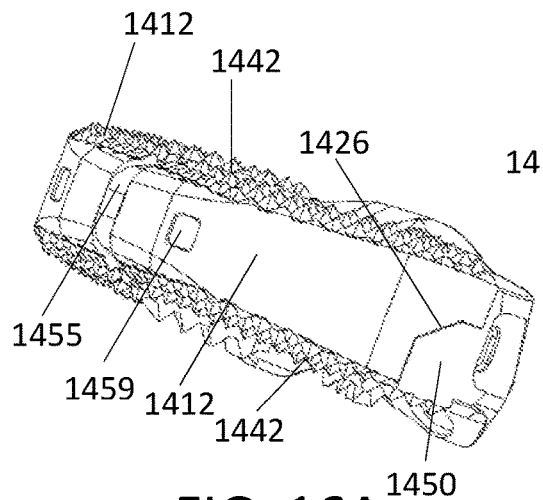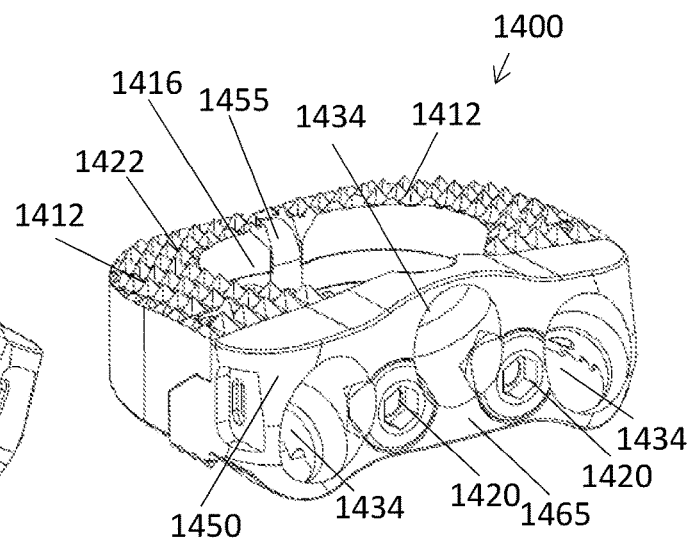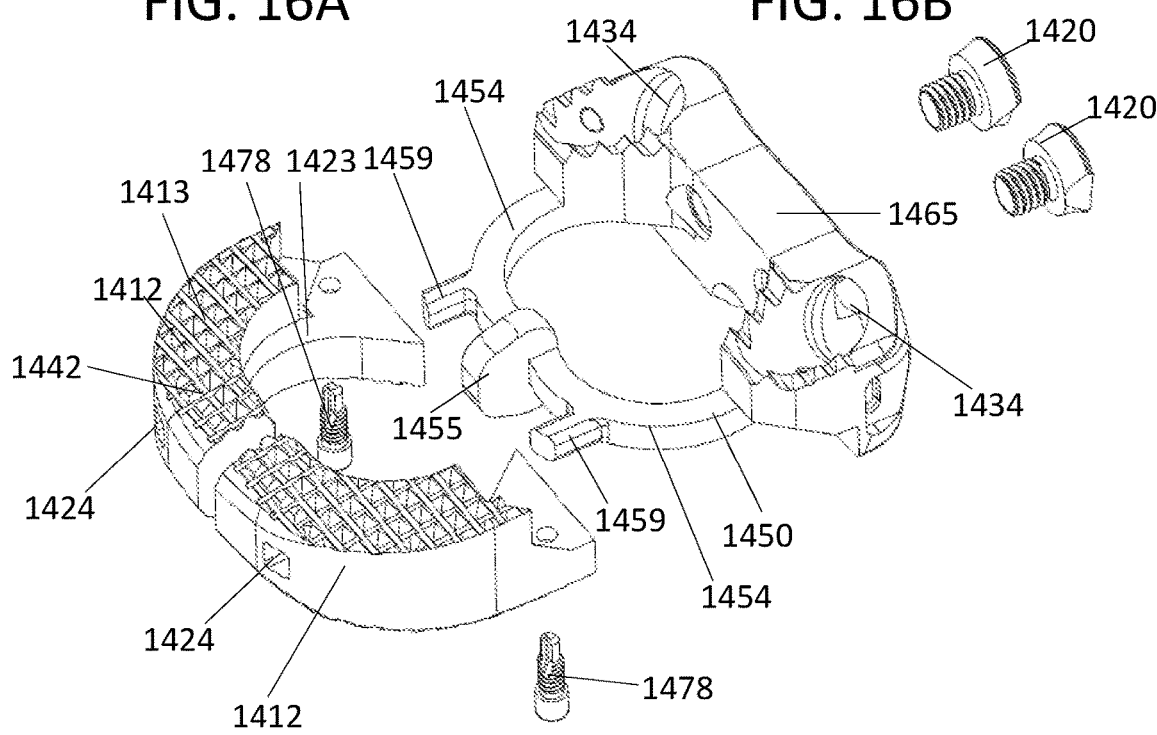

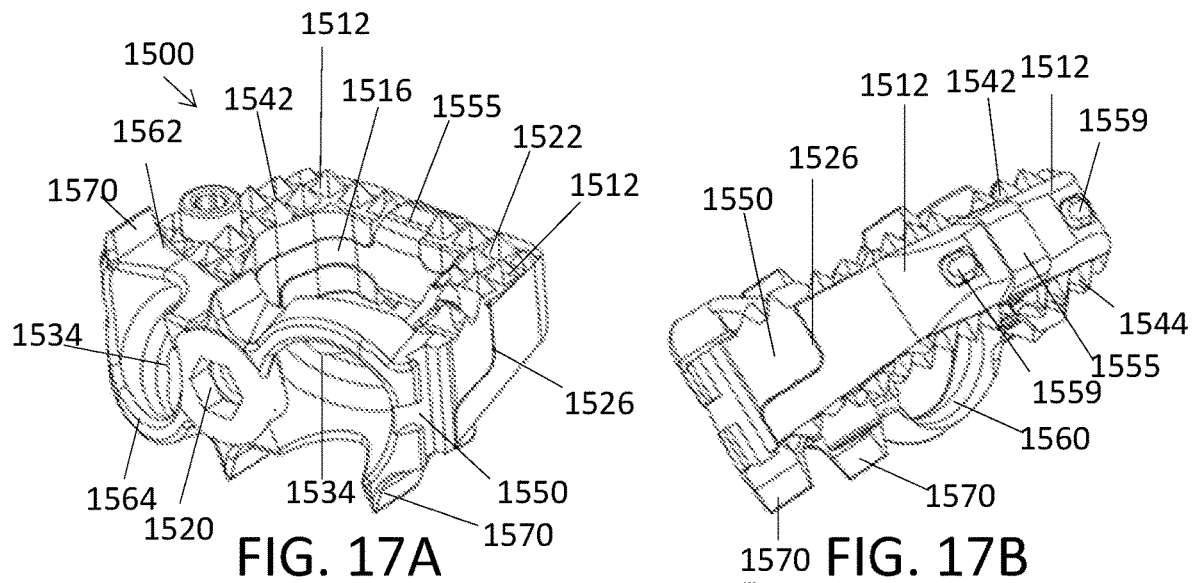
FIG. 17A
FIG. 17B
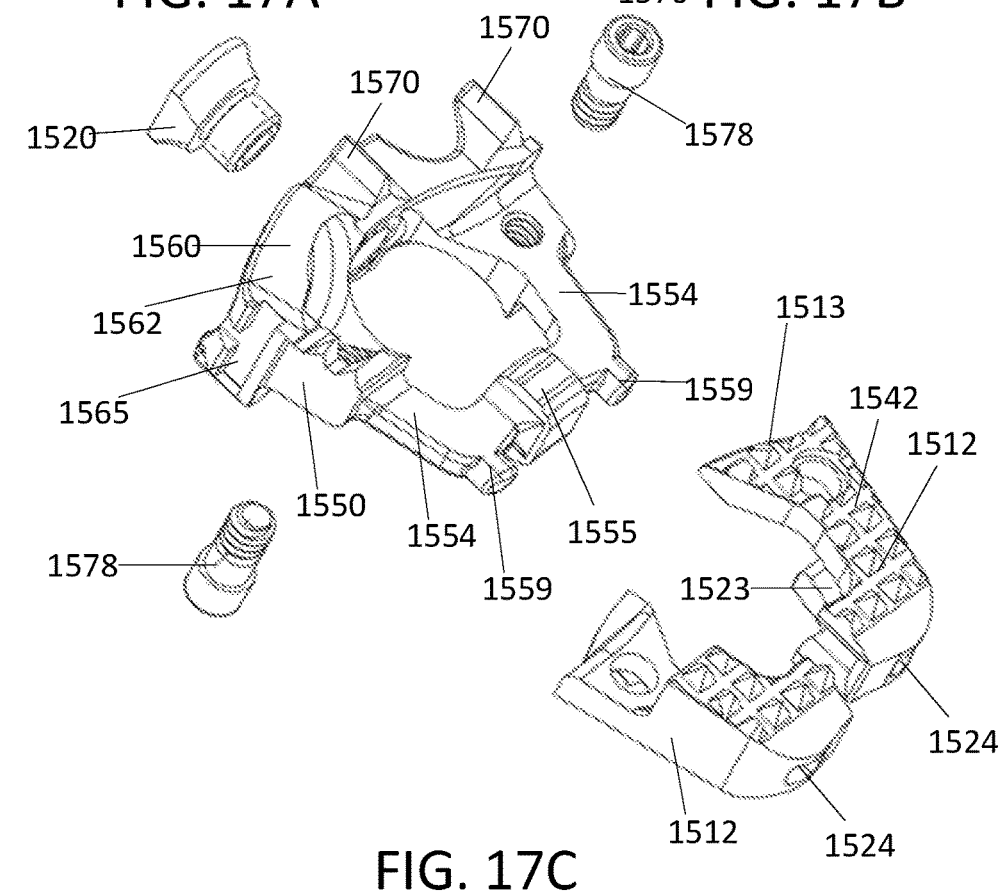
FIG. 17C

STANDALONE INTERBODY IMPLANTS

CROSS REFERENCE TO RELATED APPLICATION

The present application is continuation application of U.S. patent application Ser. No. 15/954,655 filed on Apr. 17, 2018 which is a divisional of U.S. patent application Ser. No. 14/509,634, filed Oct. 8, 2014, which is a continuation-in-part of U.S. patent application Ser. No. 14/278,898 filed on May 15, 2014, the entire disclosures of which are incorporated herein by reference in their entireties for all purposes.

FIELD OF THE INVENTION

The present disclosure generally relates to fixation devices for positioning and immobilizing adjacent vertebral bodies. In particular, the devices may include stand-alone interbody fusion devices.

BACKGROUND OF THE INVENTION

As people age, the intervertebral discs in the spinal column may start to deteriorate. Subsequently, the intervertebral discs being to lose height. As a result of the loss of height between vertebral bodies, the nerves exiting from the spinal canal become compressed and pinched, which causes pain among other neurological deficits. One solution is to insert a spacer in place of the disc to restore the height and to promote fusion between adjacent vertebral bodies to permanently maintain the height restoration. Additional fixation is also needed to stabilize the spinal segment. A plate is usually provided, and the plate may be positioned on the anterior portions of the adjacent vertebral bodies. In some cases, the profile of the plate becomes obstructive to the anatomy. The approach to the spine is also significant in that a direct anterior approach requires navigation or dissection of vascular anatomy.

As a result, there is a need to provide a spacer having fixation elements to attach the spacer directly to adjacent vertebrae, to limit any profile protruding out of the spine column anteriorly, and to avoid proximal anatomy from a direct anterior approach. The spacer alone, however, may not be strong enough to support fixation elements, such as screws, when the spacer is made solely from certain non-metallic materials, such as, polyether ether ketone (PEEK). Thus, there is also a need for frames or spacers at least partially constructed of strong materials or in such a manner so as to provide additional support for the fixation elements.

SUMMARY OF THE INVENTION

To meet this and other needs, stand-alone interbody fusion implants and devices are provided. The implants may be provided with a spacer and at least one insert or member. The implants may also be composed of a frame with one or more endplates affixed thereto. The inserts, members, or frames may be especially suited for defining apertures designed to secure fixation elements or fasteners, such as screws, staples, pins, nails, anchors, or the like, and the spacers to adjacent vertebrae. These implants provide for a spine stabilization system that promotes fusion of adjacent vertebrae while at the same time providing stabilization of the spinal area where fusion occurs.

According to one embodiment, an intervertebral implant for implantation in an intervertebral space between adjacent vertebrae includes a spacer and at least one insert. The spacer has a superior surface, an inferior surface, a proximal end, and a distal end. The superior surface and the inferior surface each have a contact area configured to engage adjacent vertebrae. The spacer defines an opening extending from the superior surface to the inferior surface of the spacer. The opening may be configured for receiving bone graft material to promote fusion of the adjacent vertebral bodies. The spacer defines one or more cutout extending from the proximal end to the opening. The spacer may also include a plurality of protrusions on the contact areas of the superior and inferior surfaces for engaging the adjacent vertebrae.

The insert at least partially defines a fastener aperture. These apertures may be in the form of through holes designed, sized, and dimensioned to accommodate and receive fixation devices or fasteners, such as bone screws or anchors. The insert is coupled to the spacer such that at least a portion of the insert is received in the cutout in the spacer.

The insert may be configured in such a way to enhance the strength and stability of the spacer. The insert may extend a distance beyond the superior surface, the inferior surface, or both surfaces of the spacer (e.g., a portion of the insert may extend above or below the superior and inferior surfaces of the spacer). For example, a front surface of the insert may include at least one eyebrow where the eyebrow projects past the superior surface, the inferior surface, or both surfaces of the spacer. The fastener aperture for receiving the fastener may traverse the front surface of the insert at an angle divergent to a horizontal plane in order to help secure the implant to one or both of the adjacent vertebrae.

Unlike a traditional plate, which is typically a thin, flat sheet or strip of material, the insert is provided with a given depth and dimension designed to integrate seamlessly with the spacer. In particular, the depth of the insert may be greater than the width and/or height of the insert. The insert may include a head portion and at least one arm projecting therefrom. The head portion may be enlarged to define the aperture configured for retaining the fastener. The arm may extend laterally, medially, and/or posteriorly away from the head portion. In particular, the arm may extend posteriorly and may be configured to mimic the shape and design of the spacer. The spacer may define at least one recess sized and dimensioned to retain at least a portion of the arm. For example, the arm may rest against a portion of the spacer or a recess therein to form a lap joint, half lap joint, stepped joint, or the like. Any type of joint formed between the insert and the spacer may be secured with one or more pins.

According to another embodiment, the insert may be provided in the shape of a ring, cylinder, c-shape, or the like. The ring or c-shaped insert may be provided with one or more slits, for example, to allow the insert to tightly mate with the cutout through the spacer and secure the insert to the spacer. In particular, one or more slits may be longitudinally positioned around a periphery of the ring or c-shaped insert.

According to another embodiment, the insert may be provided in the shape of a ring, cylinder, c-shape, or the like. The ring or c-shaped insert may be provided with one or more slits, for example, to allow the insert to tightly mate with the cutout through the spacer and secure the insert to the spacer. In particular, one or more slits may be longitudinally positioned around a periphery of the ring or c-shaped insert.

According to yet another embodiment, a stand-alone implant for implantation in a treated area of an intervertebral space between vertebral bodies of a spine includes a spacer and at least one member. The spacer has a first spacer portion and a second spacer portion, each of the first and second spacer portions having a first end and a second end. The second end of the first spacer portion is coupled to the first end of the second spacer portion. The first and second spacer portions form a superior surface and an inferior surface, and the superior surface and the inferior surface each have a contact area configured to engage adjacent vertebrae.

The member has an upper surface, a lower surface, a first lateral portion, a second lateral portion, and at least one hole traversing the member for receiving a fastener. The member is coupled to the spacer such that the first end of the first spacer portion engages the first lateral portion of the member and the second end of the second spacer portion engages the second lateral portion of the member.

The first and second spacer portions may be joined together in any suitable manner. For example, the first and second spacer portions may be mated together by a splice joint, scarf joint, butt joint, or the like. In the alternative or in addition, the first and second spacer portions may be secured together with one or more connectors. For example, the connector may include at least first and second tenons sized and configured to be received within a first mortise in the second end of the first spacer portion and a second mortise in the first end of the second spacer portion. Any type of joint formed between the first and second spacer portions may be further secured with one or more pins or the like.

The spacer portions and the member may also be joined together in any suitable manner. Similar to the insert configuration, the member may rest against a portion of the spacer portions or a recess therein to form a lap joint, half lap joint, stepped joint, or the like. For example, the member may include a first extension extending from the first lateral portion and a second extension extending from the second lateral portion. The first extension may contact a first ledge on the first spacer portion to form a first half lap joint, and the second extension may contact a second ledge on the second spacer portion to form a second half lap joint. If desired, the first and second half lap joints may each be further secured with at least one pin.

According to a further embodiment, an implant for implantation in an intervertebral space between adjacent vertebrae includes a spacer and an anterior portion. The spacer has a superior surface, an inferior surface, a proximal end, and a distal end, for example, configured for insertion into the intervertebral space. The superior surface and the inferior surface each have a contact area configured to engage adjacent vertebrae. The spacer defines an opening extending from the superior surface to the inferior surface of the spacer.

The anterior portion extends from the proximal end of the spacer such that the anterior portion and the spacer are a single piece. The anterior portion has an upper surface, a lower surface, a first lateral portion, a second lateral portion, and at least one hole traversing the anterior portion for receiving a fastener. At least a portion of the upper surface or the lower surface of the anterior portion extends beyond the superior surface or the inferior surface of the spacer. For example, at least one beam may connect the anterior portion to the proximal end of the spacer to form a unitary piece.

The distal end of the spacer may have a first spring feature configured to allow for compression and expansion of the spacer. For example, the first spring feature may be in the form of a v-spring. In addition, the proximal end of the spacer may include a second spring feature. The second spring feature may also be in the form of a v-spring. In particular, the second spring feature may include more than one v-spring oriented in opposite directions. The first and second spring features may be configured such that the spacer simulates the modulus of elasticity of bone even when the spacer and the anterior portion are comprised of titanium.

According to another embodiment, an intervertebral implant for implantation in an intervertebral space between adjacent vertebrae may include a frame and at least one endplate. The frame may include a front portion and a plurality of arms extending from the front portion and joined together to form a ring-like structure, for example, with a central opening. The front portion may at least partially define an opening or fastener aperture sized and dimensioned for receiving a fastener. The endplate or endplates include at least one outer surface having a contact area configured to engage adjacent vertebrae. The endplate is affixed to the frame such that the endplate contacts at least a portion of the arms of the frame. The implant may be secured to adjacent vertebrae using one or more fasteners, such as an anchor and/or a bone screw.

According to yet another embodiment, a stand-alone implant for implantation in a treated area of an intervertebral space between vertebral bodies of a spine may include a frame and at least one endplate secured to the frame. The frame may include a front portion having a first end and a second end, a first arm extending orthogonally from the first end of the front portion, and a second arm extending orthogonally from the second end of the front portion. The first and second arms join together at a rear portion to form a continuous ring-like body. One or more holes traverse the front portion for receiving a fastener. The endplates are secured to the frame such that the endplate rests on at least one of the first and second arms, the endplate forming a superior surface, an inferior surface, or both surfaces to form a contact area configured to engage adjacent vertebrae. The implant may define a central opening extending from the superior surface to the inferior surface of the implant configured to receive bone graft material.

The frame and endplates may include one or more of the following features. The front portion of the frame may have a first height and the plurality of arms may have a second height that is less than the first height in order to accommodate the height of the endplates without increasing the overall height of the implant. The frame may include a raised rear portion such that a plurality of endplates are configured to be separated a lateral distance from one another due to the raised rear portion on the frame. The raised rear portion may be substantially flush with the outer surface of the endplate or may be recessed a distance below the outer surface of the endplates. The endplates may be configured to be separated a vertical distance due to a thickness of the arms. The endplates may define at least one channel extending along an inner perimeter sized and configured to receive at least a portion of the arms of the frame. The frame may include at least one projection extending along a length of the arms and the endplate may define at least one recess sized and configured to receive the at least one projection. The frame may include at least one post extending outwardly from the arms and the endplate may include at least one opening sized and configured to receive the at least one post. The endplates may extend from an upper surface to a lower surface and completely surround at least one of the arms. The front portion of the frame may include a front surface and at least one eyebrow, wherein the eyebrow projects past the superior surface, the inferior surface, or both surfaces of the endplate, and the fastener aperture for receiving the fastener traverses the front surface of the frame at an angle divergent to a horizontal plane. The endplates preferably do not cover the front portion of the frame.

In any of the embodiments described herein, the implant may also include a locking mechanism, for example, disposed on the spacer, insert, member, or frame for preventing back out of the screws. For example, a cam-style blocking mechanism may be used with screws that capture the fixation device screws once they are inserted fully into the implant.

The implants may be formed from any suitable biocompatible materials. For example, the implant may be manufactured from a biocompatible metal, such as titanium, polyether ether ketone (PEEK), bone or the like. In one embodiment, the spacer or endplates is formed of a first material and the insert, member, or frame is formed of a second material different from the first material. The insert, member, or frame may be made of a stronger material designed to strength and reinforce one or more openings in the spacer (e.g., designed to retain bone screws) or as attached to the endplates. For example, the spacer or endplates may be formed from PEEK and the insert, member, and frame may be formed from titanium. In the embodiment where the anterior portion and the spacer form a single piece, titanium may be selected for the entire implant because the one or more spring features provide for the spacer to emulate the elasticity of bone.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 6A is a perspective view of a sixth embodiment including a single insert recessed behind the front portion of the spacer;

FIG. 6B shows an exploded view of the embodiment shown in FIG. 6A;

FIG. 11A shows an exploded view of an eleventh embodiment including a two-part spacer and a member;

FIG. 11B shows a perspective view of the embodiment shown in FIG. 11A;

FIG. 16A is a perspective side view of a sixteenth embodiment with an alternative frame;

FIG. 16B is a perspective front view of the embodiment shown in FIG. 16A;

FIG. 16C is an exploded view of the embodiment shown in FIG. 16B;

FIG. 17A a perspective front view of a seventeenth embodiment of a frame with endplates suitable for use in a cervical procedure;

FIG. 17B is a perspective side view of the embodiment shown in FIG. 17A;

FIG. 17C is an exploded view of the embodiment shown in FIG. 17A;

DETAILED DESCRIPTION OF THE INVENTION

Figure 1A:
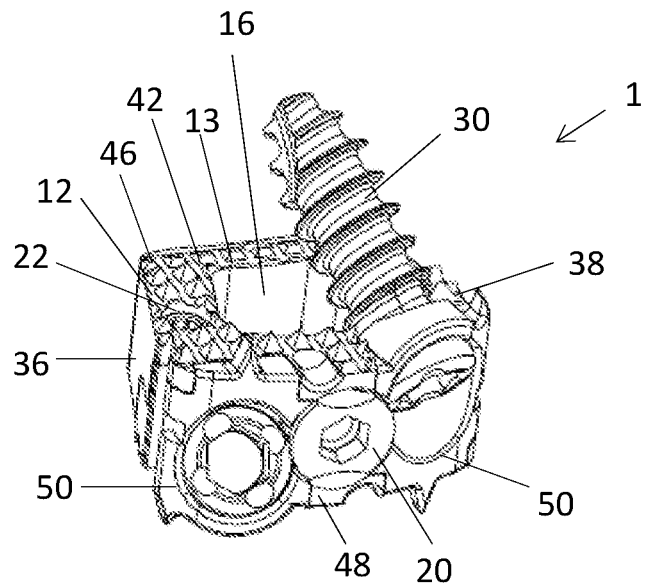
FIG. 1A is a perspective view of a first embodiment suitable for cervical interbody fusion including a spacer with inserts configured to retain bone fasteners when secure to adjacent vertebrae.

Embodiments of the disclosure are generally directed to stand-alone interbody fusion implants. Specifically, the implants include a spacer combined with at least one insert or member. The inserts or members may be included, for example, to provide openings such as through holes which are designed to retain bone fasteners, such as screws, anchors, staples, pins, nails, and the like. According to other embodiment, the implants include a frame combined with one or more endplates. The frame includes a portion with openings such as through holes which are designed to retain bone fasteners, such as screws, anchors, staples, pins, nails, and the like.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible areas.

FIGS. 1A-1E illustrate different views of one particular embodiment of the stand-alone intervertebral implant 1. As shown in the perspective view of FIG. 1A, the implant 1 includes a spacer 12 and one or more inserts 50. The inserts 50 may be especially designed and configured to define a fastener aperture 34 and/or stabilize, strengthen, and/or reinforce the spacer 12.

The spacer 12 includes a superior surface 42 and an inferior surface 44. The superior and inferior surfaces 42, 44 each have a contact area 22 configured to contact and engage adjacent vertebrae (not shown). The superior and inferior surfaces 42, 44 may be parallel, curved, or angled to help restore or recreate a lordosis angle (or other angle) of the human spine. In particular, the superior and inferior surfaces 42, 44 may have a convex curve on the upper and lower surfaces or may be angled from a distal end to a proximal end or from one lateral side to the other to account for curvature of the spine. In addition, the superior and/or inferior surfaces 42, 44 may be contoured to conform more closely to the concave endplates of the adjacent vertebra.

In order to engage the adjacent vertebrae, the spacer 12 may include a plurality of protrusions 13 or teeth on the contact areas 22 of the superior and/or inferior surfaces 42, 44. The protrusions 13 on the superior and inferior surfaces 42, 44 of each implant 1 grip the endplates of the adjacent vertebrae, resist migration, and aid in expulsion resistance. The plurality of protrusions 13 may be pyramidal in shape, but the protrusions 13 can be configured to be any size or shape to enhance anchoring the spacer 12 and the implant 1 to each of the adjacent vertebrae.

The implant 1 may contain an opening 16. The opening 16 may be in the form of an axial graft hole within the spacer 12 configured to provide the maximum amount of volume for bone graft packing. The opening 16 may be configured for receiving bone graft material, for example, to promote fusion of the adjacent vertebral bodies. The opening 16 may extend from the superior surface 42 to the inferior surface 44 of the spacer 12 to define a substantially hollow center suitable for retaining one or more bone graft materials. For example, cadaveric bone, autologous bone, bone slurry, BMP, or other similar materials, may enhance tissue growth within the intervertebral space.

The spacer 12 includes a distal end 46 and a proximal end 48. The distal end 46 of the spacer 12 may include a leading taper 40 for ease of insertion into the disc space. The leading taper 40 may be in the form of a chamfer or a bevel which enables self-distraction of the adjacent vertebral bodies during insertion of the implant 1. The leading taper 40 may be located along the insertion direction of the implant 1. For example, the leading taper 40 may assist in an anterior approach to the disc space.

Figure 1B:
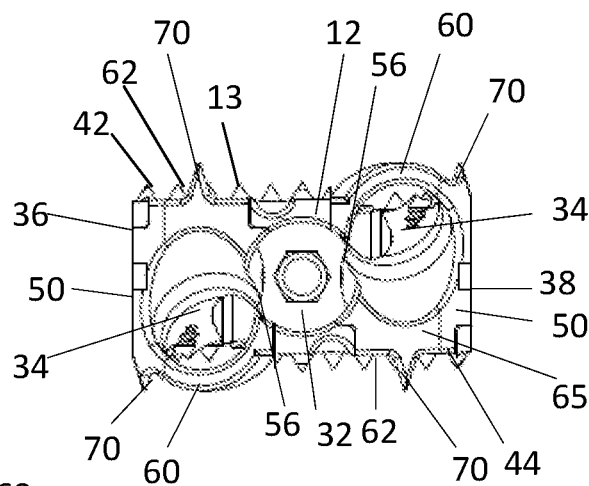
FIG. 1B is a front view of the embodiment shown in FIG. 1A.
Figure 1C:
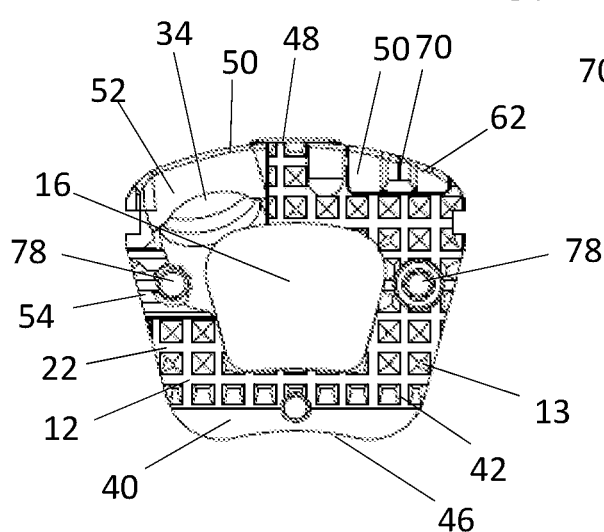
FIG. 1C is a top view of the embodiment shown in FIG. 1A.
Figure 1D:
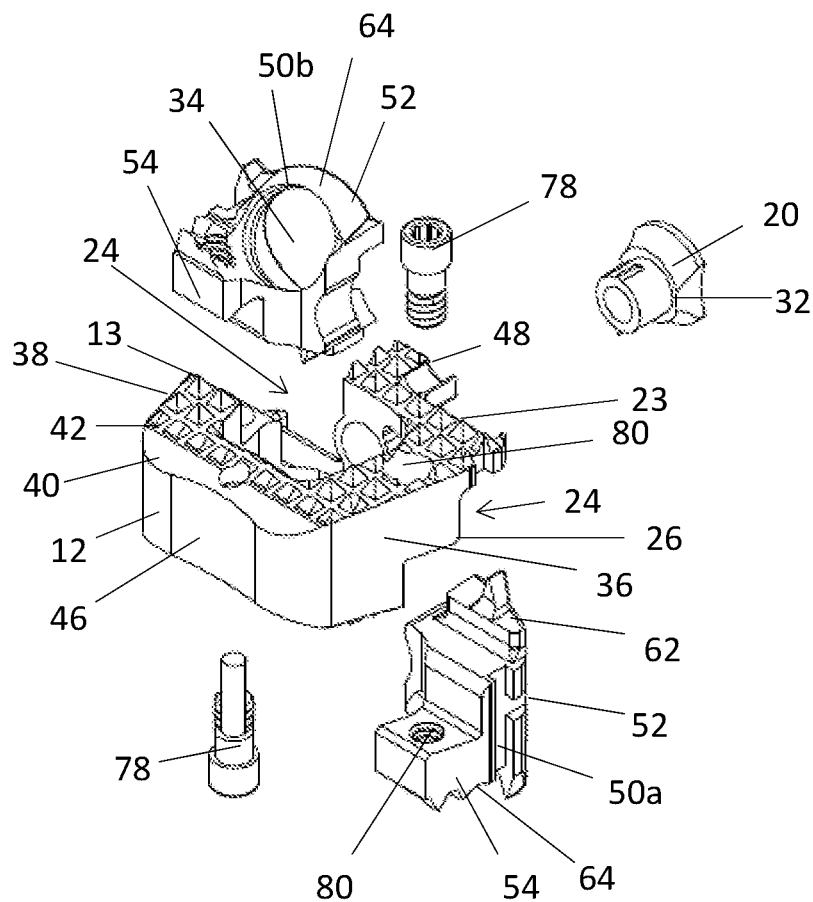
FIG. 1D is an exploded view of the embodiment shown in FIG. 1A.

As provided in FIG. 1D, the spacer 12 defines at least one cutout 24 extending from the proximal end 48 to the opening 16. In particular, the cutout 24 may be in fluid communication with the opening 16. The cutouts 24 may also be defined through a portion of the lateral sides 36, 38 to the opening 16. The cutouts 24 may be of any suitable shape and configuration, but are preferably sized and dimensioned to receive and retain at least a portion of the insert 50. For example, the cutout 24 may be sized and dimensioned to receive one or more faces or sides of the insert 50. The cutout 24 may be uniform or non-uniform and may comprise any morphology of recesses and protrusions configured to mate with the insert 50, for example, including a male/female mating. For example, the cutout 24 may be defined by one or more stepped projections 26 on the spacer 12. The cutout 24 may be defined such that the spacer 12 remains a single continuous piece (FIG. 1D) or the cutout 24 may be defined such that the spacer is broken into separate sections or pieces (not shown).

The insert 50 may be configured to comprise a fastener aperture 34, which is sized and dimensioned for receiving a fastener, such as a screw 30. Thus, the implant 1 may be secured to the adjacent vertebrae using fasteners, such as screws, anchors, staples, pins, nails, or the like.

The insert 50 is provided with a given depth and dimension designed to integrate seamlessly with the spacer 12. In particular, the depth of the insert 50 may be greater than the width and/or height of the insert 50. In addition, the insert 50 may not span across an entire frontage of the spacer 12. Instead, the inserts 50 may be provided as discrete units designed to marry with the spacer 12 only at locations needed to reinforce and/or position bone fasteners, such as screws 30. Thus, the inserts 50 may form only a portion of the front or an area proximate to the front of the implant 1. In the embodiment shown in FIG. 1A when two inserts 50 are present, the inserts 50 may be separated a distance apart with a portion of spacer 12 positioned between the two inserts 50.

As shown in FIG. 1D, the insert 50 may include a head portion 52 and at least one arm 54 projecting therefrom. The head portion 52 may be enlarged to define the opening or fastener aperture 34 configured for retaining the fastener. The head portion 52 may include a cylindrical portion forming the fastener aperture 34. The arm 54 may extend from the head portion 52 in one or more directions to contact and integrate with the spacer 12. For example, the arm 54 may extend laterally, medially, and/or posteriorly away from the head portion 52. In particular, the arm 54 may extend posteriorly away from the head portion 52 and toward the distal end 46 of the spacer 12 when attached thereto.

The insert 50 including a portion of the arm 54 and/or a portion of the head portion 52 may be configured to mirror the shape and design of the spacer 12. The spacer 12 may define at least one recess, projection, etc. sized and dimensioned to retain at least a portion of the arm 54. For example, the arm 54 or any portion of the insert 50 may rest against a portion of the spacer 12 or a recess formed therein to provide a joint, such as a lap joint, half lap joint, dovetail lap joint, beveled lap joint or scarf joint, stepped lap joint, tabled lap joint, or the like. In particular, a lap joint may include joining two pieces of material together by at least partially overlapping them (e.g., at least a portion of the insert 50 and a portion of the spacer 12 are overlapped). In a full lap, no material is removed from either of the members to be joined, resulting in a joint which is the combined thickness of the two members. In a half lap joint, material is removed from each of the members so that the resulting joint is the thickness of the thickest member. In the embodiment shown in FIG. 1E, the joint portion between the insert 50 and the spacer 12 is at least partially a half lap joint such that the joint does not increase the height of the spacer 12.

Figure 1E:
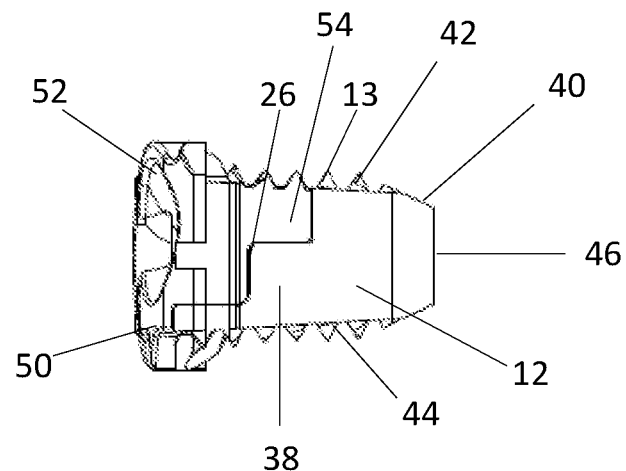
FIG. 1E is a lateral view of the embodiment shown in FIG. 1A.

As shown in FIG. 1E, the insert 50 may join the spacer 12 with a stepped lap joint. A portion of the insert 50 may be stepped with a male projection to mate with a stepped female configuration of the spacer 12. A series of offset planar surfaces having a rise and a run may form the stepped profile. For example, the arm 54 of the insert 50 may be stepped with a male projection configured to mate with corresponding stepped projections 26 on the spacer 12. Depending on the configuration of the joint, the joint may form a press-fit or friction-fit engagement to secure the insert 50 to the spacer 12 or the joint may be further secured, for example, with adhesive, pins 78, or the like.

The insert 50 is coupled to the spacer 12 such that at least a portion of the insert 50 is received in the cutout 24 in the spacer 12. The spacer 12 and the insert 50 may be coupled, removably coupled, connected, or attached together in any suitable manner known in the art. The spacer 12 and the insert 50 may also be coupled together through appropriate coupling means or fasteners. For example, the insert 50 and cutout 24 may be configured to provide male and female edges, which are the mechanical interfaces between the two pieces. Portions of the spacer 12 and the insert 50 may be assembled together using, alone or in combination, a friction fit, a dovetail assembly, dowel pins, hooks, staples, screws, adhesives, and the like, or any suitable fasteners known in the art, which can be used to permanently attach the spacer 12 and the insert 50 together.

In addition or in the alternative, the spacer 12 and the inserts 50 may be secured together with pins 78 which traverse at least a portion of the spacer 12 and/or the insert 50. For example, the arm 54 may include one or more openings 80 extending therethrough sized and configured to receive a portion of pin 78. Similarly, the corresponding portion of the spacer 12 may include one or more openings 80 extending therethrough sized and configured to receive the remainder of pin 78 to secure the arm 54 to the spacer 12. These openings 80 may or may not be threaded. The pins 78 may pass through holes 80, for example, in a substantially perpendicular manner relative to a horizontal plane to secure the joint between the insert 50 and the spacer 12. For example, the pins 78 may be oriented substantially perpendicular relative to the superior and/or inferior surfaces 42, 44 of the spacer 12. The pins 78 may be in the form of dowels or may be fully or partially threaded. The pins 78 may be formed from a biocompatible material, such as titanium, or the pins 78 may be formed from tantalum, for example, to enable radiographic visualization.

The head portion 52 of the insert 50 may include an upper surface 62 and a lower surface 64 depending on the orientation of the insert 50. For example, the two inserts 50 depicted in FIG. 1D are identical except the inserts 50 are oriented in opposite directions to fit the respective cutouts 24 in the spacer 12. The first insert 50a is oriented such that the upper surface 62 is configured to mate with a portion of the superior surface 42 of the spacer 12 and the lower surface 64 is configured to mate with a portion of the inferior surface 44 of the spacer. Conversely, the second insert 50b is oriented such that the lower surface 64 is configured to mate with a portion of the superior surface 42 of the spacer 12 and the upper surface 62 is configured to mate with a portion of the inferior surface 44 of the spacer.

The upper surface 62 and/or lower surface 64 of the head portion 52 of the insert 50 may extend a distance beyond the superior surface 42, the inferior surface 44, or both surfaces 42, 44 of the spacer 12. In particular, a portion of the head portion 52 of the insert 50 may extend above or below the superior and inferior surfaces 42, 44 of the spacer 12. For example, the lower surface 64 of the first insert 50a may extend beyond the inferior surface 44 and the lower surface 64 of the second insert 50b may extend beyond the superior surface 42 of the spacer 12.

The projection of the lower surfaces 64 of the first and second inserts 50a, 50b may be in the form of an eyebrow 60. The eyebrows 60 may fully capture the bone screws 30 while still allowing for the screw 30 to reside about, below, or above the base plane of the superior and inferior surfaces 42, 44. For example, a front surface 65 of the insert 12 may include at least one eyebrow 60 where the eyebrow 60 projects past the superior surface 42, the inferior surface 44, or both surfaces 42, 44 of the spacer 12. The eyebrow 60 may include a rounded portion. The eyebrow 60 may include a smooth surface or a roughened surface. As shown in FIG. 1B, the eyebrow 60 may be comprised of a smooth and curved surface. A lateral portion of the eyebrow 60 may further include one or more torsional stabilizers 70 configured to prevent or minimize torsional motion of the implant 1 once implanted. The torsional stabilizers 70 may act as extensions or fins, which may serve as knife edges to further purchase into the bone of the adjacent vertebrae or serve as a stop to abut anterior aspects of the adjacent vertebrae. The torsional stabilizer 70 may include a spiked or pointed projection or extension configured to engage adjacent vertebrae. In particular, the torsional stabilizer 70 may have a width substantially the same or less than a width of the eyebrow 60.

A portion of each of the upper surfaces 62 of the inserts 50 may also include an additional torsional stabilizer 70, for example, positioned opposite to the eyebrows 60. The torsional stabilizer 70 on the upper surfaces 62 may be the same or different than the torsional stabilizer 70 extending from the eyebrows 60. The upper surfaces 62 of the inserts 50 may complete a surface of the superior and inferior surfaces 42, 44 of the spacer 12 to enhance anchoring of the spacer 12. As shown in FIG. 1D, the spacer 12 may include a notch 23 in the cutout 24 in the superior and/or inferior surfaces 42, 44 of the spacer 12. The extension of the upper surface 62 including the torsional stabilizer 70 may fit in this notch 23 to form a continuous and contiguous superior and/or inferior surface for the implant 1. The notch 23 may be uniform in shape and dimension or non-uniform. In particular, the notch 23 may have a partial rectangular cross-section or may be any suitable shape to compliment the upper surface 62 of the insert 50 and complete the superior and/or inferior surfaces 42, 44 of the spacer 12.

Each insert 50 includes a screw hole or fastener aperture 34 sized and dimensioned to receive a fastener, such as screw 30. The screws 30 may be any suitable screws known in the art including fixed or variable angle. The screw hole 34 is configured to receive the screw 30 at a given angle. For example, the screw holes 34 for receiving the screw 30 may traverse the front surface 65 of the insert 50 at an angle divergent to a horizontal plane in order to secure the implant 1 to one of the adjacent vertebrae. Thus, in the case of implant 1 having two inserts 50 as shown in FIG. 1A, the screws 30 enter the screw holes 34 at specified angles to enter each of the adjacent vertebrae at the optimal locations. In particular, the screws 30 may be inserted at an angle for maximum screw purchase into the superior and inferior vertebral bodies.

The intervertebral implant 1 may be positioned in the spine after the disc portion between the two vertebral bodies is exposed and removed, for example, using rongeurs or other suitable instruments. The posterior and lateral walls of the annulus are generally preserved to provide peripheral support for the implant 1 and graft materials. A trial device attached to a trial holder may then be inserted into the disc space to determine size of the implant 1. This procedure is generally conducted using fluoroscopy and tactile feel. The implant 1 may be available in various heights and geometric options to fit the anatomical needs of a wide variety of patients. After the appropriate sized implant 1 is selected and attached to an implant holder and drill guide (not shown), the implant 1 may be inserted into the disc space. Before or after the implant 1 is positioned within the disc space, supplemental graft material can be used to enhance fusion. The implant 1 may be implanted in the vertebral space using an anterior, posterior, lateral, anterolateral, oblique, and/or transforaminal approach. The implant 1 shown in FIG. 1A may be particularly suitable for an anterior cervical procedure. The implant 1 may be in the form of a stand-alone fusion device to provide structural stability and a low or zero profile design. The implant 1 is preferably assembled before insertion into the disc space.

Once the implant 1 is positioned inside the disc space, an awl or any similar type of instrument, for example, can be used to drill through the screw hole and break the cortex of the adjacent vertebral body. The surgeon performing this procedure may then use a depth gauge to determine the screw length. Once the appropriate screw length is determined, screws 30 may be inserted using a self-retaining screwdriver, for example. Any suitable type of screw 30 may be selected by one of ordinary skill in the art. For example, the screws 30 may include fixed or variable angle screws of any suitable size with appropriate thread spacing, thread pitch, head design, length, and the like.

Once inserted, the screws 30 may be secured with an anti-back out prevention or locking mechanism 20. The locking mechanism 20 may be in the form of one or more blocking screw 32 to capture the sides of the inserted screws to prevent screw back out. As depicted in FIG. 1B, the locking mechanism 20 may be disposed on the spacer 12 for preventing back out of the screws 30. For example, a cam-style blocking mechanism may be used with screws 30 that capture the fixation device screws 30 once they are inserted fully into the inserts 50. The insert 50 may include a cutout 56 in the outer periphery of the head portion 52 configured such that the locking mechanism 20 may block or unblock the head of the screw 30. As shown, the anti-back out mechanism 20 may include a single set screw 32 that retains the screws 30 with the implant 1, although any suitable anti-back out mechanism 20 may be selected by one of ordinary skill in the art.

Figure 2A:
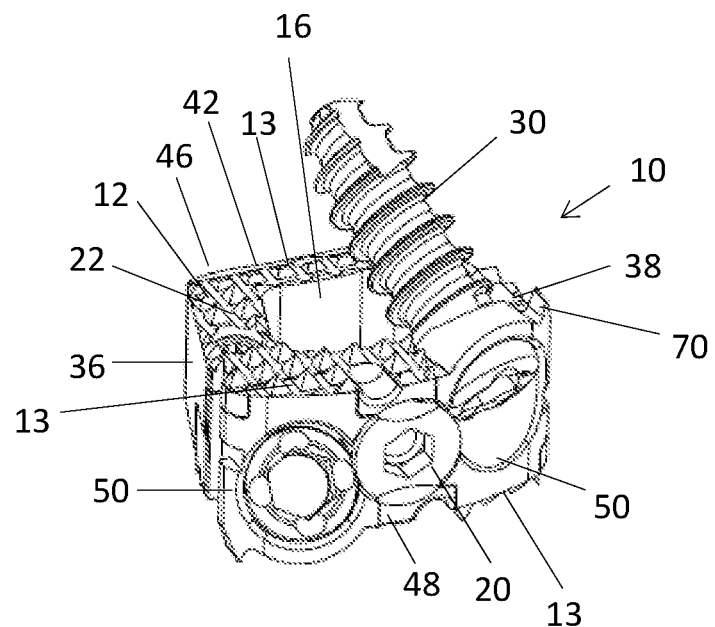
FIG. 2A shows a perspective view of an alternative embodiment of an interbody fusion device with inserts.
Figure 2B:
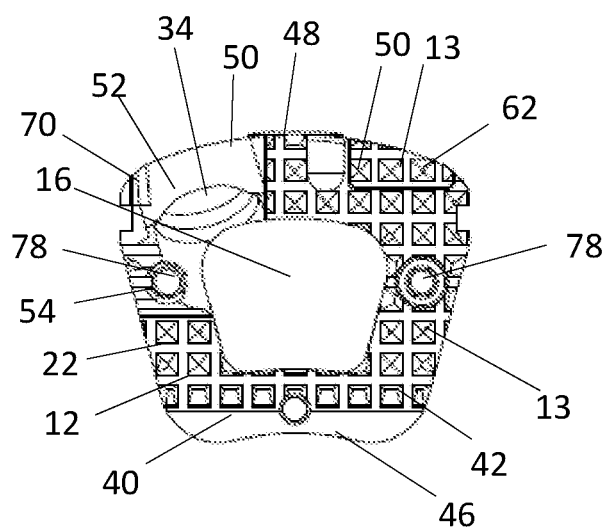
FIG. 2B is a top view of the embodiment shown in FIG. 2A.
Figure 2C:
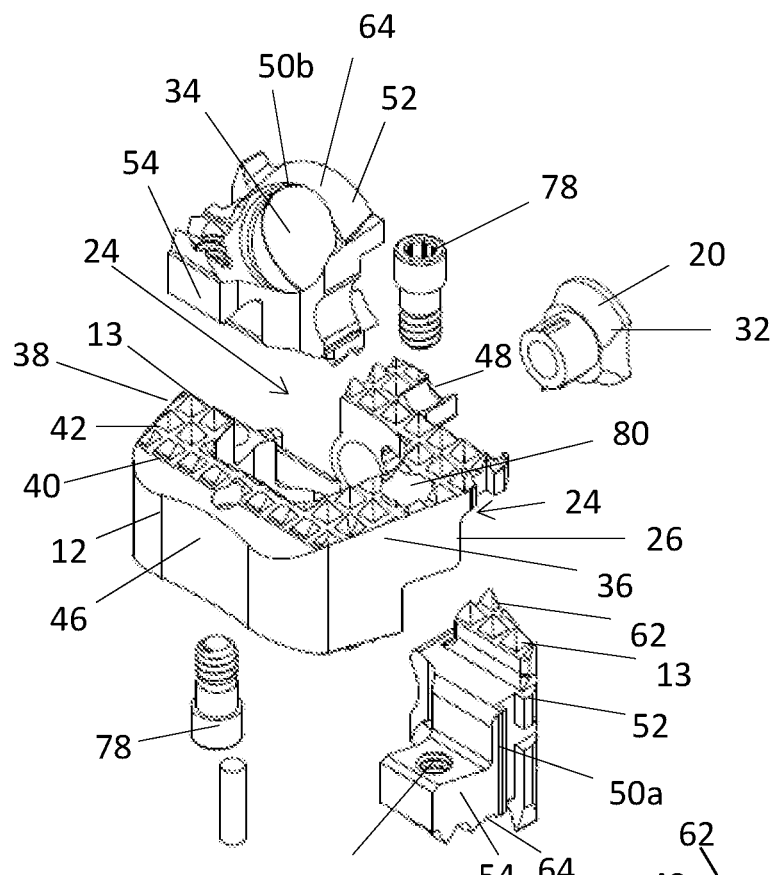
FIG. 2C is an exploded view of the embodiment shown in FIG. 2A.
Figure 2D:
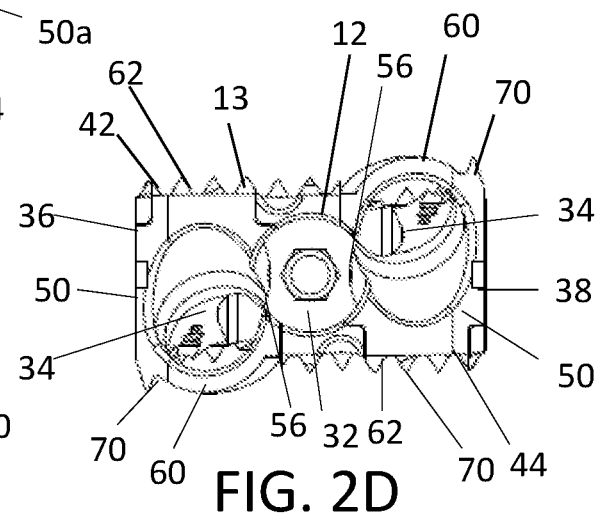
FIG. 2D is a front view of the embodiment shown in FIG. 2A.
Figure 2E:
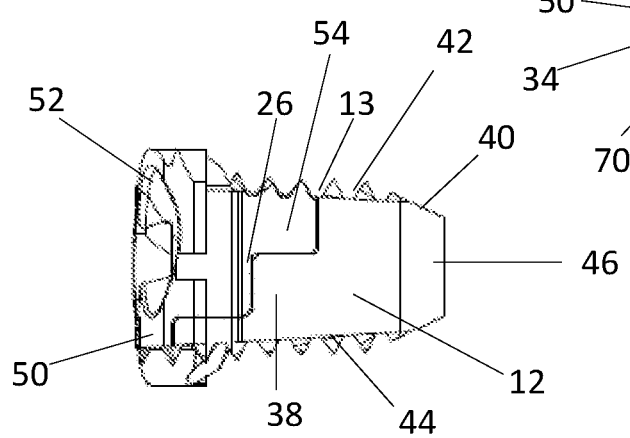
FIG. 2E is a lateral view of the embodiment shown in FIG. 2A.
Figure 3A:
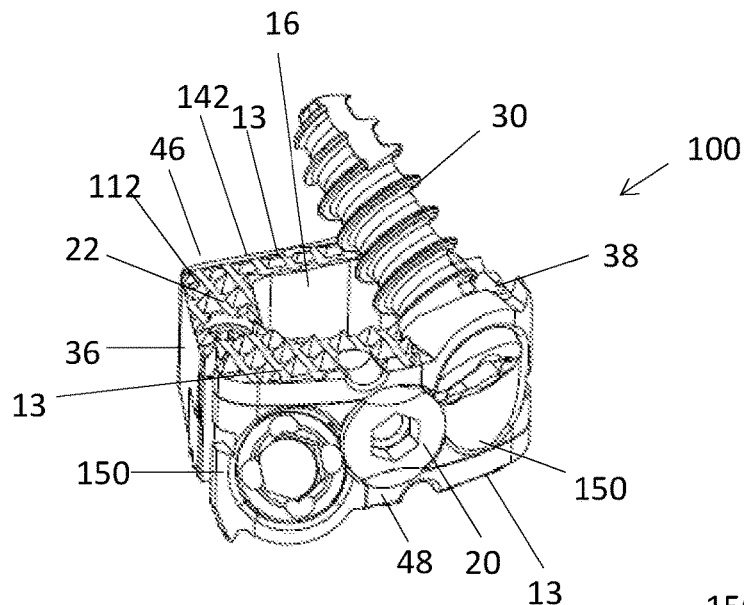
FIG. 3A is a perspective view of a third embodiment including a spacer with recessed inserts.
Figure 3B:
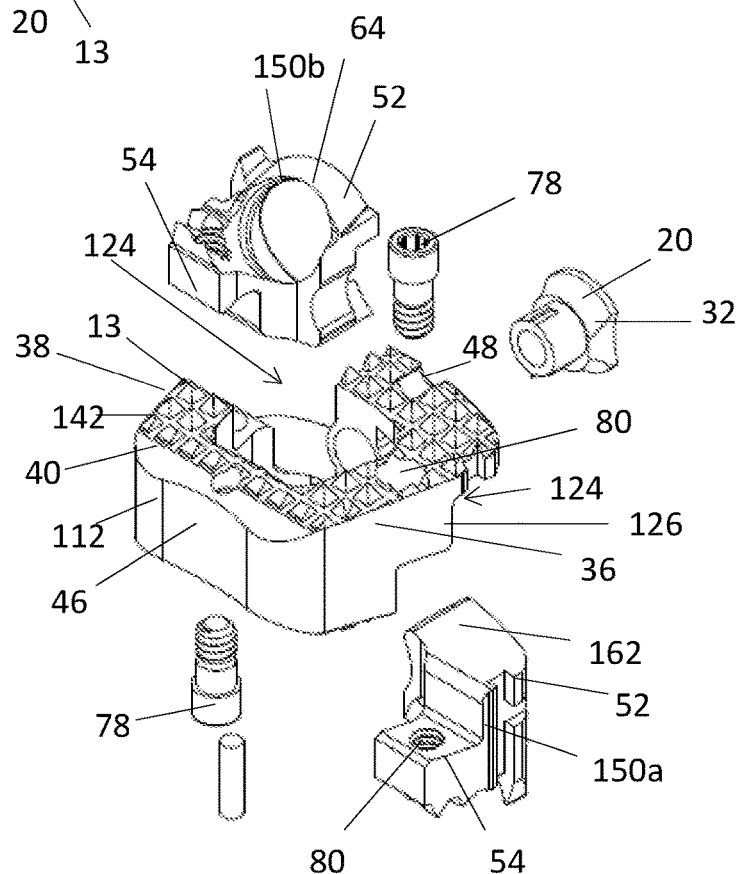
FIG. 3B shows an exploded view of the embodiment shown in FIG. 3A.
Figure 3C:
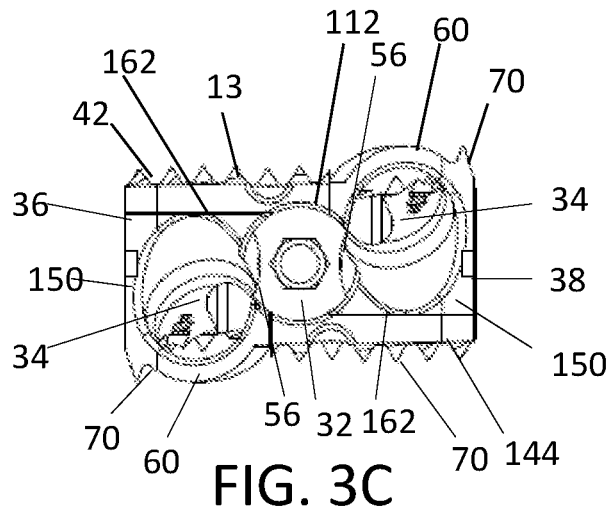
FIG. 3C shows a front view of the embodiment shown in FIG. 3A.
Figure 3D:
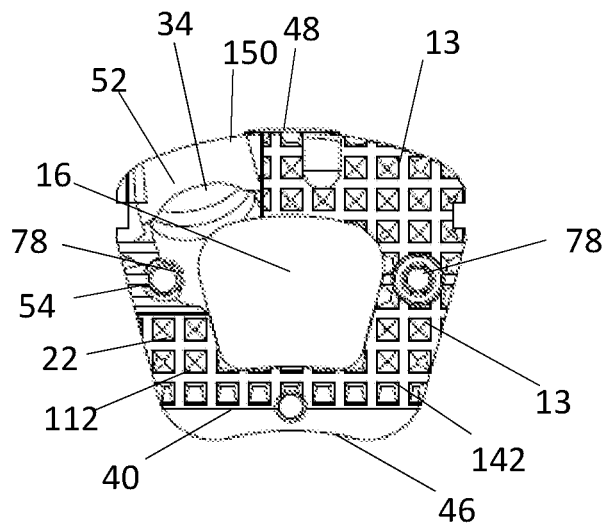
FIG. 3D is a top view of the embodiment shown in FIG. 3A.
Figure 3E:
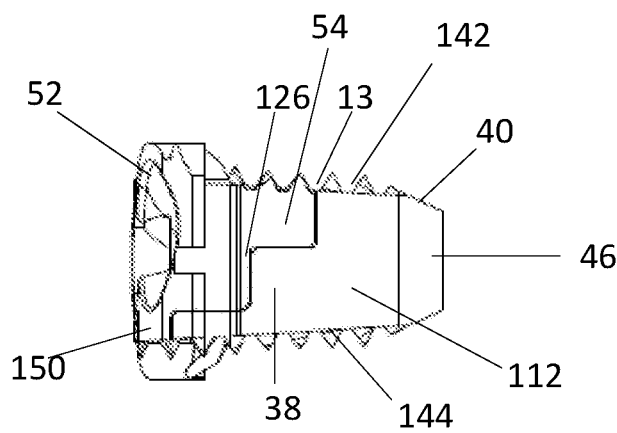
FIG. 3E is a lateral view of the embodiment shown in FIG. 3A.

FIGS. 2A-2E show alternative views of a second embodiment of an implant 10. In general, most of the structure of implant 10 is similar or comparable to the structure of implant 1. In this particular embodiment, the torsional stabilizers 70 on the upper surfaces 62 are replaced with a plurality of protrusions 13 or teeth. As shown in FIG. 2B, a portion of the upper surfaces 62 of the inserts 50a, 50b may include an extension with a plurality of protrusions 13 or teeth designed to extend the contact areas 22 of the superior and/or inferior surfaces 42, 44 of the spacer 12. The protrusions 13 on the upper surfaces 62 of the inserts 50a, 50b may complete a surface of the superior and inferior surfaces 42, 44 of the spacer 12 to enhance anchoring of the spacer 12. As shown in FIG. 2C, the spacer 12 may include the notch 23 in the cutout 24 in the superior and/or inferior surfaces 42, 44 of the spacer 12. The notch 23 may be uniform in shape and dimension or non-uniform. In particular, the notch 23 may have a partial rectangular cross-section. The extension of the upper surface 62 including the plurality of protrusions 13 may fit in this notch 23 to form a continuous and contiguous superior and/or inferior surface for the implant 10. The plurality of protrusions 13 may be the same or different than the protrusions 13 provided on the remainder of the spacer 12.

According to a third embodiment, FIGS. 3A-3E show alternative views an implant 100. In general, most of the structure of implant 100 is similar or comparable to the structure of implant 1. In this particular embodiment, different inserts 150 are provided. In particular, the upper surfaces 162 of the inserts 150a, 150b do not include a plurality of protrusions and are instead smooth. These smooth upper surfaces 162 do not complete the superior and inferior surfaces 142, 144 of the spacer 112. Instead, the smooth upper surfaces 162 are recessed and mated beneath the superior and inferior surfaces 142, 144 of the spacer 112. In addition, the cutouts 124 are modified from those shown in implant 1. For example, the superior and inferior surfaces 142, 144 of the spacer 112 are not notched to receive a portion of the insert 150, but instead extend to the proximal end 48 of the spacer. As is evident in FIG. 3B, a portion of the stepped projection 126 on the spacer 112 is extended to be contiguous and flush with the proximal end 48 of the spacer 112.

According to a fourth embodiment, FIGS. 4A-4E show an implant 200, which may be particularly suitable for an anterior lumbar procedure. In general, most of the structure of implant 200 is similar or comparable to the structure of implant 1. In this particular embodiment, three different inserts 250 provide the fastener apertures 234.

Figure 4A:
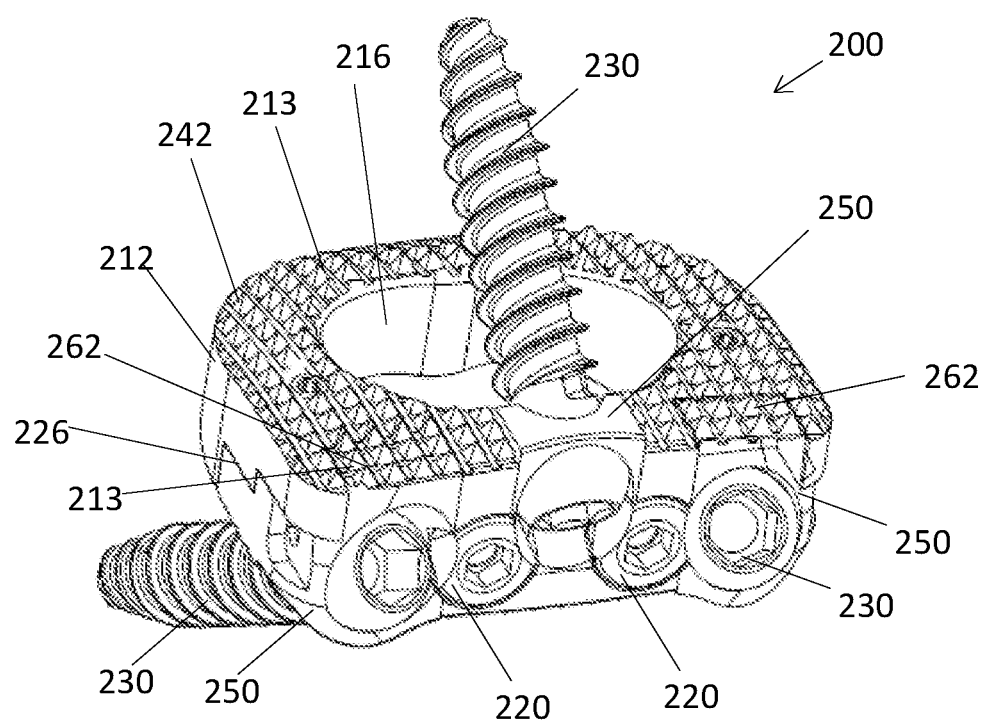
FIG. 4A shows a perspective view of a fourth embodiment of an implant suitable for lumbar interbody fusion including a spacer with three inserts.
Figure 4B:
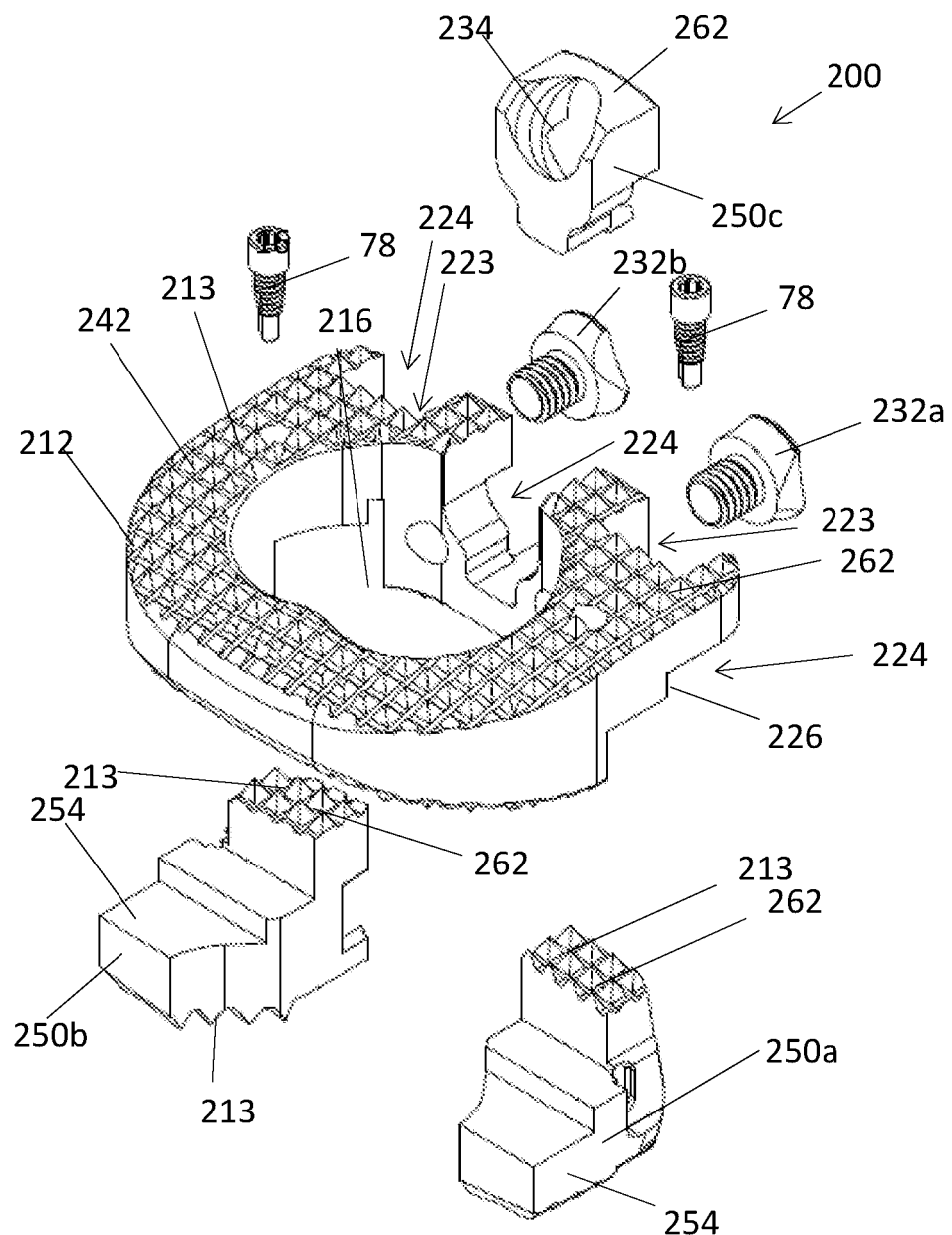
FIG. 4B is an exploded view of the embodiment shown in FIG. 4A.
Figure 4C:
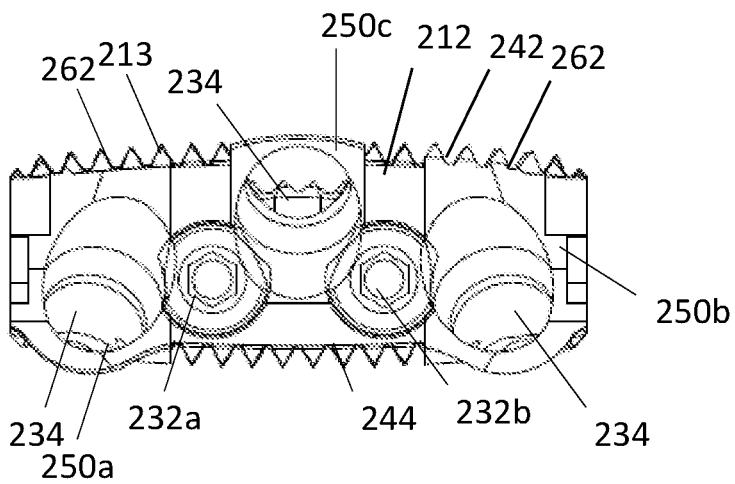
FIG. 4C is a front view of the embodiment shown in FIG. 4A.
Figure 4D:
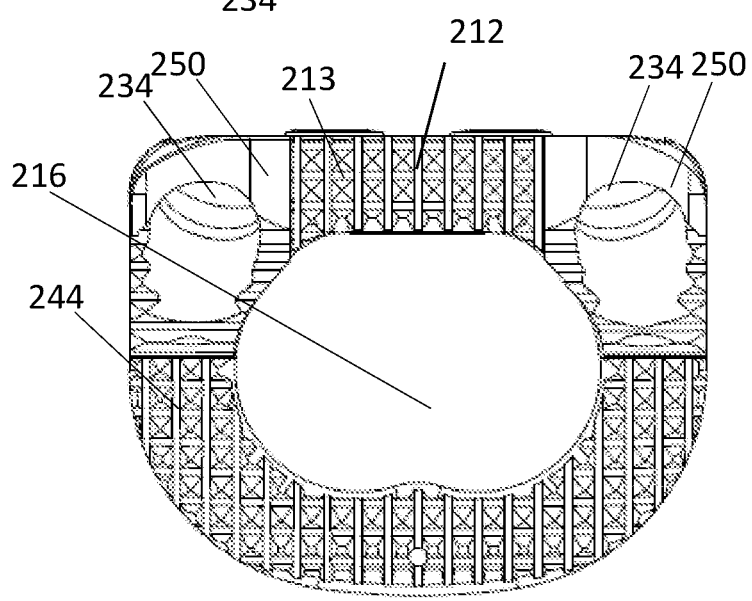
FIG. 4D is a bottom view of the embodiment shown in FIG. 4A.
Figure 4E:
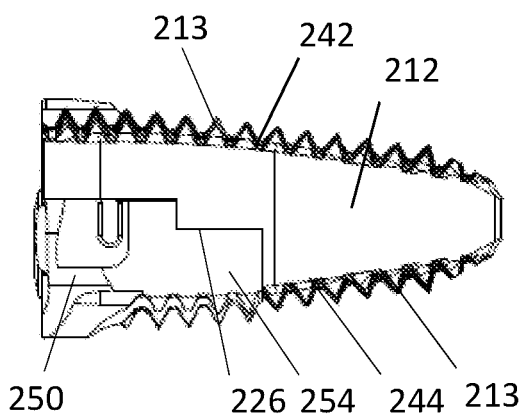
FIG. 4E is a lateral view of the embodiment shown in FIG. 4A.

As shown in FIG. 4B, a first insert 250a is identical to a second insert 250b except as mirror images of one another to fit the respective cutouts 224 in the spacer 212. The first and second inserts 250a, 250b each define a fastener aperture 234. The first and second inserts 250a, 250b are each configured to allow a bone screw 230 to engage superior or inferior vertebra. Similar to implant 1, the spacer 212 may include one or more cutouts 224 sized and configured to retain the inserts 250. The cutouts 224 may further define a stepped projection 226 configured to mate with the arm 254 of the insert 250. The arm 254 may also be stepped and configured to mate with corresponding stepped projections 226 on the spacer 212. A portion of the insert 250 may be stepped with a male projection to mate with a stepped female configuration of the spacer 212. The arm 254 may include a series of offset planar surfaces, for example, having a rise and a run, to form the stepped profile. The cutouts 224 may be in fluid communication with the opening 216 extending from the superior surface 242 to the inferior surface 244 of the spacer 212.

In addition, the spacer 212 may include one or more notches 223 in the cutout 224 in the superior surface 242 and/or inferior surface 244 of the spacer 212. The extension of the upper surface 262 of the insert 250 including the plurality of protrusions 213 may fit in the respective notch 223 to form a continuous and contiguous superior surface for the implant 200. A third insert 250c is provided between the first and second inserts 250a, 250b. The third insert 250c is different from the first and second inserts 250a, 250b and allows a bone screw 230 to engage a superior vertebra. Although the third insert 250c is depicted with a smooth upper surface 262, the third insert 250c may also include projections 213, torsional stabilizers, or the like.

The fastener apertures 234 may be configured such that the locking mechanism 220 may block or unblock the heads of the screws 230 in the respective fastener apertures 234. As shown, the anti-back out mechanism 220 may include a first set screw 232a that is configured to block a portion of the screw 230 in the first insert 250a and the screw 230 in the third insert 250c and a second set screw 232b that is configured to block a portion of the screw 230 in the second insert 250b and the screw 230 in the third insert 250c.

FIGS. 5A-5F show a fifth embodiment of an implant 300. In general, most of the structure of implant 300 is similar or comparable to the structure of implant 1. In this particular embodiment, two different inserts 350 provide the fastener apertures 334. In this case, modified arms 354 are at least partially received in at least one recess 318 in the spacer 312 to join the insert 350 to the spacer 312. The recess 318 may extend a set depth into the spacer 312 from the opening 316. The recess 318 may be in fluid communication with the opening 316. The recess 318 may be formed in the lateral portions and/or the distal portion of the opening 316. The recess 318 may be positioned substantially medially between and substantially parallel to the superior and/or inferior surfaces 342, 344 of the spacer 312. The recess 318 may be sized and dimensioned to retain at least a portion of the arm 354 of the insert 350.

Figure 5A:
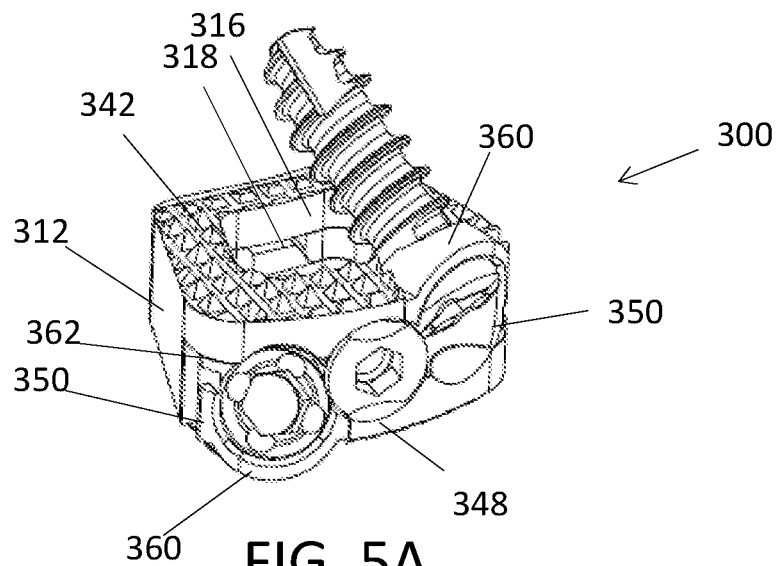
FIG. 5A is a perspective view of a fifth embodiment including inserts with head and arm portions.
Figure 5B:
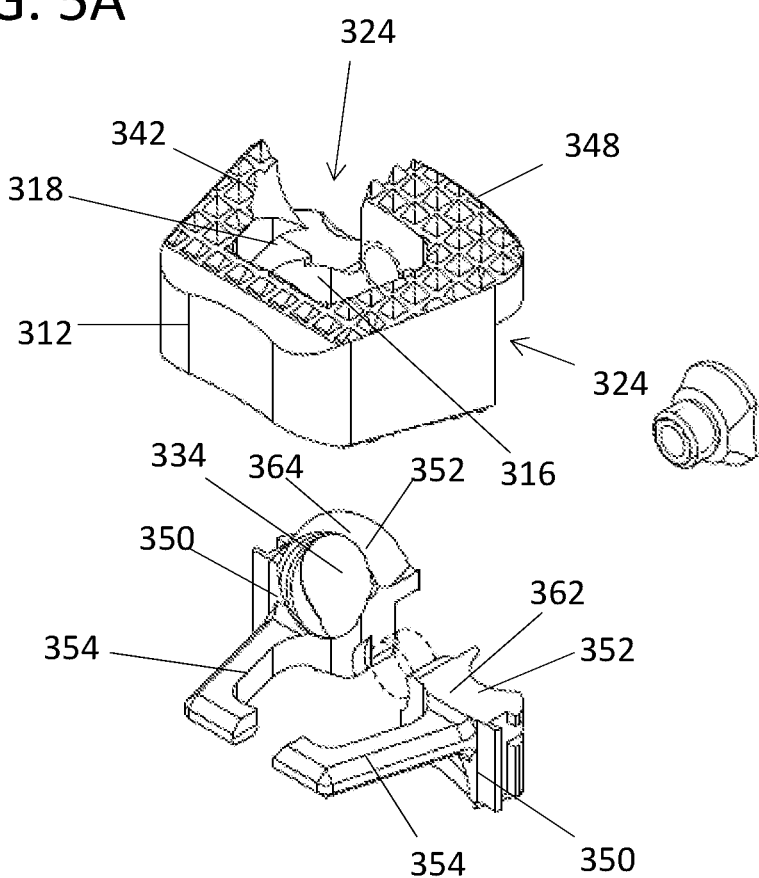
FIG. 5B shows an exploded view of the embodiment shown in FIG. 5A.
Figure 5C:
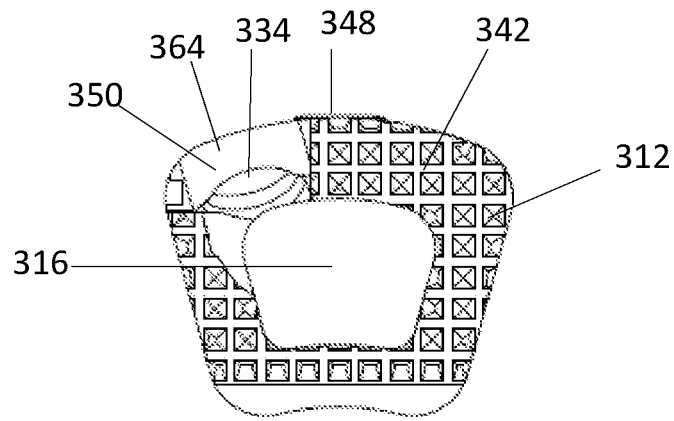
FIG. 5C shows a top view of the embodiment shown in FIG. 5A.
Figure 5D:
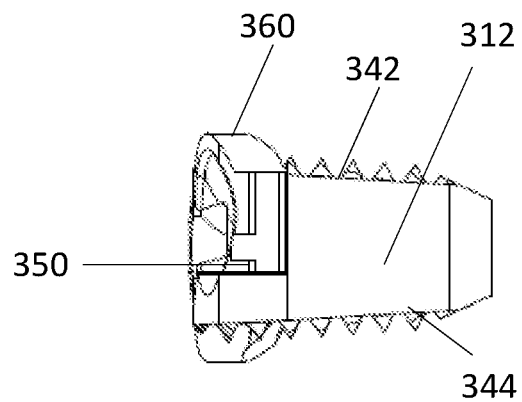
FIG. 5D is a lateral view of the embodiment shown in FIG. 5A.
Figure 5E:
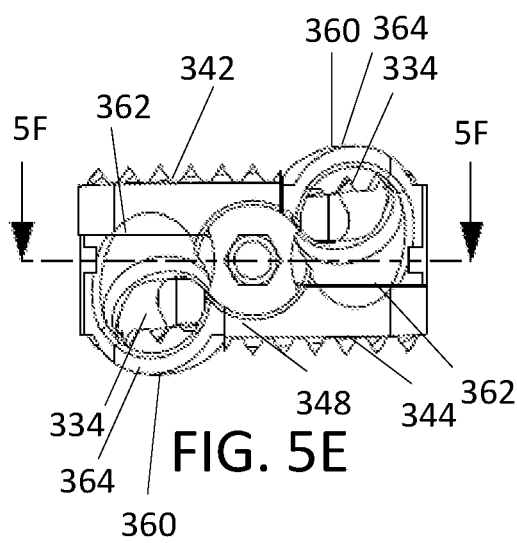
FIG. 5E is a front view of the embodiment shown in FIG. 5A.
Figure 5F:
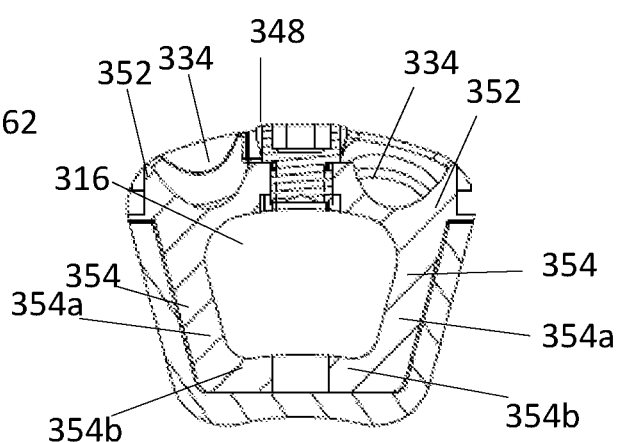
FIG. 5F is a cross-sectional view as designated in FIG. 5E.
Figure 6C:
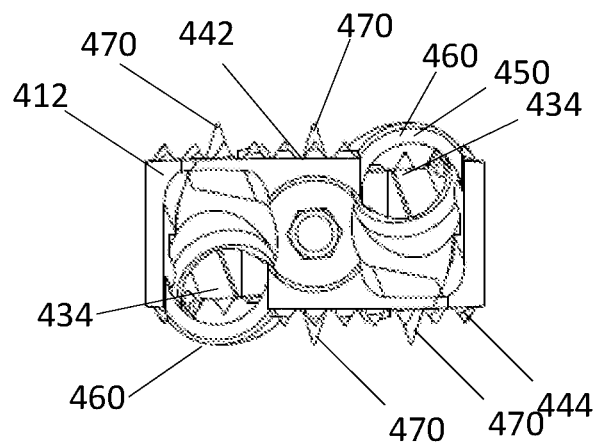
FIG. 6C is a front view of the embodiment shown in FIG. 6A.
Figure 6D:
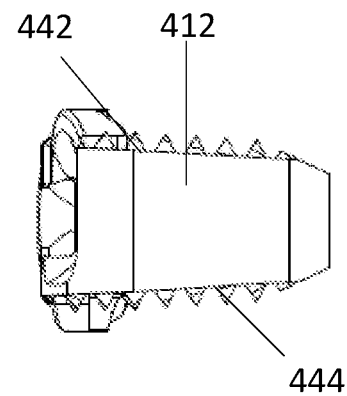
FIG. 6D is a lateral view of the embodiment shown in FIG. 6A.
Figure 6E:
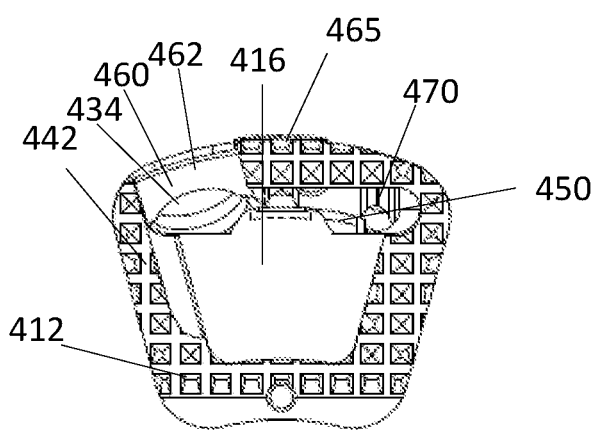
FIG. 6E is a top view of the embodiment shown in FIG. 6A.

The two inserts 350 depicted in FIG. 5B are identical except are oriented in opposite directions to fit the respective cutouts 324 in the spacer 312. The insert 350 may include head portion 352 and arm 354 extending therefrom. The arm 354 may extend posteriorly away from the head portion 352 and toward the distal end 346 of the spacer 312 when attached thereto. The arm 354 may be angled relative to the head portion 352 such that the arm 354 is oriented in a medial direction, for example, to mimic the shape of the spacer 312.

Each arm 354 of the insert 350 may include a first arm portion 354a and a second arm portion 354b. The first arm portion 354a may connect the head portion 352 of the insert 350 to the second arm portion 354b. The second arm portion 354 may be angled relative to the first arm portion 354a. The first arm portion 354a may engage the lateral portions of the recess 318 in the spacer 312, and the second arm portion 354b may engage the distal portion of the recess 318 in the spacer 312. The upper surface 362 of the insert 350 including the head portion 352, the first arm portion 354a, and the second arm portion 354b may be a continuous and contiguous coplanar surface. In the alternative, the arm 354 may be recessed beneath the upper surface 362 of the head portion 352. The arms 354 of the inserts 350 may join the spacer 312 via a press-fit or friction-fit engagement to secure the insert 350 to the spacer 312 or the joint may be further secured, for example, with adhesive, pins, or the like.

Similar to implant 1, the lower surface 364 of the head portion 352 of the insert 350 may extend a distance beyond the superior surface 342, the inferior surface 344, or both surfaces 342, 344 of the spacer 312. For example, the lower surface 364 of the first insert 350a may extend beyond the inferior surface 344 and the lower surface 364 of the second insert 350b may extend beyond the superior surface 342 of the spacer 312. The projection of the lower surfaces 364 of the first and second inserts 350a, 350b may be in the form of eyebrows 360. In this embodiment, the eyebrow 360 includes a substantially smooth and curved surface. In the embodiment shown, no torsional stabilizers are present, but one or more torsional stabilizers may be added if desired.

Similar to implant 100, the upper surfaces 362 of the inserts 350a, 350b do not include a plurality of protrusions and are instead smooth. These smooth upper surfaces 362 do not complete the superior and inferior surfaces 342, 344 of the spacer 312. Instead, the smooth upper surfaces 362 are recessed and mated beneath the superior and inferior surfaces 342, 344 of the spacer 312. In addition, the cutouts 324 are different from those shown in implant 1. For example, the superior and inferior surfaces 342, 344 of the spacer 312 are not notched to receive a portion of the insert 350, but extend to the proximal end 348 of the spacer.

FIGS. 6A-6E show a sixth embodiment of an implant 400 including a single member 450 recessed behind the front portion of the spacer 412. In general, most of the structure of implant 400 is similar or comparable to the structure of implant 1. Unlike the individual inserts 50 provided for each fastener aperture 34 in implant 1, in this particular embodiment, a single member 450 provides all of the fastener apertures 434.

In this embodiment, the single member 450 provides two fastener apertures 434 to secure fasteners in both the superior and inferior vertebrae. This member 450 may be provided with or without arms. The member 450 may be recessed in the spacer 412 and positioned posterior to the front surface 465 of the spacer 412. In particular, the member 450 may be positioned within the opening 416 such that a first portion of the member 450 is received in a first cutout 424 in the spacer 412 and a second portion of the member 450 is received a second cutout 424 in the spacer 412. The member 450 may be curved and contoured to follow a proximal portion of the spacer 412.

Similar to implant 1, the upper and/or lower surfaces 462, 464 of the member 450 may extend a distance beyond the superior surface 442, the inferior surface 444, or both surfaces 442, 444 of the spacer 412. For example, a portion of the upper surface 462 of the member 450 may extend above the superior surface 442 and a portion of the lower surface 464 may extend below the inferior surface 444 of the spacer 412. The projections of the upper and lower surfaces 462, 464 of the single member 450 may be in the form of eyebrows 460. In this embodiment, the eyebrows 460 include a substantially smooth and curved surface. In the embodiment shown, torsional stabilizers 470 are provided opposite to the eyebrows 460 and are also provided substantially medially on the member 450 projecting superiorly and inferiorly from both the upper and lower surfaces 462, 464, respectively. The torsional stabilizers 470 may include a spiked or pointed projection or extension configured to engage adjacent vertebrae.

According to a seventh embodiment, FIGS. 7A-7E depict an implant 500 with a different type of insert 550. In general, most of the structure of implant 500 is similar or comparable to the structure of implant 1. Unlike the inserts 50 provided with arm 54 in implant 1, in this particular embodiment, the insert 550, which provides the fastener aperture 534, does not contain an arm and is directly recessed into at least one slot 518 in the spacer 512.

Figure 7A:
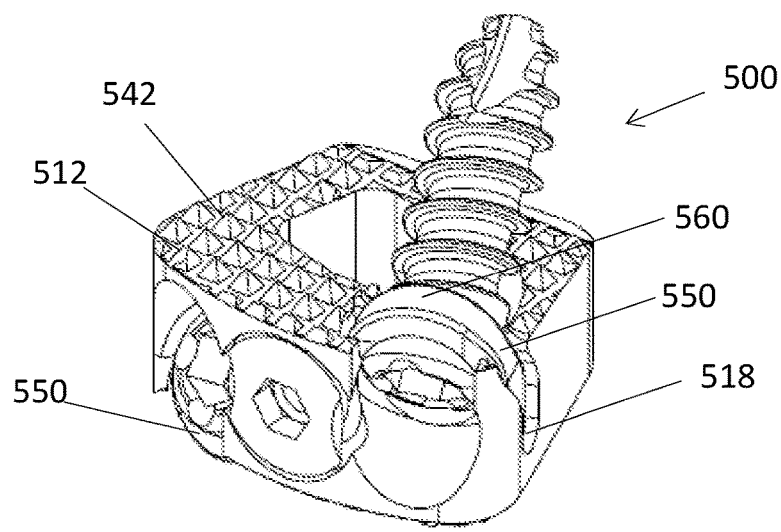
FIG. 7A shows a perspective view of a seventh embodiment with alternative inserts.
Figure 7B:
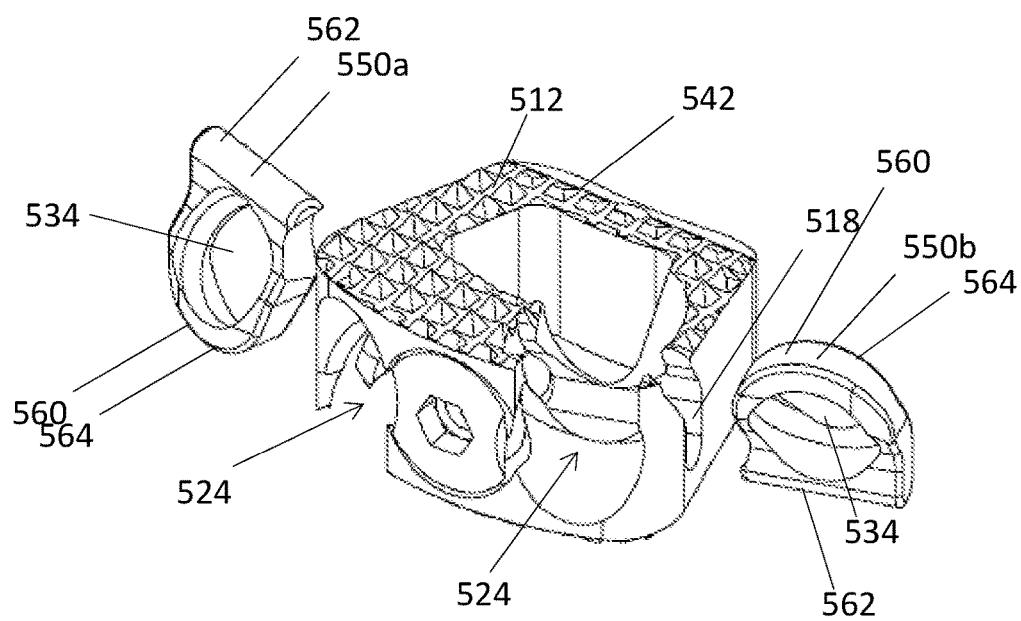
FIG. 7B shows an exploded view of the embodiment shown in FIG. 7A.
Figure 7C:
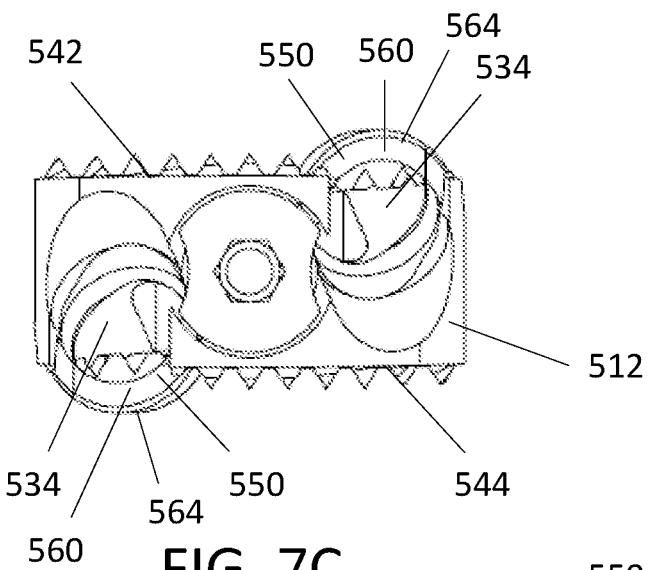
FIG. 7C is a front view of the embodiment shown in FIG. 7A.
Figure 7D:
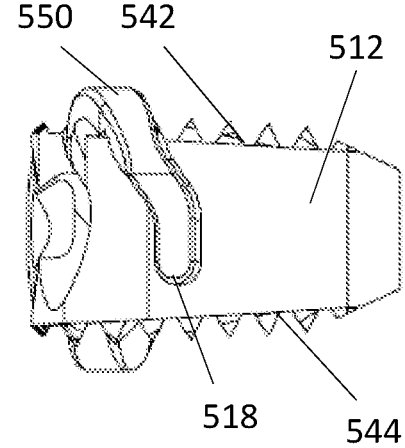
FIG. 7D is a lateral view of the embodiment shown in FIG. 7A.

The two inserts 550 depicted in FIG. 7B are identical except are oriented in opposite directions to fit the respective cutouts 524 in the spacer 512. The insert 550 may be curved or may contain one or more angled transitions. At least a portion of the inserts 550 may join the spacer 512 via a press-fit or friction-fit engagement to secure the insert 550 to the spacer 512 or the joint may be further secured, for example, with adhesive, pins, or the like.

In this embodiment, the inserts 550 are at least partially received in at least one slot 518 in the spacer 512 to join the insert 550 to the spacer 512. The slot 518 may extend a set depth into the spacer 512 from the cutout 524. For example, the slot 518 may be formed in an inferior or superior portion of the cutout 524 and may be in fluid communication with the cutout 524. The slot 518 may include more than one portion including an angled portion, for example. The angled portion may connect the eyebrow 560 to a planar portion. The planar portion may be positioned substantially perpendicular to the superior and/or inferior surfaces 542, 544 of the spacer 12. The slot 518 may be sized and dimensioned in any suitable configuration to retain at least a portion of the insert 550. For example, the upper surface 562 of the insert 550 may contact and fit within the slot 518. The upper surfaces 562 of the inserts 550 may be substantially smooth or may be textured. The upper surface 562 may also be curved or rounded as shown. These smooth upper surfaces 562 are recessed and mated beneath the superior and inferior surfaces 542, 544 of the spacer 512.

Figure 7E:
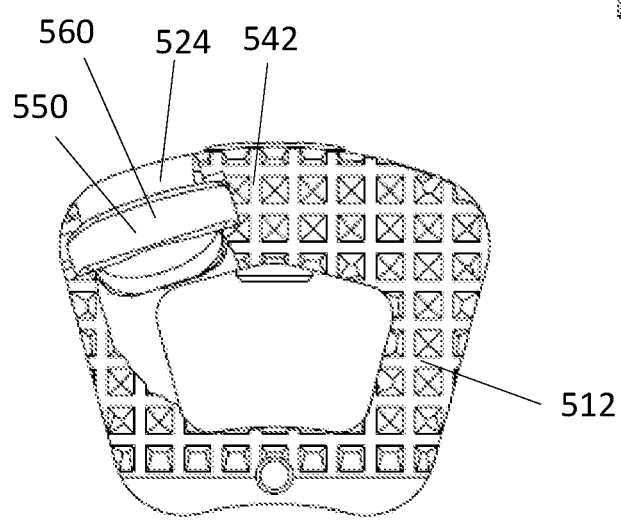
FIG. 7E is a top view of the embodiment shown in FIG. 7A.

In this embodiment, the depth of the insert 550 may be the same or smaller than the depth of the proximal portion of the spacer. In other words, the insert 550 does not need to fill the entire depth of the cutout 524. As shown in FIG. 7E, the insert 550 fills only a portion of the cutout 524. In this embodiment, the insert 550 is positioned substantially centrally in the cutout 524, but it is envisioned that the insert 550 may be positioned at any suitable location in the cutout 524.

Similar to implant 1, the lower surface 564 of the insert 550 may extend a distance beyond the superior surface 542, the inferior surface 544, or both surfaces 542, 544 of the spacer 512. For example, the lower surface 564 of the first insert 550a may extend below the inferior surface 544 and the lower surface 564 of the second insert 550b may extend above the superior surface 542 of the spacer 512. The projection of the lower surfaces 564 of the first and second inserts 550a, 550b may be in the form of an eyebrow 560. In this embodiment, the eyebrow 560 includes a substantially smooth and curved surface. In the embodiment shown, no torsional stabilizers are present, but one or more torsional stabilizers may be added if desired.

FIGS. 8A-8E provide an eighth embodiment of an implant 600 where the inserts 650 are in the form of rings. In general, most of the structure of implant 600 is similar or comparable to the structure of implant 1. In addition, this embodiment is similar to the implant 500 discussed above.

Figure 8A:
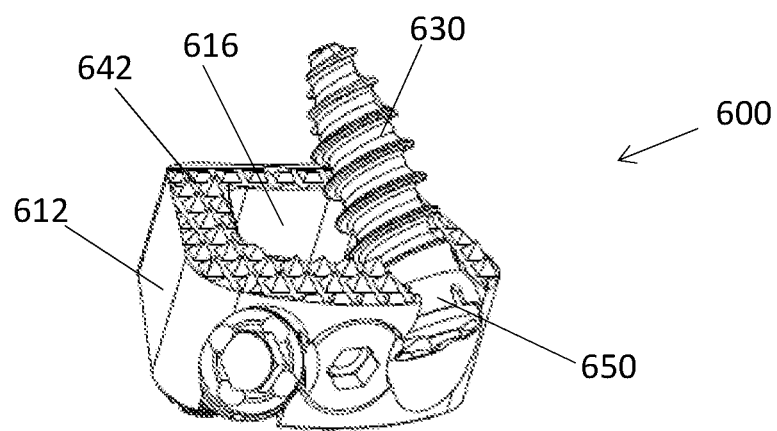
FIG. 8A provides a perspective view of an eight embodiment where the inserts are in the form of rings.
Figure 8B:
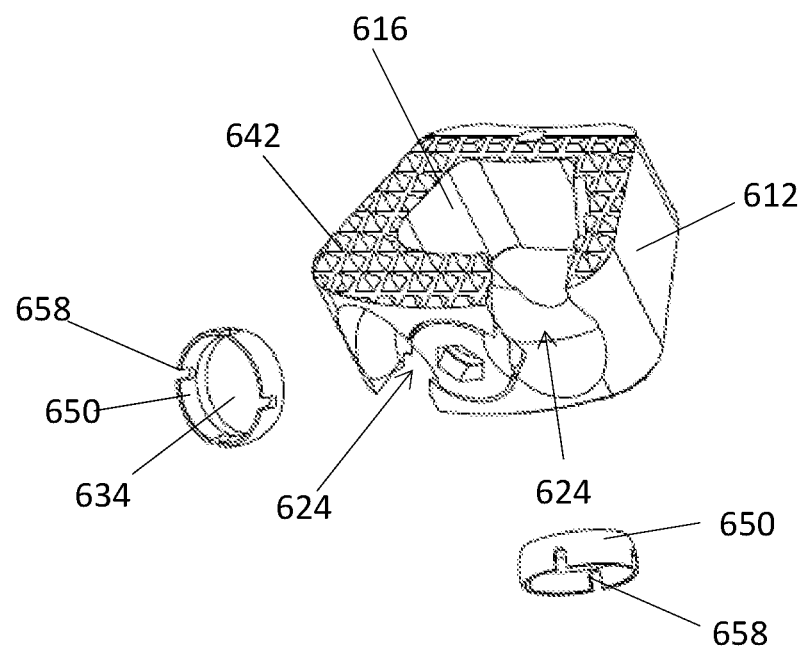
FIG. 8B shows an exploded view of the embodiment shown in FIG. 8A.
Figure 8C:
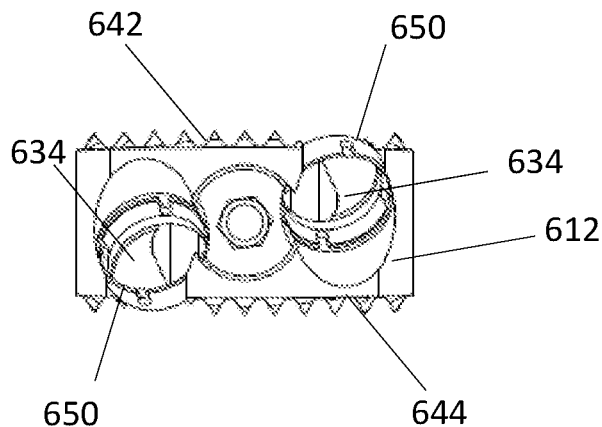
FIG. 8C is a front view of the embodiment shown in FIG. 8A.
Figure 8D:
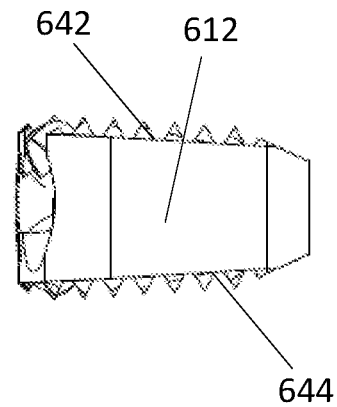
FIG. 8D is a lateral view of the embodiment shown in FIG. 8A.
Figure 8E:
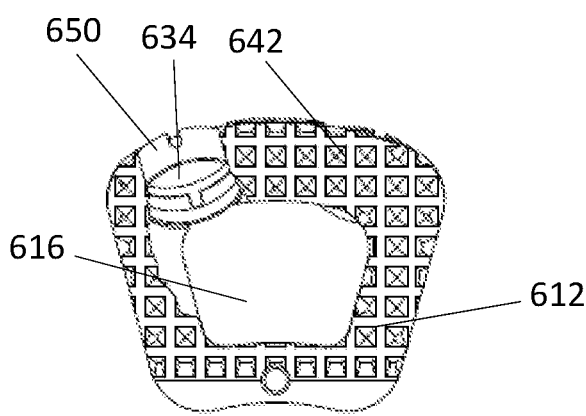
FIG. 8E is a top view of the embodiment shown in FIG. 8A.

In this embodiment, the insert 650 is in the form of a ring or cylinder. The ring insert 650 may be provided with one or more slits 658, for example, to allow the insert 650 to tightly mate with the cutout 624 through the spacer 612 and secure the insert 650 to the spacer 612. In particular, one or more slits 658 may be longitudinally positioned around a periphery of the ring-shaped insert 650. The slits 658 may be uniformly or non-uniformly positioned around the insert 650. As shown in FIG. 8B, the slits 658 may be positioned in 90° increments around the ring insert 650. For example, four slits 658 may be positioned around the periphery of the ring insert 650. The slits 658 may be oriented such that the open ends of the slits 658 face anteriorly.

The insert 650 may be received in a recess in the cutout 624 or may be positioned within the cutout 624. The cutouts 624 may be in fluid communication with the opening 616 extending from the superior surface 642 to the inferior surface 644 of the spacer 612. The insert 650 may be configured to at least partially define and reinforce the fastener aperture 634. At least a portion of the inserts 650 may join the spacer 612 via a press-fit or friction-fit engagement to secure the insert 650 to the spacer 612. The insert 650 may be further secured, for example, with adhesive or the like.

In this embodiment, the depth of the insert 650 may be the same or smaller than the depth of the proximal portion of the spacer. In other words, the insert 650 does not need to fill the entire depth of the cutout 624. In this embodiment, the insert 650 is positioned at an angle in the cutout 624 to accommodate the angles of the bone screws 630. It is envisioned that the insert 650 may be positioned at any suitable location in the cutout 624.

Figure 9A:
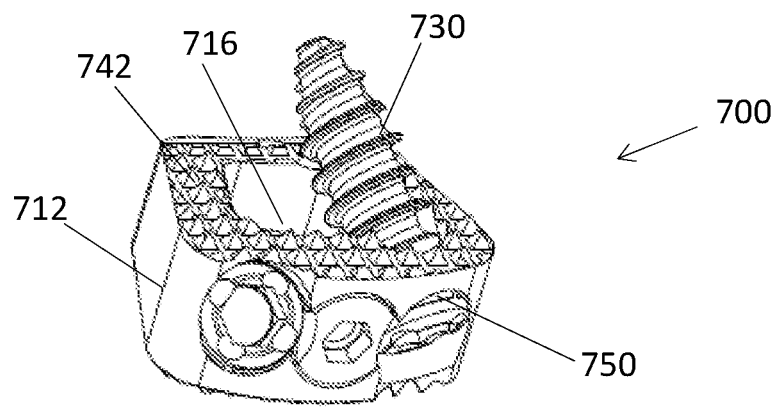
FIG. 9A is a perspective view of a ninth embodiment where the inserts have a c-shaped configuration.
Figure 9B:
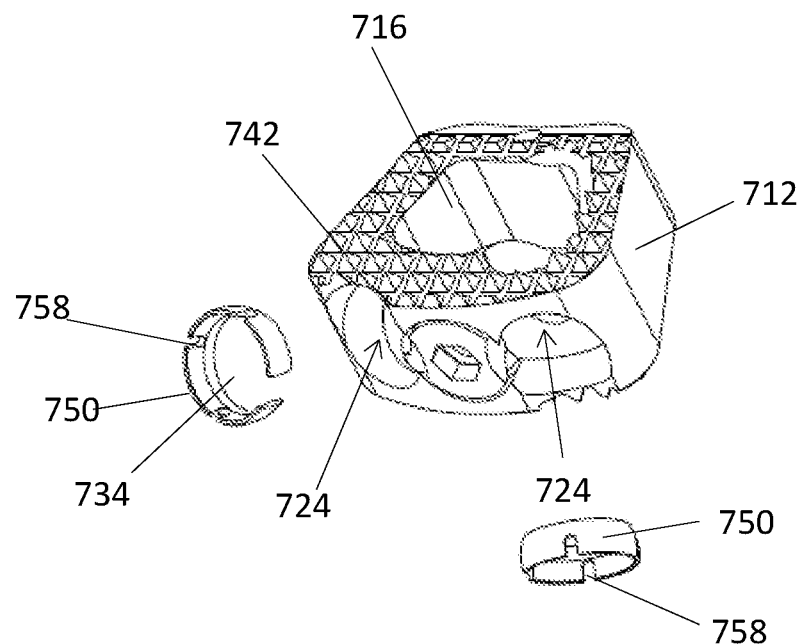
FIG. 9B shows an exploded view of the embodiment shown in FIG. 9A.
Figure 9C:
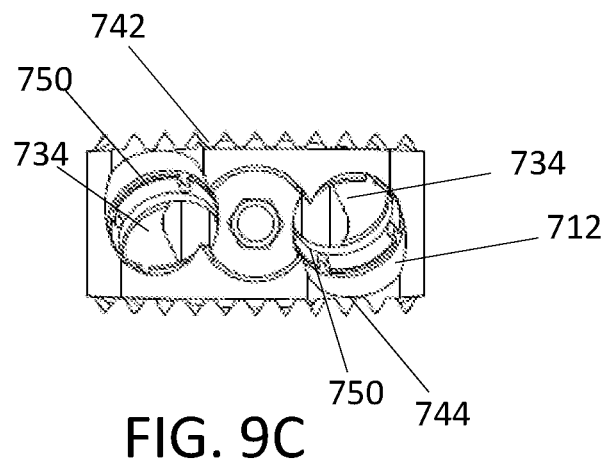
FIG. 9C is a front view of the embodiment shown in FIG. 9A.
Figure 9D:
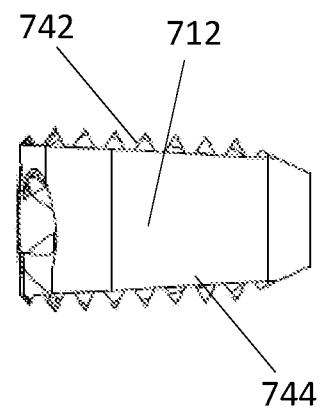
FIG. 9D is a lateral view of the embodiment shown in FIG. 9A.
Figure 9E:
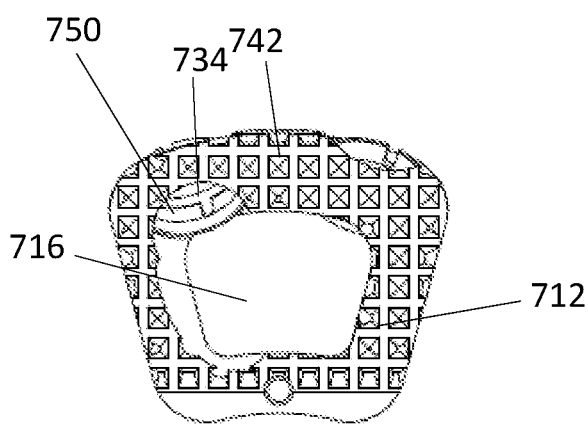
FIG. 9E is a top view of the embodiment shown in FIG. 9A.

FIGS. 9A-9E provide a ninth embodiment of an implant 700. In general, most of the structure of implant 700 is similar or comparable to the structure of implant 1. In addition, this embodiment is substantially the same as the implant 600 discussed above, and the discussion for implant 600 applies equally here. In this particular embodiment, the insert 750 has a c-shaped cross-section instead of being in the form of a ring. The c-shaped inserts 750 shown in FIG. 9B are the same except are oriented differently. The c-shaped inserts 750 are substantially the same as the ring inserts 650 except a gap separates the insert 750 to allow for further compression and/or expansion of the insert 750.

The c-shaped insert 750 may also be provided with one or more slits 758, for example, to allow the insert 750 to tightly mate with the cutout 724 through the spacer 712 and secure the insert 750 to the spacer 712. In particular, one or more slits 758 may be longitudinally positioned around a periphery of the c-shaped insert 750. The slits 758 may be uniformly or non-uniformly positioned around the insert 750. The slits 758 may also positioned in 90° increments around the c-shaped insert 750. For example, three slits 758 may be positioned around the periphery of the ring insert 750. The slits 758 may be oriented such that the open ends of the slits 758 face anteriorly.

The insert 750 may be received in a recess in the cutout 724 or may be positioned within the cutout 724. The cutouts 724 may be in fluid communication with the opening 716 extending from the superior surface 742 to the inferior surface 744 of the spacer 712. The insert 750 may be configured to at least partially define the fastener aperture 734. At least a portion of the inserts 750 may join the spacer 712 via a press-fit or friction-fit engagement to secure the insert 750 to the spacer 712. The insert 750 may also be secured, for example, with adhesive or the like. In this embodiment, the depth of the insert 750 may be the same or smaller than the depth of the proximal portion of the spacer. Similar to insert 650, the c-shaped insert 750 does not need to fill the entire depth of the cutout 724. In this embodiment, the insert 750 is positioned at an angle in the cutout 724 to accommodate the angles of the bone screws 730, but it is envisioned that the insert 750 may be positioned at any suitable location in the cutout 724 so long as the necessary reinforcement is provided to the fasteners.

Figure 10A:
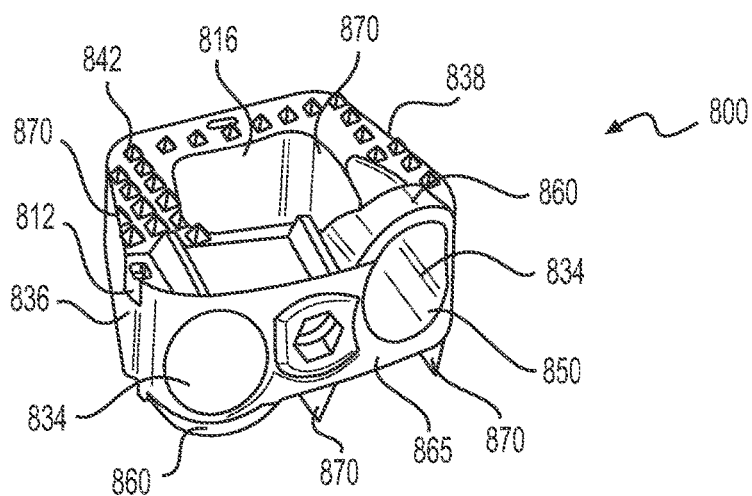
FIG. 10A is a perspective view of a tenth embodiment including a single insert with a clamp-like design.
Figure 10B:
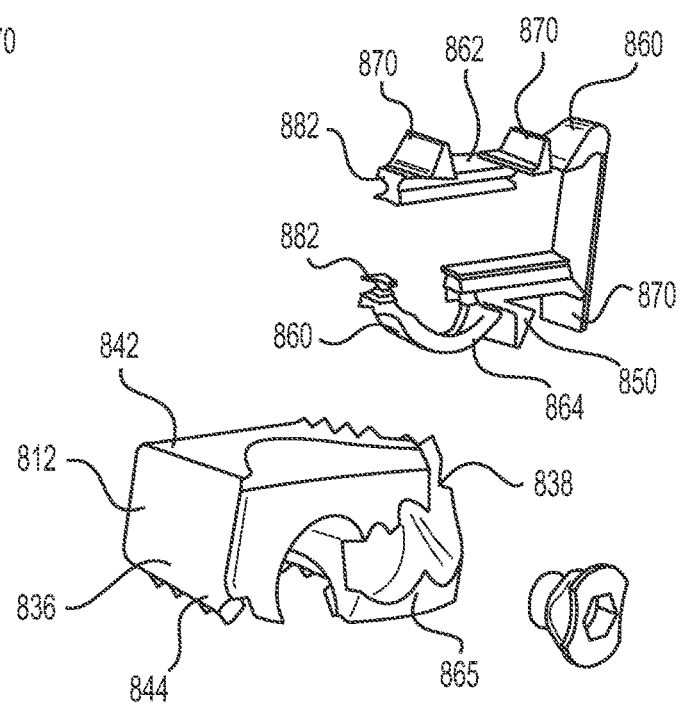
FIG. 10B is an exploded view of the embodiment shown in FIG. 10A.
Figure 10C:
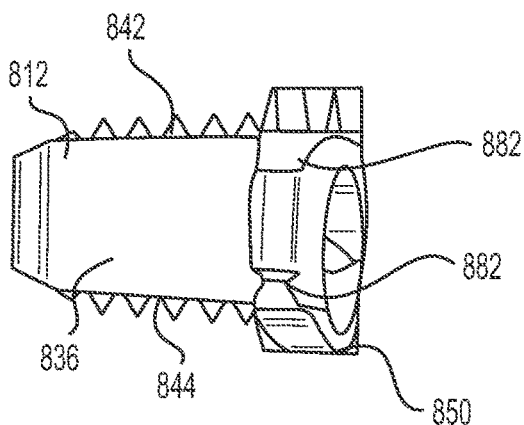
FIG. 10C is a lateral view of the embodiment shown in FIG. 10A.
Figure 11C:
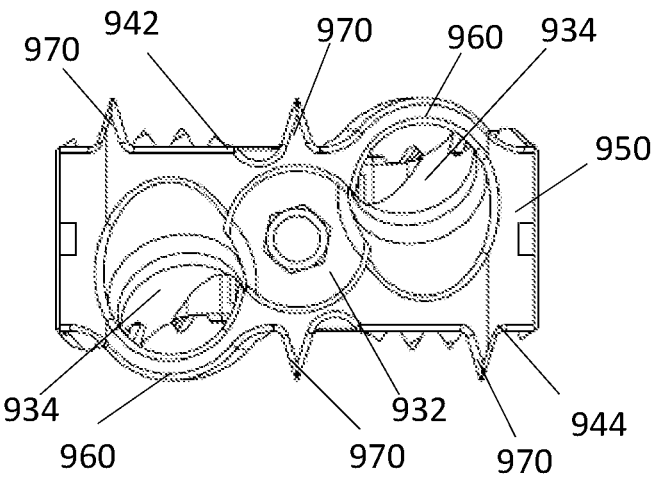
FIG. 11C is a front view of the embodiment shown in FIG. 11A.
Figure 11D:
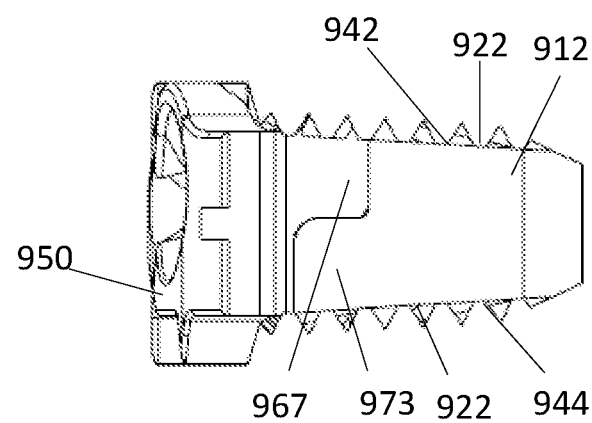
FIG. 11D is a lateral view of the embodiment shown in FIG. 11A.
Figure 11E:
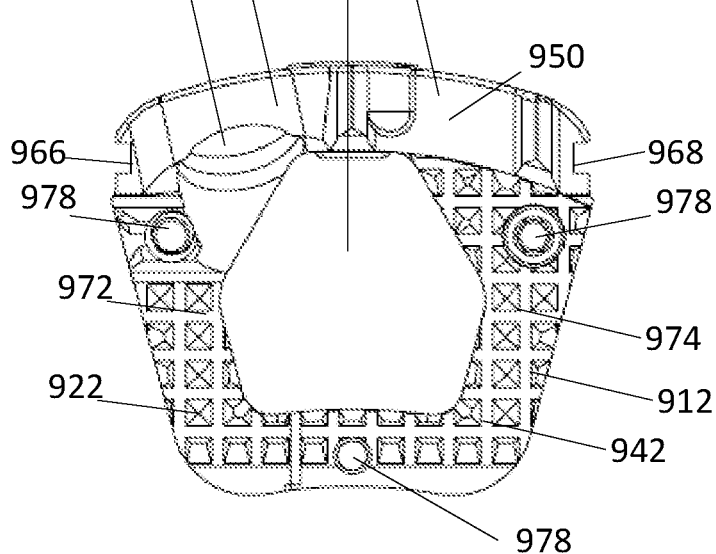
FIG. 11E is a top view of the embodiment shown in FIG. 11A.

According to a tenth embodiment, FIGS. 10A-10C provide an implant 800 with a member 850. In general, most of the structure of implant 800 is similar or comparable to the structure of implant 1. Unlike the individual inserts 50 provided for each fastener aperture 34 in implant 1, in this particular embodiment, a member 850 provides all of the fastener apertures 834. The member 850 may be in the form of a clamp or clip, which surrounds a proximal portion of the spacer 812.

In this embodiment, the member 850 provides two fastener apertures 834 to secure fasteners in both the superior and inferior vertebrae. This member 850 may be provided with or without arms. The member 850 may be positioned posterior to the front surface 865 of the spacer 812. In particular, the member 850 may be positioned to surround or envelop a portion of at least one lateral side 836, 838 and a portion of the superior and/or inferior surfaces 842, 844 of the spacer 812. The member 850 may be contoured, for example, to begin at one lateral side 836 wrap around a portion of the superior surface 842 to define one of the fastener apertures 834, wrap around the other lateral side 838, wrap under a portion of the inferior surface 844 to define the other fastener aperture 834, and terminate at the lateral side 836. The member 850 may begin and terminate at one lateral side 836, 838, for example, using one or more clamping features 882. The clamping features 882 may include prongs or springs which attach or secure the member 850 to the spacer 812. Although the member 850 is depicted as a single piece, it is envisioned that the clamping member 850 may be comprised of more than one part so long as the member 850 may clamp to the spacer 812 and provide the fastener apertures 834.

A portion of the upper and/or lower surfaces 862, 864 of the member 850 may extend a distance beyond the superior surface 842, the inferior surface 844, or both surfaces 842, 844 of the spacer 812. For example, a portion of the upper surface 862 may extend above the superior surface 842 and a portion of the lower surface 864 may extend below the inferior surface 844 of the spacer 812. The projections of the upper and lower surfaces 862, 864 of the single insert 850 may be in the form of eyebrows 860. In this embodiment, the eyebrows 860 include a substantially smooth and curved surface. In the embodiment shown, torsional stabilizers 870 are also provided substantially medially and laterally on the member 850 projecting superiorly and inferiorly from both the upper and lower surfaces 862, 864, respectively. The torsional stabilizers 870 may include a spiked or pointed projection or extension configured to engage adjacent vertebrae.

FIGS. 11A-11E provide an eleventh embodiment of an implant 900. In general, the structure of implant 900 is similar or comparable to the structure of implant 1. In this embodiment, the inserts 50 have been replaced with a member 950 and the spacer 912 includes multiple components.

The spacer 912 has a first spacer portion 972 and a second spacer portion 974. The first spacer portion 972 has a first end 972a and a second end 972b, and the second spacer portion 974 has a first end 974a and a second end 974b. The second end 972b of the first spacer portion 972 is coupled to the first end 974a of the second spacer portion 974. The first and second spacer portions 972, 974 form the superior surface 942 and the inferior surface 944 of the spacer 912. The superior surface 942 and the inferior surface 944 each have a contact area 922 configured to engage adjacent vertebrae. The first and second spacer portions 972, 974 and the member 950 join to form an opening 916 extending from the superior surface 942 to the inferior surface 944 of the spacer 912.

The first and second spacer portions 972, 974 may be joined together in any suitable manner. For example, the first and second spacer portions 972, 974 may be mated together by a splice joint, scarf joint, butt joint, or the like. The splice joint may include, for example, a half lap splice joint, a bevel lap splice joint, a tabled splice joint, or the like. In particular, the splice joint may include joining two pieces of material together by at least partially overlapping them (e.g., overlapping at least a portion of the first spacer portion 972 and at least a portion of the second spacer portion 974). In the embodiment shown in FIG. 11A, the joint portion between first and second spacer portions 972, 974 is at least partially a half lap splice joint such that the joint does not increase the height of the spacer 912. In a half lap splice joint, material is removed from each of the members so that the resulting joint is the thickness of the two members as combined. Although not shown, the splice joint between the first and second spacer portions 972, 974 may be beveled or scarfed, stepped, notched, keyed, nibbed, or the like. Any type of joint formed between the first and second spacer portions 972, 974 may be further secured with one or more pins 978 or the like.

The member 950 has an upper surface 962, a lower surface 964, a first lateral portion 966, a second lateral portion 968, and at least one hole 934 traversing the member 950 for receiving a fastener, such as a screw 930. The upper surface 962 and/or lower surface 964 may extend a distance beyond the superior surface 942, the inferior surface 944, or both surfaces 942, 944 of the spacer 912. In particular, a portion of member 950 may extend above or below the superior and inferior surfaces 942, 944 of the spacer 912. The projections of the upper and lower surfaces 962, 964 may each be in the form of an eyebrow 960. The eyebrow 960 may include a rounded portion, for example, with a smooth surface. The upper and lower surfaces 962, 964 may further include one or more torsional stabilizers 970 configured to prevent or minimize torsional motion of the implant 900 once implanted. The torsional stabilizers may be positioned, for example, substantially medially and laterally along the length of the member 950. The torsional stabilizers 970 may include a spiked or pointed projection or extension configured to engage adjacent vertebrae.

The member 950 is coupled to the spacer 912 such that the first end 972a of the first spacer portion 972 engages the first lateral portion 966 of the member 950 and the second end 974b of the second spacer portion 974 engages the second lateral portion 968 of the member 950. The spacer portions 972, 974 and the member 950 may also be joined together in any suitable manner. The member 950 may be configured to mirror the shape and design of the spacer 912. The spacer 912 may define at least one recess, projection, etc. sized and dimensioned to retain at least a portion of the member 950. Similar to the insert configurations discussed in this document, member 950 may rest against a portion of the spacer portions 972, 974 or a recess therein to form a joint, such as a lap joint, half lap joint, dovetail lap joint, beveled lap joint or scarf joint, stepped lap joint, tabled lap joint, or the like. In particular, at least a portion of the member 950 may at least partially overlap at least a portion of the spacer 912 or vice versa. In the embodiment shown in FIG. 11A, the joint portions between the member 950 and the spacer 912 are at least partially a half lap joint such that the joint does not increase the height of the spacer 912.

For example, the member 950 may include a first extension 967 extending from the first lateral portion 966 and a second extension (not visible) extending from the second lateral portion 968. The first extension 967 and second extension may extend posteriorly away from a front surface 965 of the member 950 and toward the distal end 946 of the spacer 912 when attached thereto. The first extension 967 may contact a first ledge 973 on the first spacer portion 972 to form a first half lap joint. Similarly, the second extension may contact a second ledge on the second spacer portion 974 to form a second half lap joint. The extensions 967 and ledges 973 may be configured to be complimentary and mate together, for example, with planar surfaces, curved surfaces, tapers, bevels, notches, or the like. Depending on the configuration of the joints, the joints may form a press-fit or friction-fit engagement to secure the member 950 to the spacer 912 or the joints may be further secured, for example, with adhesives, pins 978, or the like. For example, the first and second half lap joints may each be further secured with at least one pin 978.

When present, the pins 978 may traverse at least a portion of the spacer 912 and/or the member 950. For example, the extensions 967 may include one or more openings 980 extending therethrough sized and configured to receive a portion of pin 978 to secure the member 950 to the spacer 912. Similarly, the corresponding portion of the spacer 912 may include one or more openings 980 extending therethrough sized and configured to receive the remainder of pin 978 to secure the member 950 to the spacer 912. These openings 980 may or may not be threaded. The pins 978 may pass through holes 980, for example, in a substantially perpendicular manner relative to a horizontal plane to secure the joints between the member 950 and the spacer 912. For example, the pins 978 may be oriented substantially perpendicular relative to the superior and/or inferior surfaces 942, 944 of the spacer 912. The pins 978 may be in the form of dowels (as shown connecting the first spacer portion 972 to the second spacer portion 974) or may be at least partially threaded (as shown connecting the member 950 to the spacer 912). The pins 978 may be formed from a biocompatible material, such as titanium, or the pins 978 may be formed from tantalum, for example, to enable radiographic visualization.

The implant 900 may also include a locking mechanism 920 disposed on the member 950 for preventing back out of the screws 930. For example, a cam-style blocking mechanism may be used with screws 930 that capture the fixation device screws 930 once they are inserted fully through the member 950. As shown, the anti-back out mechanism 920 may include a single set screw 932 that retain the screws 930 with the implant 900, although any suitable anti-back out mechanism 920 may be selected by one of ordinary skill in the art.

FIGS. 12A-12E provide a twelfth embodiment of an implant 1000. In general, most of the structure of implant 1000 is similar or comparable to the structure of implant 1. In addition, this embodiment is substantially the same as the implant 900 discussed above, and the discussion for implant 900 applies equally here with the same reference numbers provided for unchanged elements. In this particular embodiment, the first and second spacer portions 1072, 1074 are connected together by a connector 1084 instead of being attached directly to one another. This allows the first and second spacer 1072, 1074 to be spaced apart with respect to one another. The connector 1084 may also be formed of a material different from the spacer portions 1072, 1074, for example, to allow for strength, support, radiographic visualization, or the like.

The first and second spacer portions 1072, 1074 may be secured together with one or more connectors 1084. The connector 1084 may be sized, shaped, and configured in any suitable manner to join the second end 1072b of the first spacer portion 1072 to the first end 1074a of the second spacer portion 1074. Any of the joints discussed in this document may be suitable to join the first and second spacer portions 1072, 1074 using connector 1084.

Figure 12A:
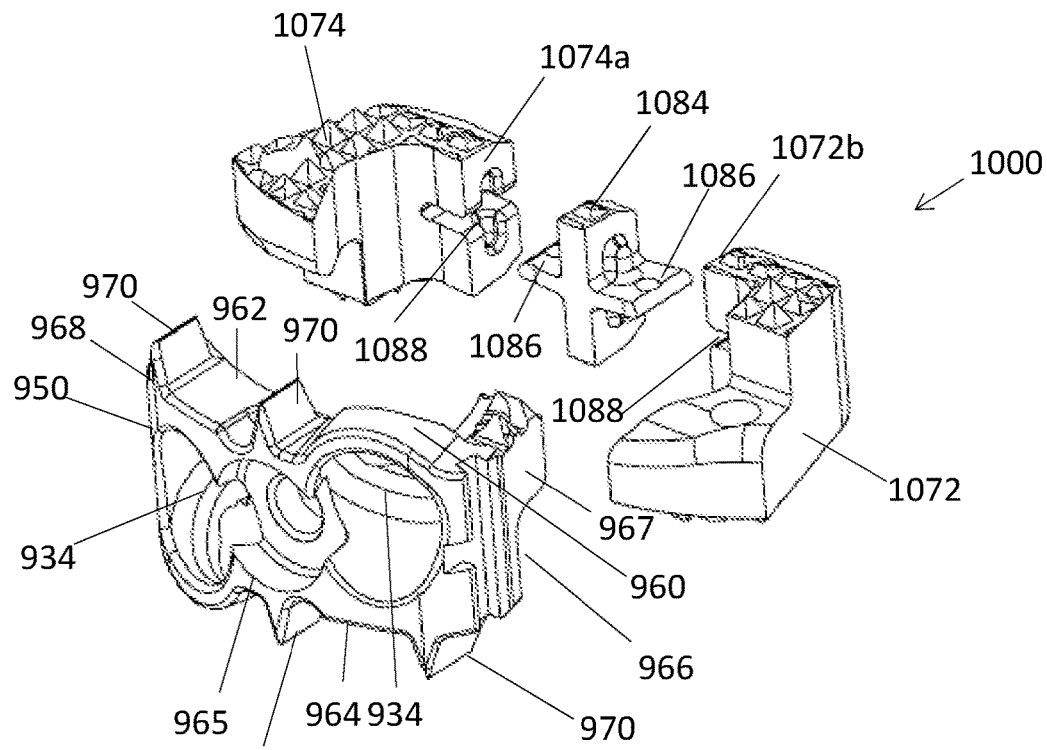
FIG. 12A shows an exploded view of a twelfth embodiment where the two-part spacer is joined by a connecting member.
Figure 12B:
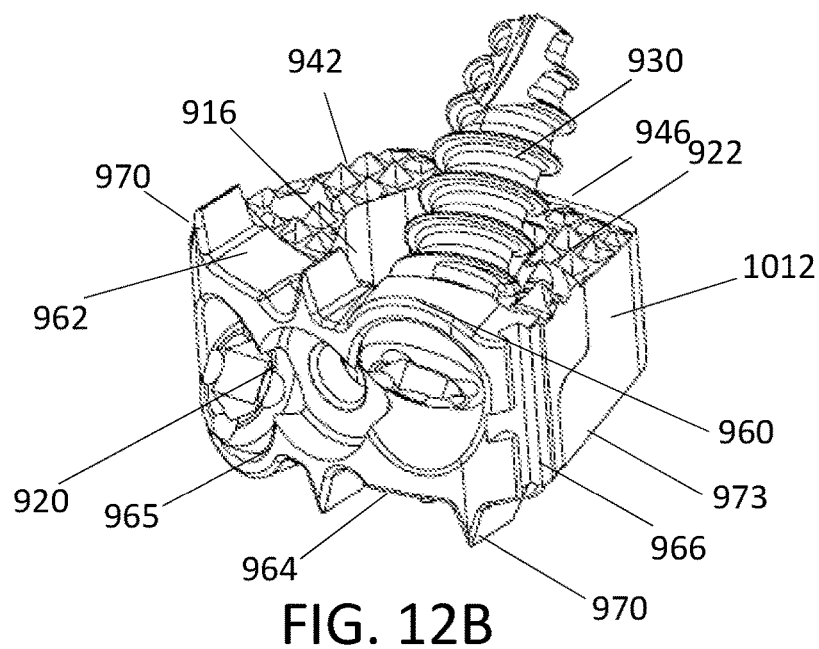
FIG. 12B shows a perspective view of the embodiment shown in FIG. 12A.
Figure 12C:
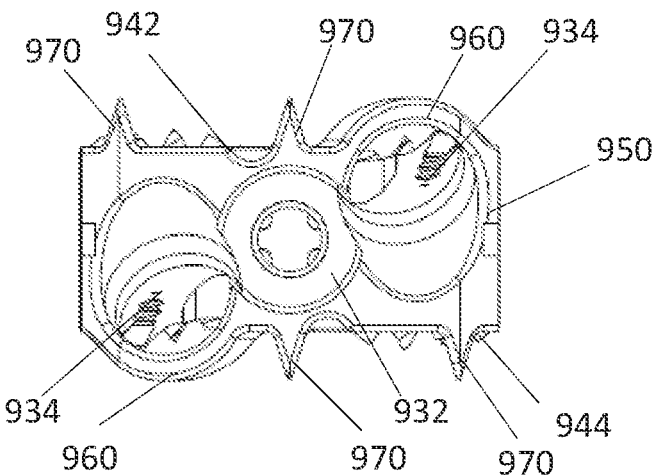
FIG. 12C is a front view of the embodiment shown in FIG. 12A.
Figure 12D:
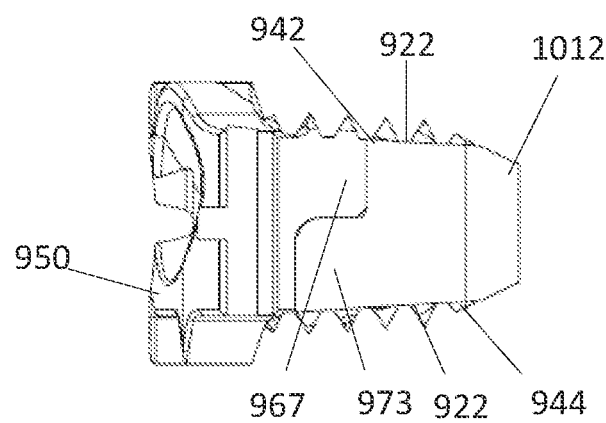
FIG. 12D is a lateral view of the embodiment shown in FIG. 12A.
Figure 12E:
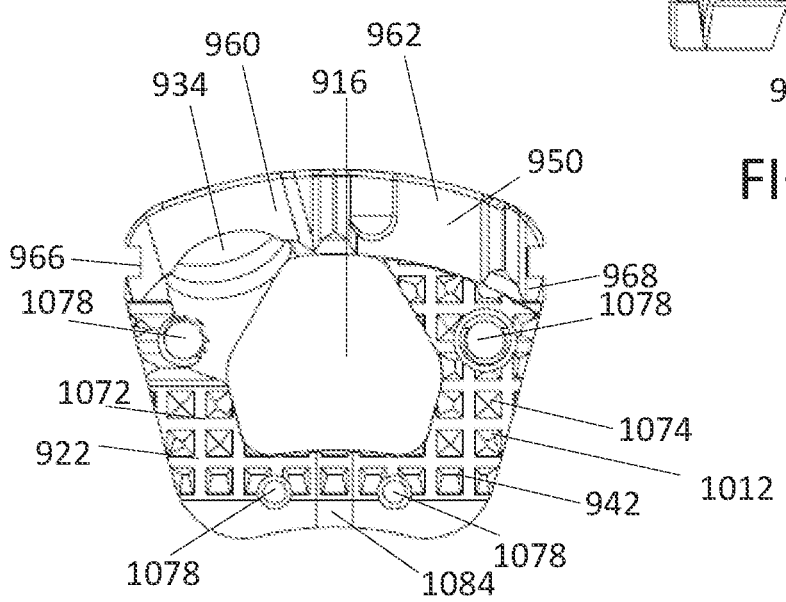
FIG. 12E is a top view of the embodiment shown in FIG. 12A.

In the embodiment depicted in FIG. 12A, the connector 1084 has a substantially t-shaped, plus-shaped, or cross-shaped configuration. For example, the connector 1084 may include at least first and second tenons 1086 sized and configured to be received within mortises 1088 in the spacer portions 1072, 1074. For example, a first tenon 1086 projecting laterally from the connector 1084 may be size and configured to be received within a first mortise 1088 in the second end 1072b of the first spacer portion 1072 and the second tenon 1086 projecting laterally in the other direction from the connector 1084 may be sized and configured to be received with the second mortise 1088 in the first end 1074a of the second spacer portion 1074.

The tenons 1086 may include additional superior and inferior projections, for example, which mate with a substantially t-shaped, plus-shaped, or cross-shaped mortise 1088. The mortise and tenon configuration may be of any suitable size, shape, and dimension to join the connector 1084 to the respective spacer portions 1072, 1074. As in the other embodiments, the joint may be further secured with one or more pins 1078. In particular, the pins 1078 may be positioned through each of the tenons 1086 to affix the connector 1084 to the respective spacer portions 1072, 1074. The pins 1078 may be positioned through openings 1080 in the tenons 1086 and corresponding openings 1080 in the spacer portions 1072, 1074.

According to a thirteenth embodiment shown in FIGS. 13A-13G, a single piece or unitary implant 1100 is provided with an anterior portion 1150 and a spacer portion 1112. Certain features of implant 1100 are similar or comparable to the structure of implant 1. In this embodiment, the inserts 50 have been replaced with an anterior portion 1150, and the spacer 1112 and the anterior portion 1150 form a one piece, standalone design.

The spacer 1112 has a superior surface 1142, an inferior surface 1144, a distal end 1146, a proximal end 1148, and first and second lateral sides 1136, 1138. The superior surface 1142 and the inferior surface 1144 each have a contact area 1122 configured to engage adjacent vertebrae.

The contact areas 1122 may include one or more protrusions 1113 on the superior and inferior surfaces 1142, 1144 of each implant 1100 designed to grip the endplates of the adjacent vertebrae, resist migration, and aid in expulsion resistance. The plurality of protrusions 1113 may be pyramidal in shape and may form a series of ridges and grooves (as shown), but the protrusions 1113 can be configured to be any size or shape to enhance anchoring the spacer 1112 and the implant 1100 to each of the adjacent vertebrae.

The spacer 1112 defines an opening 1116 extending from the superior surface 1142 to the inferior surface 1144 of the spacer 1112 configured to receive bone graft materials. The spacer also defines openings 1117 extending through the lateral sides 1136, 1138 and into to the opening 1116. These lateral openings 1117 may be in fluid communication with the central opening 1116. These openings 1117 may be configured to allow for compression and expansion of the superior and inferior portions of the spacer 1112.

The distal end 1146 of the spacer 1112 may include a leading taper 1140 for ease of insertion into the disc space. The leading taper 1140 may be in the form of a chamfer or a bevel which enables self-distraction of the vertebral bodies during insertion of the implant 1100. The leading taper 1140 may be located along the insertion direction of the implant 100. For example, the leading taper 1140 may assist in an anterior approach to the disc space. The distal end 1146 may also include a groove or recess extending between the lateral sides 1136, 1138 to facilitate compression and expansion of the implant 1100.

The anterior portion 1150 has an upper surface 1162, a lower surface 1164, a first lateral portion 1166, a second lateral portion 1168, and at least one hole 1134 traversing the anterior portion 1150 for receiving a fastener, such as a screw 1130. At least a portion of the upper surface 1162 or the lower surface 1164 of the anterior portion 1150 extends beyond the superior surface 1142 or the inferior surface 1144 of the spacer 1112. The projections of upper surface 1162 and/or lower surface 1164 may be in the form of an eyebrow 1160. The eyebrow 1160 may include a rounded portion having a smooth surface. The upper surface 1162 and/or lower surface 1164 may further include one or more torsional stabilizers 1170 configured to prevent or minimize torsional motion of the implant 1100 once implanted. The torsional stabilizer 1170 may include a spiked or pointed projection or extension, for example, positioned medially and/or laterally on the anterior portion 1150.

Figure 13A:
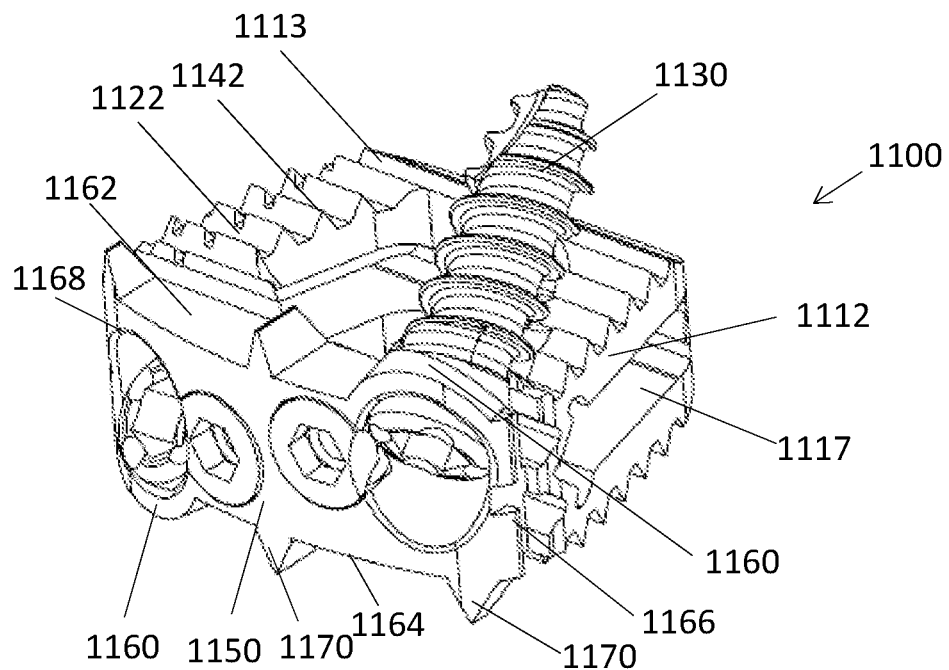
FIG. 13A is a perspective view from an anterior position of a thirteenth embodiment of a single piece implant having an anterior portion and a spacer portion.
Figure 13B:
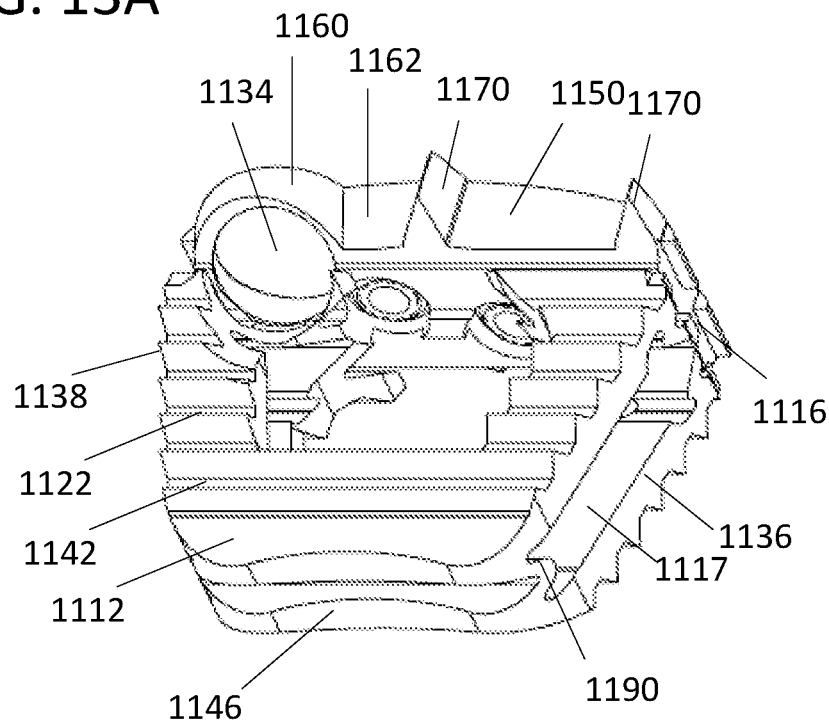
FIG. 13B is another perspective view from a posterior position of the embodiment shown in FIG. 13A.
Figure 13C:
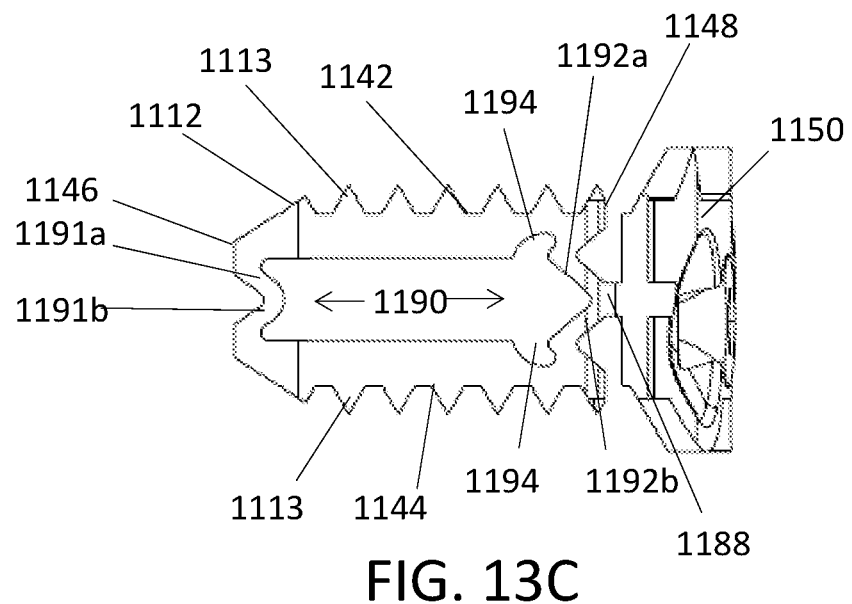
FIG. 13C is a lateral view of the embodiment shown in FIG. 13A.
Figure 13D:
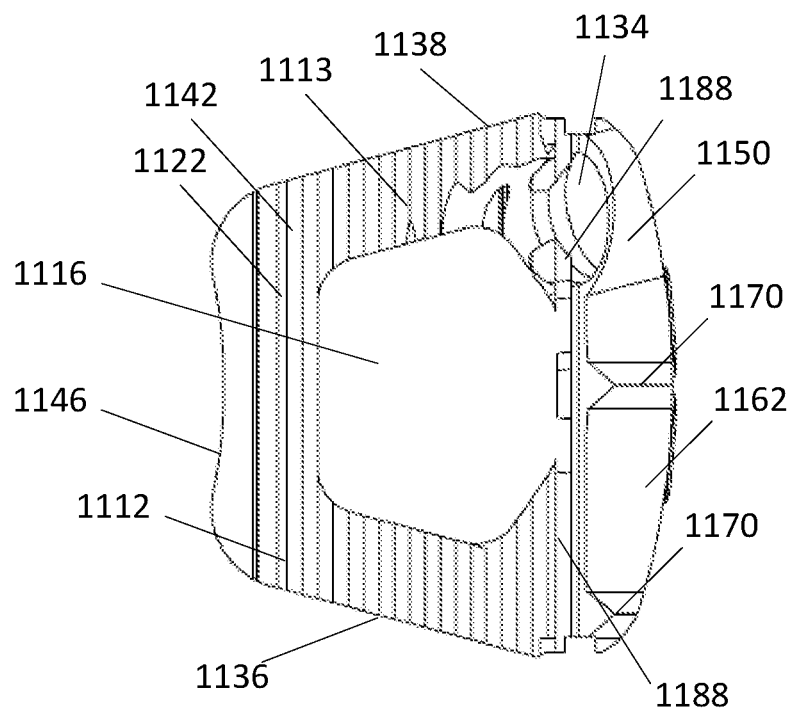
FIG. 13D is a top view of the embodiment shown in FIG. 13A.
Figure 13E:
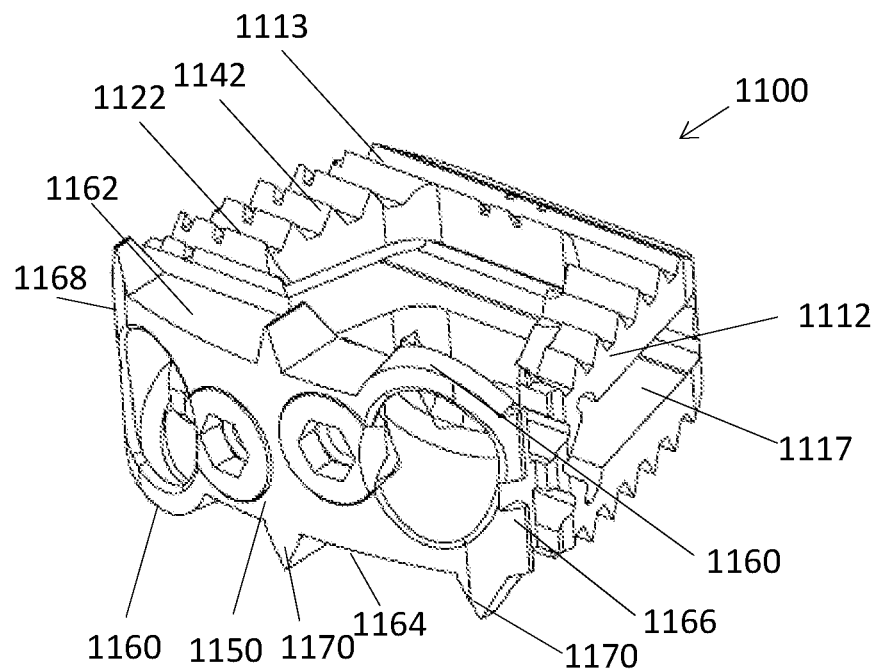
FIG. 13E is another perspective view of the embodiment shown in FIG. 13A.
Figure 13F:
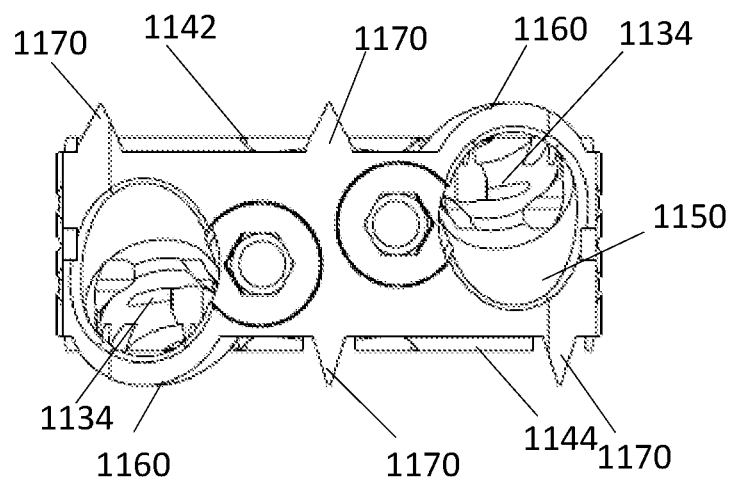
FIG. 13F is a front view of the embodiment shown in FIG. 13A.
Figure 13G:
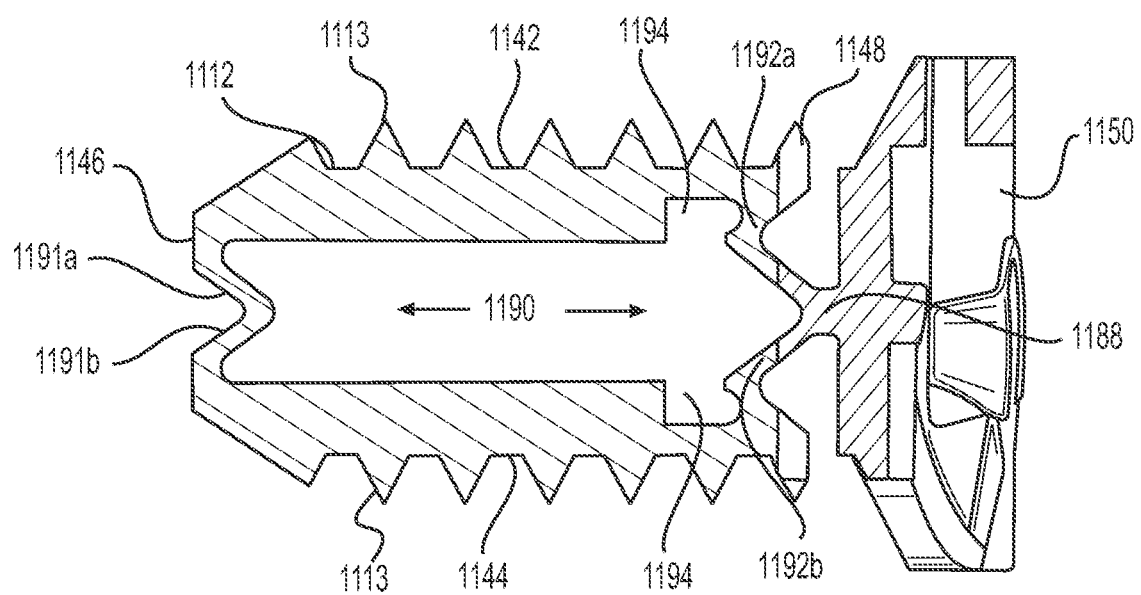
FIG. 13G is an alternative version of the embodiment shown in FIG. 13A.

The anterior portion 1150 extends from the proximal end 1148 of the spacer 1112 such that the anterior portion 1150 and the spacer 1112 are a single piece. As a single, unitary piece the anterior portion 1150 and the spacer 1112 may be formed from a single piece of material, such as titanium. By way of example as shown in FIGS. 13C and 13D, at least one beam 1188 may connect the anterior portion 1150 to the proximal end 1148 of the spacer 1112 to form a unitary piece. The beam 1118 may extend from a substantially medial position to a lateral position of the spacer 11112. The beam 1118 may extend across the entire width of the spacer 1112 or a portion thereof. The beam 1118 may be interrupted by a gap, for example, positioned substantially medially. No additional fixation devices or mechanisms are required to attach the anterior portion 1150 to the spacer portion 1112, but any suitable fixation systems may be selected by one of ordinary skill in the art.

The spacer 1112 includes one or more spring features 1190, for example, to allow for compression and/or expansion of the implant 1100. Thus, the spacer 1112 has a flexible nature with flexible sections or portions. In particular, the spring features 1190 are designed such that the spacer 1112 is able to mimic the properties of bone and/or PEEK especially when implanted between adjacent vertebrae. For example, the modulus of elasticity for bone, depending on the type, temperature, strain rate, and other factors, may range from about 0.5-25 GPa. In particular, cancellous bone has a modulus of elasticity of about 0.5-5 GPa. The Young's modulus of PEEK is about 3-4 GPa. Thus, PEEK is often used due to its bone-like modulus of elasticity. A solid block of titanium, on the other hand, has a much higher modulus of about 100-110 GPa. As a replacement to traditional PEEK implants, implant 1100 is provided with spring-like features 1190 such that the implant 1100, even when formed of titanium, can emulate the modulus of elasticity of cancellous bone. For example, the spacer 1112 may provide for a modulus of elasticity of about 0.5-5 GPa, about 1-5 GPa, about 2-5 GPa, or about 3-4 GPa for the implant 1100.

The spacer 1112 may provide for additional flexibility and an additional range of motion with respect to the two adjacent vertebrae. For example, the spacer 1112 may allow for at least two degrees of motion depending upon the direction and location of the applied force. In particular, the implant 1100 may allow for forward/anterior or aft/posterior bending and lateral bending to the left or right sides. This type of motion and flexibility may allow for more natural movement of the spinal column.

The spring features 1190 may be of any suitable design or configuration to provide compression and/or expansion of superior and inferior surfaces 1142, 1144 of the spacer 1112. For example, the spring feature 1190 may be in the form of a cantilevered v-spring having an elongated solid spring member with a cross-sectional configuration in the form of a V. As shown, the distal end 1146 of the spacer 1112 may have a first spring feature 1190. For example, the first spring feature 1190 may be in the form of a first v-spring. In addition, the proximal end 1148 of the spacer 1112 may include a second spring feature 1190. The second spring feature 1190 may also be in the form of a second v-spring. The first and second spring features 1190 may be the same or different. The first and second spring features 1190 may be configured such that the spacer 1112 simulates the modulus of elasticity of bone even when the spacer 1112 and the anterior portion 1150 are comprised of titanium or a titanium alloy.

As shown in FIG. 13C, the first spring feature 1190 on the distal end 1136 may include two longitudinal walls 1191a, 1191b provided with an angle therebetween. The angle between the two longitudinal walls 1191a, 1191b of the v-spring may range from about 45°-170°, about 60°-150°, about 80°-130°, or about 70°-100°, for example. The distal portions of the two longitudinal walls 1191a, 1191b may be anchored to the superior and inferior portions of the spacer 1112 by additional v-spring configurations. For example, the first longitudinal wall 1191a may interface with the superior portion of the spacer 1112 by a v-spring, which is inverted relative to the v-spring provided between the first and second longitudinal walls 1191a, 1191b. Similarly, the second longitudinal wall 1191b may interface with the inferior portion of the spacer 1112 by another v-spring, which is inverted relative to the v-spring provided between the first and second longitudinal walls 1191a, 1191b. Thus, the first spring feature 1190 provided on the distal end 1136 may include a zig-zag of three v-springs oriented in opposite directions. The angle of the v-spring between the first and second longitudinal walls 1191a, 1191b may be greater than the angles connecting the respectively longitudinal walls 1191a, 1191b to the superior and inferior portions of the spacer 1112.

The implant 1100 may include a second spring feature 1190 on the proximal end 1148 of the spacer 1112. The second spring feature 1190 may also include two longitudinal walls 1192a, 1192b provided with an angle therebetween. The angle between the two longitudinal walls 1192a, 1192b of the v-spring may again range from about 45°-170°, about 60°-150°, about 80°-130°, or about 70°-100°, for example. This angle may be the same, larger, or smaller than the angle between the first and second longitudinal walls 1191a, 1191b at the distal end 1136. The apex of the angle may form a junction to connect with the beam 1188, which connects the spacer portion 1112 to the anterior portion 1150.

The distal portions of the two longitudinal walls 1192a, 1192b may be anchored to the superior and inferior portions of the spacer 1112, respectively by additional v-spring configurations. For example, the first longitudinal wall 1192a may interface with the superior portion of the spacer 1112 by a v-spring, which is inverted relative to the v-spring provided between the first and second longitudinal walls 1192a, 1192b. Similarly, the second longitudinal wall 1192b may interface with the inferior portion of the spacer 1112 by another v-spring, which is inverted relative to the v-spring provided between the first and second longitudinal walls 1192a, 1192b. Thus, the second spring feature 1190 provided on the proximal end 1148 may include a zig-zag of three v-springs oriented in opposite directions. The angle of the v-spring between the first and second longitudinal walls 1192a, 1192b may be the same or greater than the angles connecting the respectively longitudinal walls 1192a, 1192b to the superior and inferior portions of the spacer 1112. Additional recesses 1194 may be provided on the superior and inferior portions of the spacer 1112 to allow for proper movement of the v-springs. In particular, the recesses 1194 may be formed such that the apexes of the upper and lower v-portions are revealed. As shown in FIG. 13C, the recesses 1194 may be rounded or curved. In an alternative embodiment shown in FIG. 13G, the recesses 1194 may be angled or pointed.

Although a v-shaped spring is exemplified in this embodiment, the spring portions 1190 may be formed in any suitable shape or configuration not limited to the v-shape, and may include, for example, U-shape, S-shape, coiled, square, rectangular, sinusoidal, corrugated and accordion pleated. In addition, the shape of the spring features 1190 may be symmetrical or non-symmetrical. For example, the longitudinal walls 1191a, 1191b, 1192a, 1192b may be symmetrical or non-symmetrical with respect to one another.

According to a fourteenth embodiment, FIGS. 14A-14E show an implant 1200, which may be particularly suitable for use with an anterior lumbar procedure. In general, most of the structure of implant 1200 is similar or comparable to the structure of implant 200 shown in FIGS. 4A-4E. In this particular embodiment, two inserts 1250 provide the fastener apertures 1234. Instead of a center insert, the third fastener aperture 1234 is provided directly through a center portion of the spacer 1212.

Figure 14A:
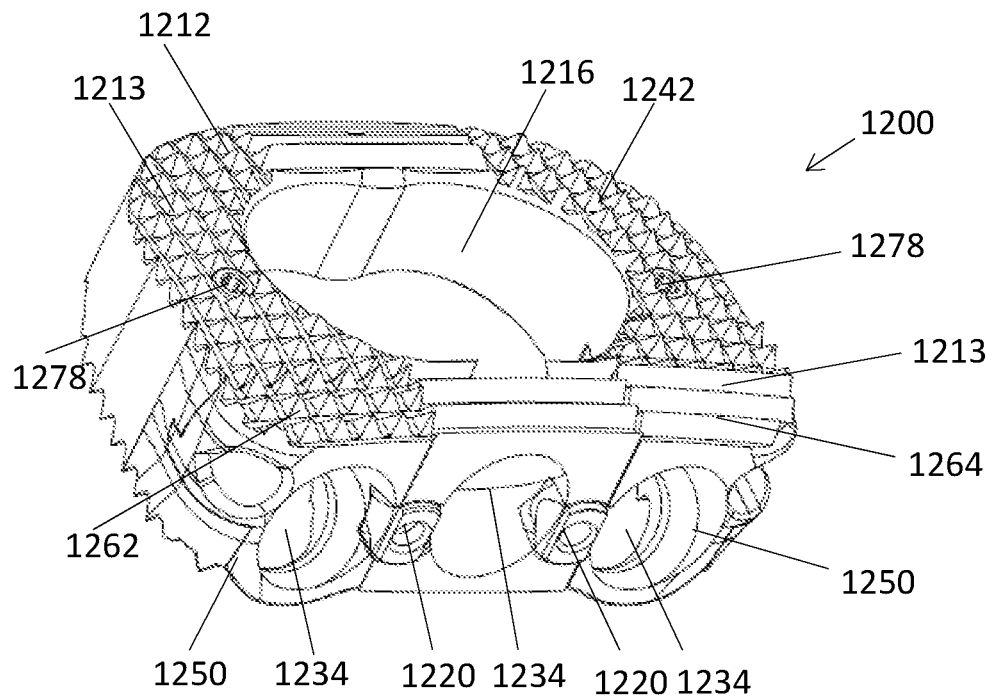
FIG. 14A is a perspective view of a fourteenth embodiment including inserts.
Figure 14B:
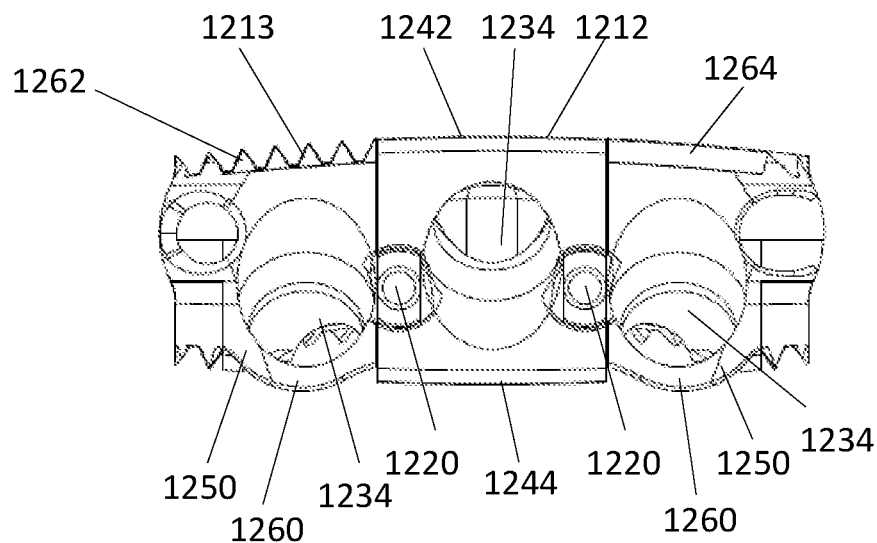
FIG. 14B is a front view of the embodiment shown in FIG. 14A.
Figure 14C:
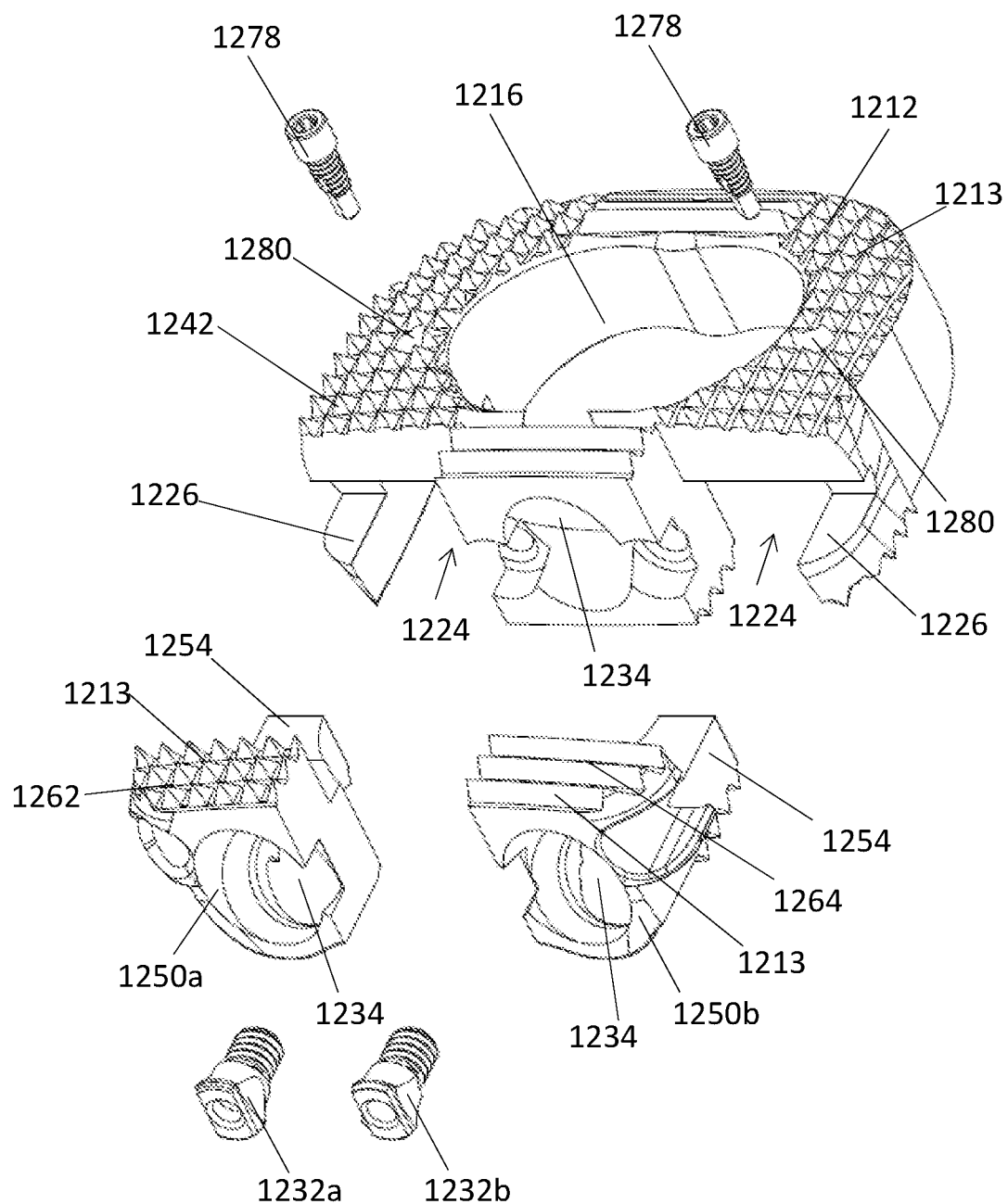
FIG. 14C is an exploded view of the embodiment shown in FIG. 14A.

As shown in FIG. 14C, a first insert 1250a is identical to a second insert 1250b except as mirror images of one another to fit the respective cutouts 1224 in the spacer 1212. The first and second inserts 1250a, 1250b each define a fastener aperture 1234. The first and second inserts 1250a, 1250b are each configured to allow a fastener, such as a bone screw (not shown but similar to the other fasteners or bone screws described in this document) to engage superior or inferior vertebra. In the embodiment shown, the fastener apertures 1234 in the first and second inserts 1250a, 1250b allow for engagement with the inferior vertebra. A third fastener aperture 1234 is provided centrally in the spacer 1212 to allow for a fastener to engage the superior vertebra.

Similar to implant 200, the spacer 1212 may include one or more cutouts 1224 sized and configured to retain the inserts 1250. The cutouts 1224 may be in fluid communication with the opening 1216 extending from the superior surface 1242 to the inferior surface 1244 of the spacer 1212. In addition, the cutouts 1224 may extend to the superior surface 1242 and/or inferior surface 1244 of the spacer 1212. The cutouts 1224 may further define a projection 1226 extending from the lateral sides of the spacer 1212 configured to mate with the arm 1254 of the insert 1250. The arms 1254 may be sized and configured to be recessed to fit between a center portion of the spacer 1212 and the projection 1226.

The inserts 1250 may be coupled, removably coupled, connected, or attached to the spacer 1212 in any suitable manner known in the art. For example, portions of the insert 1250 may be assembled to the spacer 1212 using, alone or in combination, a friction fit, a dovetail assembly, dowel pins, hooks, staples, screws, adhesives, and the like, or any suitable fasteners known in the art. For example, the inserts 1250 may be secured to the spacer 1212 with pins 1278 which traverse at least a portion of the spacer 1212 and/or the insert 1250. For example, the arm 1254 may include one or more openings (not shown) extending therethrough sized and configured to receive a portion of pin 1278. Similarly, the corresponding portion of the spacer 1212 may include one or more openings 1280 extending therethrough sized and configured to receive the remainder of pin 1278. The pins 1278 may be in the form of dowels or may be fully or partially threaded, for example. The pins 1278 may be formed from a biocompatible material, such as titanium, or the pins 1278 may be formed from tantalum, for example, to enable radiographic visualization.

Figure 14D:
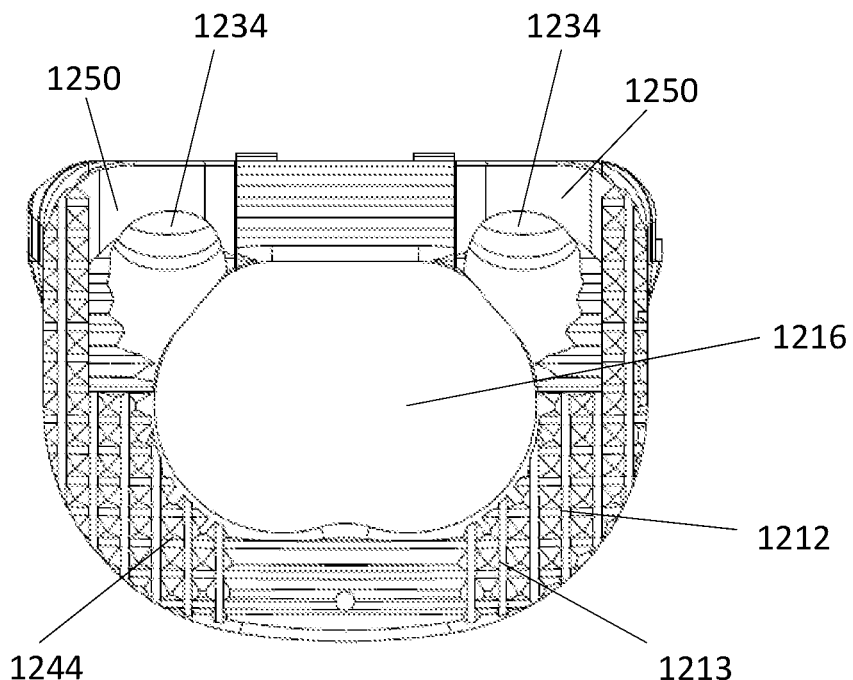
FIG. 14D is a bottom view of the embodiment shown in FIG. 14A.
Figure 14E:
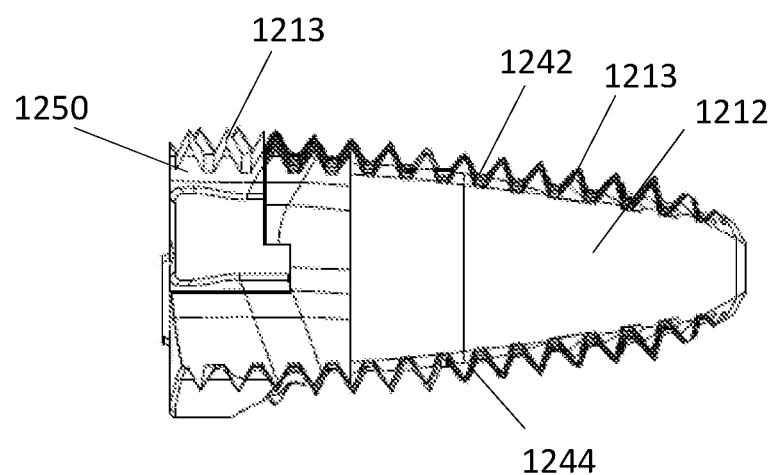
FIG. 14E is a lateral view of the embodiment shown in FIG. 14A.

In order to engage the adjacent vertebrae, the spacer 1212 may include a plurality of protrusions 1213 on the superior and/or inferior surfaces 1242, 1244. The protrusions 1213 on the superior and inferior surfaces 1242, 1244 of each implant 1200 grip the endplates of the adjacent vertebrae, resist migration, and aid in expulsion resistance. A portion of the plurality of protrusions 1213 may be pyramidal in shape and a portion of the plurality of protrusions 1213 may be a series of sequential ridges or grooves. As shown in FIG. 14D, ridges or grooves may be positioned centrally on the anterior and posterior portions of the superior and/or inferior surfaces 1242, 1244. The pyramidal protrusions 1213 may surround the central opening 1216 in the locations where the ridges or grooves are not present. Although the protrusions 1213 are depicted in a certain configuration, protrusions 1213 can be configured to be any size or shape and in any configuration to enhance anchoring of the implant 1200 to the adjacent vertebrae.

A portion of the upper and/or lower surface 1262, 1264 of the insert 1250 including the plurality of protrusions 1213 may form a continuous and contiguous superior surface 1242 and/or inferior surface 1244 for the implant 1200. Although the first insert 1250a is depicted with a plurality of projections 1213 which are pyramidal in shape and the second insert 1250b is depicted with a plurality of ridges and grooves, these surface features may be the same or different on the first and second inserts 1250a, 1250b. In alternative to pyramidal projections or ridges, smooth surfaces, textured surfaces, torsional stabilizers, or the like configured to enhance anchoring of the implant 1200 to adjacent vertebrae may be provided. The inserts 1250 may also include an eyebrow 1260. The eyebrows 1260 may fully capture the bone screws while still allowing for the screw to reside about, below, or above the base plane of the superior and inferior surfaces 1242, 1244. As shown in FIG. 14B, the inserts 1250 may include eyebrows 1260 projecting below the inferior surface 1244 of the spacer 1212.

The fastener apertures 1234 may be configured such that the locking mechanisms 1220 may block or unblock the heads of the fasteners when positioned within the respective fastener apertures 1234. As shown in FIG. 14C, the anti-back out mechanisms 1220 may include a first set screw 1232a that is configured to block a portion of the fastener in the first insert 1250a and the fastener in the fastener aperture 1234 through the spacer 1212 and a second set screw 1232b that is configured to block a portion of the fastener in the second insert 1250b and the fastener in the fastener aperture 1234 through the spacer 1212.

Figure 15A:
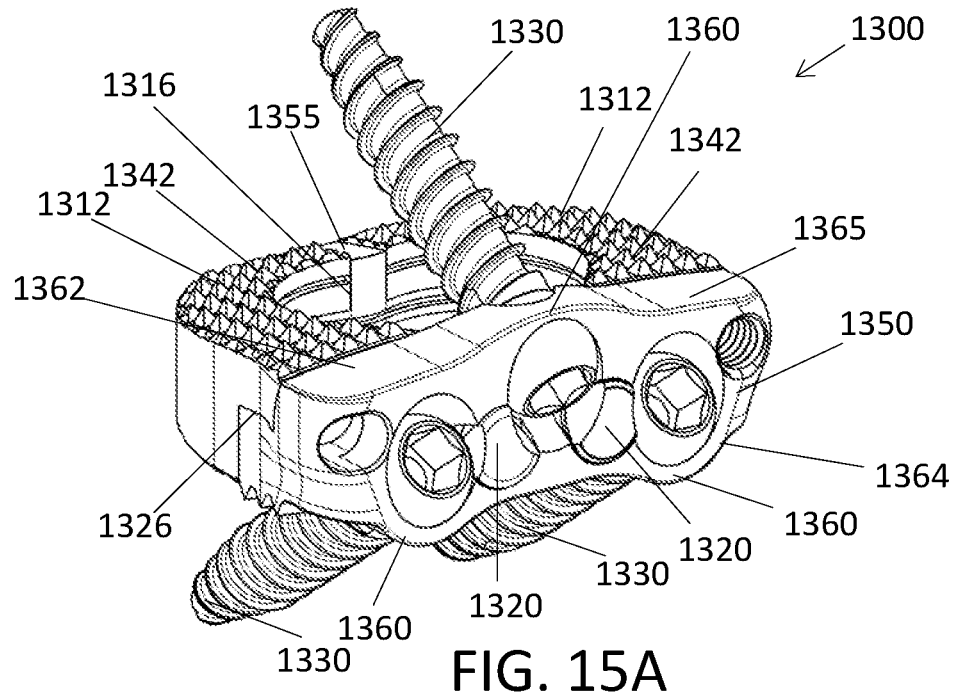
FIG. 15A is a perspective view of a fifteenth embodiment of a frame with endplates suitable for use in anterior lumbar procedures.
Figure 15B:
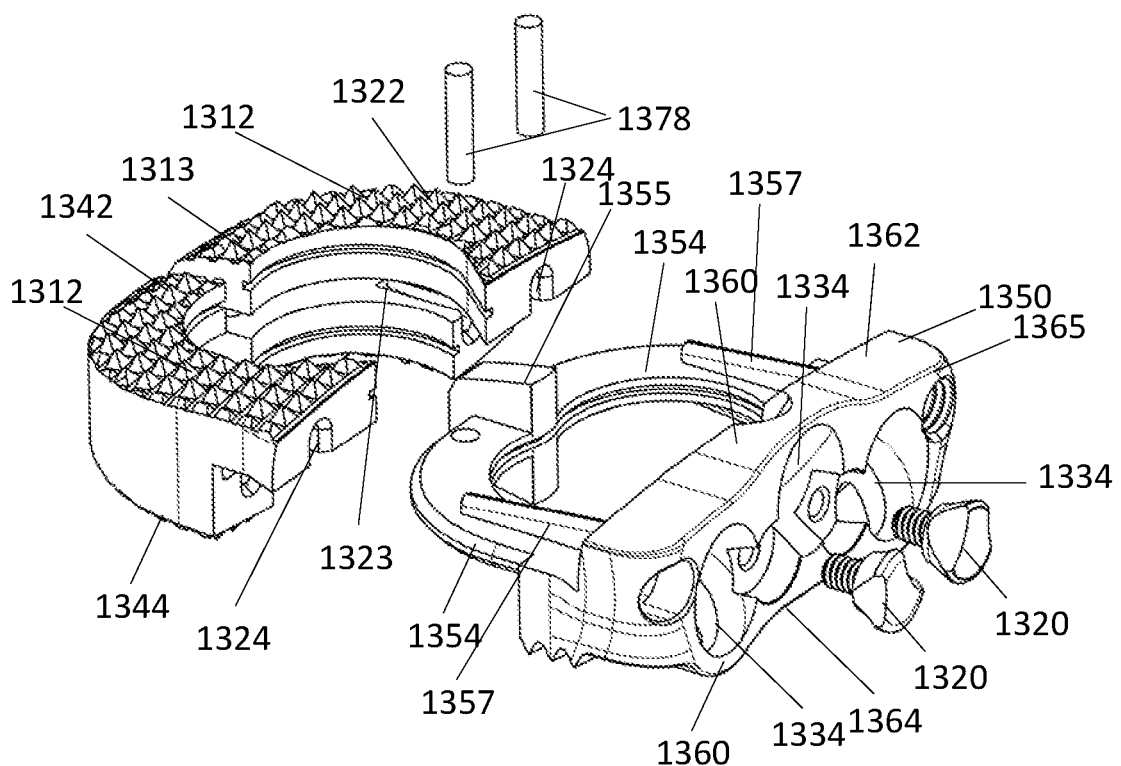
FIG. 15B is an exploded view of the embodiment shown in FIG. 15A.

According to a fifteenth embodiment shown in FIGS. 15A and 15B, which may be particularly suitable for an anterior lumbar procedure, an implant 1300 including a frame 1350 with a plurality of endplates 1312 is provided. As shown in FIG. 15B, the frame 1350 may be substantially in the form of a ring or loop of material with a central opening. When combined with the endplates 1312, which may be shaped and configured to match the central opening in the frame 1350, the opening may provide for a graft opening area 1316 configured to provide the maximum amount of volume for bone graft packing. The graft area 1316 may be configured for receiving bone graft material, for example, to promote fusion of the adjacent vertebral bodies.

The frame 1350 may include a front portion 1365 having an upper surface 1362 and a lower surface 1364. A first arm 1354 may extend from a first end of the frame 1350 and a second arm 1354 may extend from a second end of the frame 1350. The arms 1354 may join together to form the ring-like structure. The frame 1350 may also include a rear portion 1355. The arms 1354 may meet at the rear portion 1355 of the frame 1350, for example. The front portion 1365 and the rear portion 1355 may have a height greater than the height of the arms 1350. In particular, the rear portion 1355 of the frame 1350 may extend a distance above and below the ring portion of the frame 1350. Although the rear portion 1350 is shown centrally located, it is envisioned that the rear portion 1350 may be offset or positioned at any suitable location along the circumference of the ring.

One or more endplates 1312 are positioned on and affixed to the frame 1350 such that at least a portion of the ring portion of the frame 1350 is covered or housed within the endplates 1312. As shown in FIG. 15B, the endplates 1312 may have c-shaped configurations designed to follow the shape of the ring of the frame 1350. As shown, two separate endplates 1312 are affixed to the arms 1354 of the frame 1350 with the rear portion 1355 separating the endplates 1312 from one another. The endplates 1312 each include a recess or channel 1323 designed and configured to retain at least a portion of the ring and, in particular, the arms 1354 of the frame 1350. In addition, a secondary recess 1324 may be defined within at least one end of each of the endplates 1312 such that a corresponding protrusion 1357 extending from the arms 1345 may be received in the recesses 1324 to aid in securing the endplates 1312 to the frame 1350. In particular, the protrusions 1357 may extend superiorly from the arms 1345 and may be angled such that the protrusions 1357 have a greatest height proximate to the front portion 1365 to enable the endplates 1312 to slide onto the frame 1350. The endplates 1312 may also be secured to the frame 1350 with one or more pins 1378. Any suitable number, type, and location for the pins 1378 may be selected. For example, two pins 1378 may be positioned within openings located adjacent to and on opposite sides of the rear portion 1355 of the frame 1350 to secure the endplates 1312.

The endplates 1312 may also define at least one recess, projection, etc. sized and dimensioned to retain a corresponding feature of at least a portion of the frame 1350. For example, a stepped joint 1326 may be provided to connect an end of the endplate 1312 to the frame 1350. In particular, the front portion 1365 or any portion of the frame 1350 may rest against a portion of the endplates 1312 or a recess formed therein to provide a joint, such as a lap joint, half lap joint, dovetail lap joint, beveled lap joint or scarf joint, stepped lap joint, tabled lap joint, or the like. In particular, a lap joint may include joining two pieces of material together by at least partially overlapping them (e.g., at least a portion of the endplate 1312 and the frame 1350 are overlapped). In the embodiment shown in FIG. 15A, the joint portion between the endplate 1312 and the frame 1350 is at least partially a half lap joint such that the joint does not increase the height of the implant 1300. As shown, the endplates 1312 may join the frame 1350 with a stepped lap joint 1326. A portion of the frame 1350 may be stepped with a male projection to mate with a stepped female configuration of the endplate 1312 or vice versa. A series of offset planar surfaces having a rise and a run may form the stepped profile.

The endplates 1312 each include a superior surface 1342 and an inferior surface 1344. The superior and inferior surfaces 1342, 1344 each have a contact area 1322 configured to contact and engage adjacent vertebrae (not shown). The superior and inferior surfaces 1342, 1344 may be parallel, curved, or angled to help restore or recreate a lordosis angle (or other angle) of the human spine. In addition, the superior and/or inferior surfaces 1342, 1344 may be contoured to conform more closely to the concave endplates of the adjacent vertebra.

In order to engage the adjacent vertebrae, the endplates 1312 may include a plurality of protrusions 1313 or teeth on the contact areas 1322 of the superior and/or inferior surfaces 1342, 1344. The protrusions 1313 on the superior and inferior surfaces 1342, 1344 of each implant 1300 grip the endplates of the adjacent vertebrae, resist migration, and aid in expulsion resistance. The plurality of protrusions 1313 may be pyramidal in shape, but the protrusions 1313 can be configured to be any size or shape to enhance anchoring of the implant 1300 to each of the adjacent vertebrae.

In this embodiment, the frame 1350 provides three fastener apertures 1334 to secure fasteners, such as bone screws 1330, in both the superior and inferior vertebrae. For example, the fastener apertures 1334 may extend through the front portion 1365 of the frame 1350 at an angle. A portion of the upper and/or lower surfaces 1362, 1364 of the frame 1350 may extend a distance beyond the superior surface 1342, the inferior surface 1344, or both surfaces 1342, 1344 of the endplates 1312. The projections of the upper and lower surfaces 1362, 1364 of the frame 1350 may be in the form of eyebrows 1360. In this embodiment, the eyebrows 1360 include a substantially smooth and curved surface. In addition, one or more locking mechanisms 1320 may be provided to block or unblock the heads of the fasteners or screws 1330 when positioned within the respective fastener apertures 1334. The anti-back out mechanism 1320 may include set screws configured to block a portion of the screw or screws 1330 positioned through the frame 1350.

FIGS. 16A-16C depict a sixteenth embodiment of an implant 1400. In general, most of the structure of implant 1400 is similar or comparable to the structure of implant 1300 discussed above. Instead of securing the endplates 1412 to the frame 1450 only with pins 1478, however, posts 1459 projecting from the ring are sized and configured to be received within corresponding openings extending through the endplates 1412. In addition, the pins 1478 are positioned proximate to the front portion 1465 of the frame 1450 to further secure the endplates 1412.

As shown in FIG. 16C, the frame 1450 may be substantially in the form of a ring or loop of material with a central opening. The frame 1450 includes front portion 1465 and arms 1454 extending, for example, orthogonally, from first and second ends of the front portion 1465. The arms 1454 join together at the rear portion 1455 to form the ring-like structure. The endplates 1412 are positioned on and affixed to the frame 1450 such that at least a portion of the ring portion of the frame 1450 is covered or housed within the endplates 1412. The endplates 1412 are affixed to the arms 1454 of the frame 1450 with the rear portion 1455 separating the endplates 1412. In this embodiment, the rear portion 1455 may be curved and slightly recessed below the endplates 1412.

The endplates 1412 are affixed to the arms 1454 of the frame 1450. The endplates 1412 include a recess or channel 1423 designed and configured to retain at least a portion of the ring and, in particular, the arms 1454 of the frame 1450. In addition, at least one secondary opening or recess 1424 may be defined within at least one end of each of the endplates 1412 such that corresponding posts 1459 extending from the arms 1454 may be received in the recesses 1424 to aid in securing the endplates 1412 to the frame 1450. As shown, one or more posts 1459 may extend outwardly from the arms 1454 to affix the endplates 1412 to the frame 1450. The posts 1459 may be provided to secure a first end of the endplates 1412. In the embodiment depicted, the posts 1459 and corresponding openings 1424 are substantially squared, but the posts 1459 may be of any suitable shape and dimension. In addition, pins 1478 are positioned proximate to the front portion 1465 of the frame 1450. The pins may be provided to secure a second end of the endplates 1412. It is contemplated that any suitable number, type, and location for the posts 1459 and pins 1478 may be selected to secure the endplates 1412 to the frame 1450.

The endplates 1412 may also define at least one recess, projection, etc. sized and dimensioned to retain a corresponding feature of at least a portion of the frame 1450. For example, a stepped joint 1426 may be provided. In the embodiment shown in FIG. 16A, the endplates 1412 may join the frame 1450 with a stepped lap joint 1426 to connect an end of the endplate 1412 to the frame 1450. A series of offset planar surfaces having a rise and a run may form the stepped profile. In addition, at least one angled surface may be provided in the stepped profile as shown in FIG. 16A.

The other features discussed for the embodiment shown in FIGS. 15A and 15B for implant 1300 are substantially the same for implant 1400 including contact area 1422 on the superior and inferior surfaces 1442, 1444, the protrusions 1413, graft opening 1416, the fastener apertures 1434, and locking or anti-back out mechanisms 1420.

FIGS. 17A-17C depict a seventeenth embodiment of an implant 1500, which is similar to implant 1400 shown in FIGS. 16A-16C, but this implant 1500 may be particularly suitable for an anterior cervical procedure. As shown in FIG. 17C, the frame 1550 may be substantially in the form of a ring or loop of material with a central opening. When combined with the endplates 1512, which may be shaped and configured to match the central opening in the frame 1550, the opening may provide for a graft opening area 1516 configured to provide the maximum amount of volume for bone graft packing. The frame 1550 may include a front portion 1565 having an upper surface 1562 and a lower surface 1564. A first arm 1554 may extend from a first end of the frame 1550 and a second arm 1554 may extend from a second end of the frame 1550. The arms 1554 may join together to form the ring-like structure at a rear portion 1555.

One or more endplates 1512 are positioned on and affixed to the frame 1550 such that at least a portion of the ring portion of the frame 1550 is covered or housed within the endplates 1512. As shown in FIG. 17C, the endplates 1512 may have L-shaped configurations designed to follow the shape of the ring of the frame 1550. As shown, two endplates 1512 are affixed to the arms 1554 of the frame 1550 with the rear portion 1555 separating the endplates 1512. The endplates 1512 include a recess or channel 1523 designed and configured to retain at least a portion of the ring and, in particular, the arms 1554 of the frame 1550. In addition, a secondary opening or recess 1524 may be defined within at least one end of each of the endplates 1512 such that corresponding posts 1559 extending from the arms 1554 may be received in the recesses 1524 to aid in securing the endplates 1512 to the frame 1550. The endplates 1512 may also be secured to the frame 1550 with one or more pins 1578. Any suitable number, type, and location for the posts 1559 and pins 1578 may be selected to secure the endplate 1512.

The endplates 1512 may also define at least one recess, projection, etc. sized and dimensioned to retain a corresponding feature of at least a portion of the frame 1550, for example, to form a stepped joint 1526. A portion of the frame 1550 may be stepped with a male projection to mate with a stepped female configuration of the endplate 1512 or vice versa. The endplates 1512 each include superior and inferior surfaces 1542, 1544 having a contact area 1522 configured to contact and engage adjacent vertebrae (not shown). The contact area 1522 may include a plurality of protrusions 1513 or teeth, for example, which may be pyramidal in shape.

In this embodiment, the frame 1550 provides two fastener apertures 1534 to secure fasteners, such as bone screws therethrough. The upper surface 1562 and/or lower surface 1564 of the frame 1550 may extend a distance beyond the superior and/or inferior surfaces 1542, 1544 of the endplates 1512, for example, in the form of an eyebrow 1560. The upper surface 1562 and/or lower surface 1564 of the frame 1550 may further include one or more torsional stabilizers 1570 configured to prevent or minimize torsional motion of the implant 1500 once implanted. The torsional stabilizers 1570 may act as extensions or fins, which may serve as knife edges to further purchase into the bone of the adjacent vertebrae or serve as a stop to abut anterior aspects of the adjacent vertebrae.

In addition, one or more locking mechanisms 1520 may be provided to block or unblock the heads of the screws when positioned within the respective fastener apertures 1534. The anti-back out mechanism 1520 may include set screws configured to block a portion of the screw or screws positioned through the frame 1550.

Figure 18A:
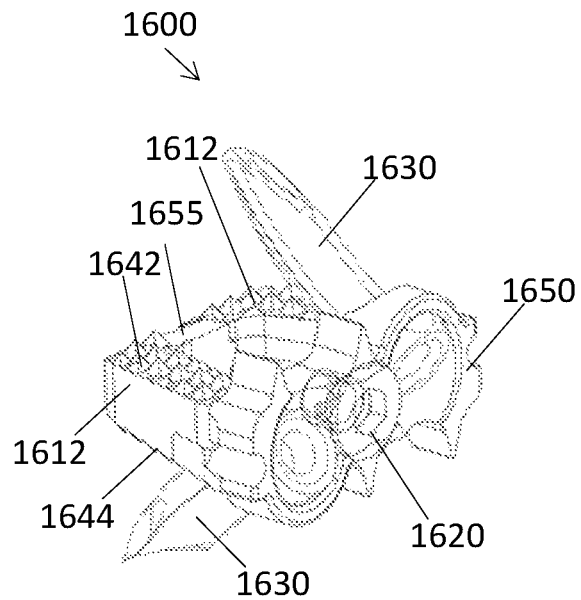
FIG. 18A is a perspective view of an eighteenth embodiment of a frame with endplates where the implant is secured to adjacent vertebrae utilizing anchors instead of screws.
Figure 18B:
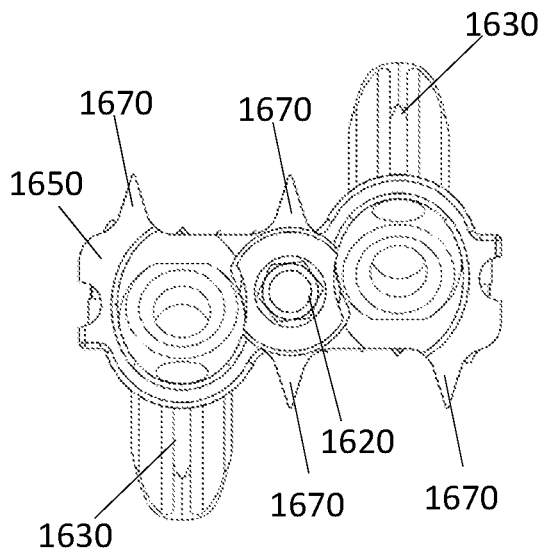
FIG. 18B is a front view of the embodiment shown in FIG. 18A.
Figure 18C:
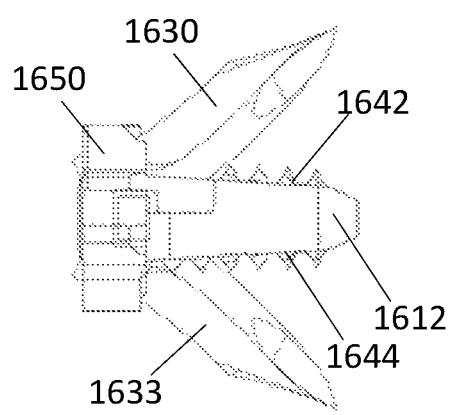
FIG. 18C is a side view of the embodiment shown in FIG. 18A.
Figure 18D:
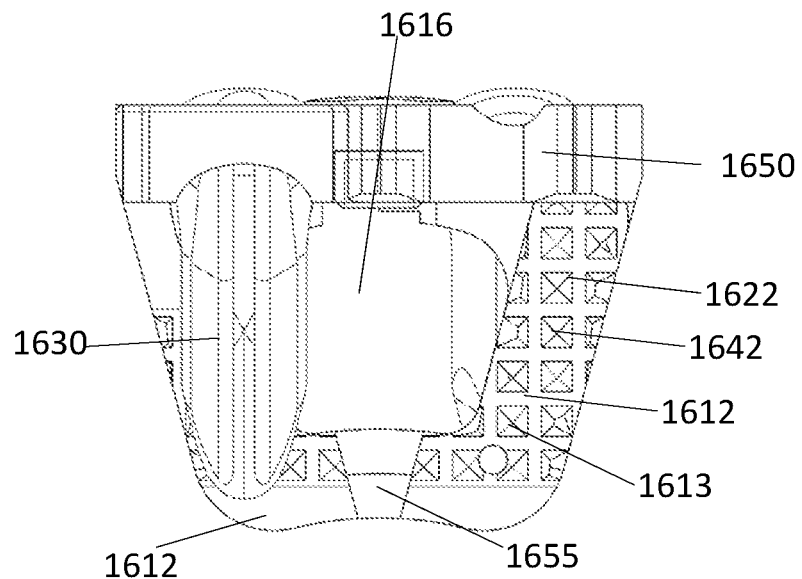
FIG. 18D is a top view of the embodiment shown in FIG. 18A.
Figure 18E:
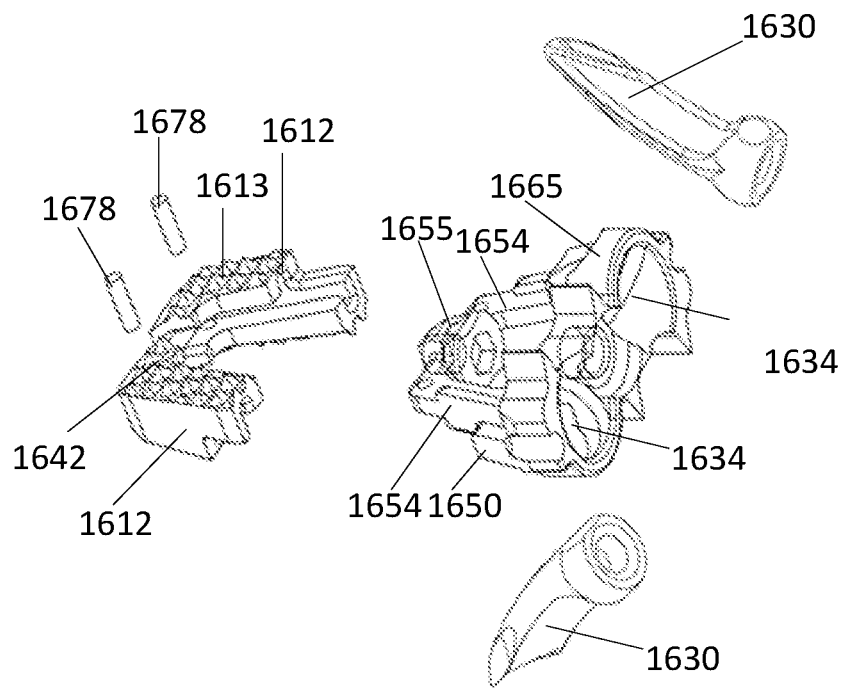
FIG. 18E is an exploded view of the embodiment shown in FIG. 18A.

FIGS. 18A-18E depict a sixteenth embodiment of an implant 1600. In general, most of the structure of implant 1600 is similar or comparable to the structure of implant 1500 discussed above. As shown in FIG. 18E, the frame 1650 may be substantially in the form of a ring or loop of material with a central opening. The frame 1650 includes front portion 1665 and arms 1654 extending from first and second ends of the front portion 1665. The arms 1654 join together at the rear portion 1655 to form the ring-like structure. The endplates 1612 are positioned on and affixed to the frame 1650 such that at least a portion of the ring portion of the frame 1650 is covered or housed within the endplates 1612. The endplates 1612 are affixed to the arms 1654 of the frame 1650 with the rear portion 1655 separating the endplates 1612. In this instance, the rear portion 1655 includes angled lateral sides designed to mate with corresponding faces on the ends of the endplates 1612.

In this embodiment, anchors 1630 have been substituted for the screws. While bone screws provide strength, in some situations, it may desirable to use a shim or anchor 1630, as such fasteners can be easily inserted. The bone screw may be screwed into bone (e.g., using a driver), while the anchor 1630 can be hammered into place. In addition, a combination of screws and anchors may be selected to maximize speed of implantation and attachment to the adjacent vertebrae. As discussed herein and throughout, any of the fasteners may include any suitable fasteners known in the art and may be substituted for one another as appropriate.

When used, the anchors 1630 may include a substantially flat or thin piece of material extending along a longitudinal axis. The anchors 1630 can be curved and/or angled along the longitudinal axis, for example. The anchors 1630 may have any suitable length and width. The anchors 1630 may include a head portion which is rounded or substantially flattened at its proximal most end. The flattened head portion may allow for greater contact area with an insertion instrument, for example, when the anchor 1630 is hammered into place. The anchors 1630 may include a rounded or pointed tip at the distal most end. The anchors 1630 may or may not contain an extension or spline. The spline may have the greatest height at the head portion and taper to the smallest height proximate to the distal most end of the anchor 1630. On the other hand, bone screws may include a threaded shaft and a head portion, which may be rounded, for example. The screws may include any suitable screws known in the art including fixed or variable angle of any suitable size with appropriate thread spacing, thread pitch, head design, length, and the like.

The screws and/or anchors 1630 enter the fastener apertures 1634 in the frame 1650 at specified angles to enter each of the adjacent vertebrae at the optimal locations. In particular, the anchors 1630 may be inserted at an angle for maximum screw purchase into the superior and/or inferior vertebral bodies. As shown in FIG. 18B, two anchors 1630 may be used to secure the superior and inferior vertebral bodies, respectively (not shown). In other embodiments, the device can include different numbers, types, and variations of bone screws and/or anchors.

The other features discussed for the embodiment shown in FIGS. 17A-17C for implant 1500 are substantially the same for implant 1600 including contact areas 1622 on the superior and inferior surfaces 1642, 1644, the protrusions 1613, graft opening 1616, torsional stabilizers 1670, fastener apertures 1634, and locking or anti-back out mechanisms 1620.

Figure 19A:
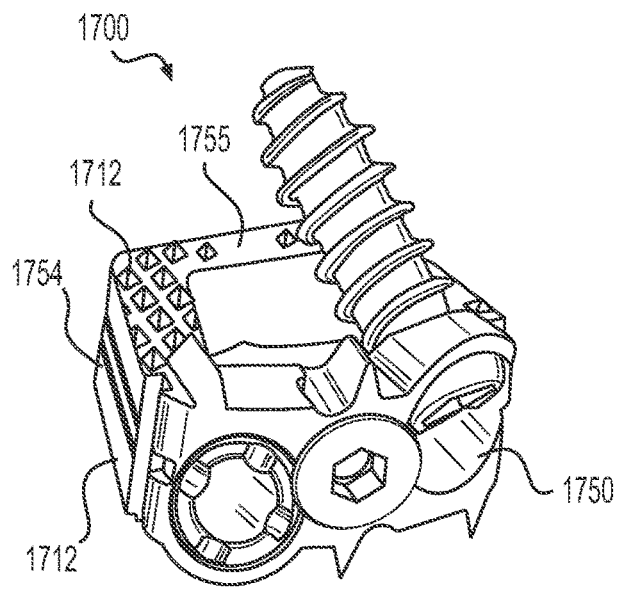
FIG. 19A is a perspective view of a nineteenth embodiment of a frame with multiple endplates suitable for use in cervical applications.
Figure 19B:
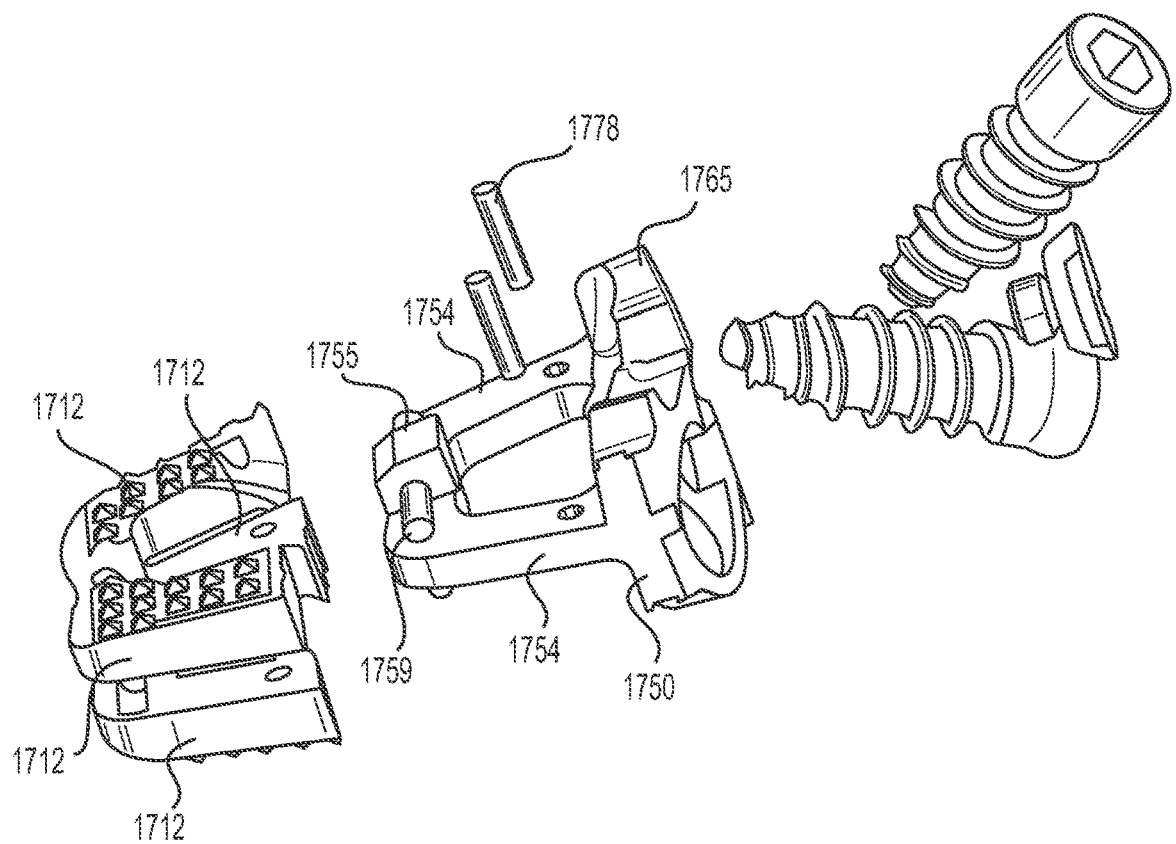
FIG. 19B is an exploded view of the embodiment shown in FIG. 19A.

FIGS. 19A and 19B depict a seventeenth embodiment of an implant 1700. In general, most of the structure of implant 1700 is similar or comparable to the structure of implant 1500 discussed above. Although not identified by number, the other features discussed for the embodiment shown in FIGS. 17A-17C for implant 1500 are substantially the same for implant 1700. Instead of endplates which surround the frame and being positioned on either side of the rear portion of the frame, separate top and bottom endplates 1712 are positioned on both sides of the rear portion 1755 of the frame 1750 for implant 1700. In this embodiment, a lateral portion of each of the arms 1754 is exposed and contiguous with a lateral portion of the endplates 1712.

As shown in FIG. 19B, the frame 1750 may be substantially in the form of a ring or loop of material with a central opening. The frame 1750 includes front portion 1765 and arms 1754 extending from first and second ends of the front portion 1765. The arms 1754 join together at the rear portion 1755 to form the ring-like structure. In this embodiment, instead of posts as shown in implant 1500, the arms 1754 may also include protrusions 1759 designed to secure the endplates 1712. The protrusions 1759 may be configured and dimensioned to fit in corresponding recesses formed in the interior surfaces of the endplates 1712. The protrusions 1759 may extend superiorly and/or inferiorly from each of the arms 1754. The protrusions 1759 may be positioned proximate to and extending substantially perpendicularly from the rear portion 1755. Although the protrusions 1759 are rounded or semi-cylindrical in this embodiment, it is envisioned that any suitable shape, size, and number of protrusions 1759 may be selected to aid in securing the endplates 1712 to the frame 1750. In addition, one or more pins 1778 may be provided, to also secure the endplates 1712.

A plurality of endplates 1712 are positioned on and affixed to the frame 1750. The endplates 1712 may cover at least the superior and inferior surfaces of each of the arms 1754. In this embodiment, four endplates 1712 are provided: two endplates 1712 form the top of the implant 1700 and two endplates 1712 form the bottom of the implant 1700. The endplates 1712 are affixed to the arms 1754 of the frame 1750 with the rear portion 1755 separating the endplates 1712. A lateral portion of each of the arms 1754 may be exposed and contiguous with a lateral portion of the endplates 1712.

Figure 20A:
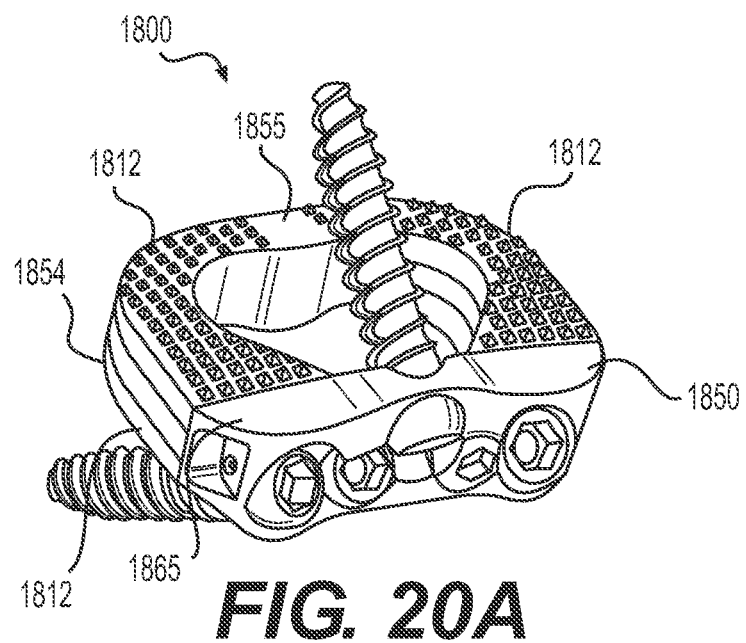
FIG. 20A is a perspective view of a twentieth embodiment of a frame with multiple endplates suitable for use in anterior lumbar procedures.
Figure 20B:
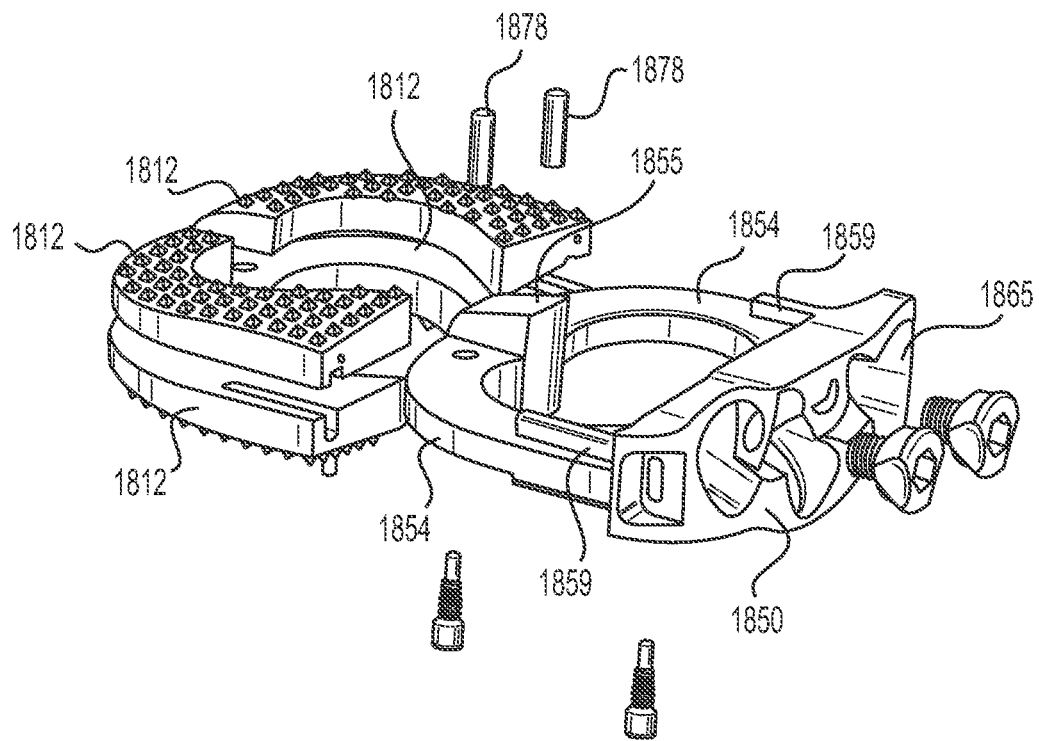
FIG. 20B is an exploded view of the embodiment shown in FIG. 20A.

According to an eighteenth embodiment, FIGS. 20A and 20B depict an implant 1800 substantially similar or comparable to the structure of implant 1400 discussed above. Although not identified by number, the other features discussed for the embodiment shown in FIGS. 16A-16C for implant 1400 are substantially the same for implant 1800. Instead of endplates which surround the frame and being positioned on either side of the rear portion of the frame, separate top and bottom endplates 1812 sandwich the arms 1854 and are positioned on both sides of the rear portion 1855 of the frame 1850 for implant 1800. In this embodiment, a lateral portion of each of the arms 1854 is exposed and contiguous with a lateral portion of the endplates 1812.

As shown in FIG. 20B, the frame 1850 may be substantially in the form of a ring or loop including front portion 1865 and arms 1854 extending substantially orthogonally from first and second ends of the front portion 1865. The arms 1854 join together at the rear portion 1855 to form the ring-like structure. In this embodiment, instead of posts as shown in implant 1400, the arms 1854 may also include protrusions 1859 (similar to the protrusion in implant 1700) designed to secure the endplates 1812. The protrusions 1859 may be configured and dimensioned to fit in corresponding recesses formed in the interior surfaces of the endplates 1812. The protrusions 1859 may extend superiorly and/or inferiorly from each of the arms 1854.

In this embodiment, the protrusions 1859 may be positioned proximate to and extending substantially perpendicularly from the front portion 1865 of the frame 1850. Although the protrusions 1859 are rounded or semi-cylindrical in this embodiment, it is envisioned that any suitable shape, size, and number of protrusions 1859 may be selected to aid in securing the endplates 1812 to the frame 1850. In addition, one or more pins 1878 may be provided, to also secure the endplates 1812. A corresponding opening or recess may be provided in the endplates 1812 sized and dimensioned to receive the pins 1878. Here, the pins 1878 are provided on either side of the rear portion 1855 of the frame 1850. Although the protrusions 1859 and pins 1878 are provided in certain positions and on the respective arms 1854 and endplates 1812, it is contemplated that the location of the protrusions 1859 and pins 1878 may be moved or switched as appropriate.

The endplates 1812 are positioned on and affixed to the frame 1850, for example, such that the endplates 1812 cover at least the superior and inferior surfaces of each of the arms 1854. In this embodiment, four endplates 1812 are provided: two endplates 1812 form the top of the implant 1800 and two endplates 1812 form the bottom of the implant 1800. The endplates 1812 are affixed to the arms 1854 of the frame 1850 with the rear portion 1855 separating the endplates 1812 on each of the top and bottom portions. A lateral portion of each of the arms 1854 may be exposed and contiguous with a lateral portion of the endplates 1812.

According to a nineteenth embodiment, FIGS. 21A-21D depict an implant 1900 substantially similar or comparable to the structure of implants 1500 and 1700 discussed above. Although not identified by number, the other features discussed for the embodiments shown in FIGS. 17A-17C and FIGS. 19A and 19B, respective, for implants 1500 and 1700 are substantially the same for implant 1900. Instead of multiple endplates which surrounds the frame, a single unitary piece forming the endplate 1912 surrounds the frame 1950 for implant 1900. In this embodiment, the arms 1954 are completely surrounded and housed within the unitary endplate 1912.

Figure 21A:
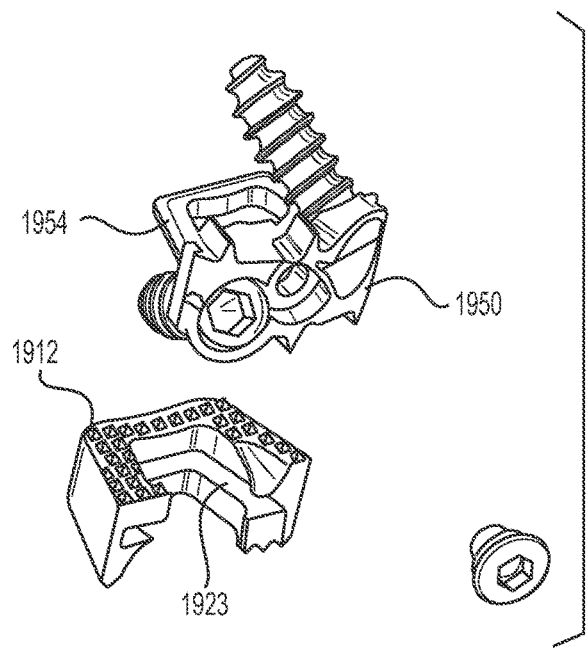
FIG. 21A is an exploded view of a twenty-first embodiment of a frame with a single endplate suitable for use in cervical procedures.
Figure 21B:
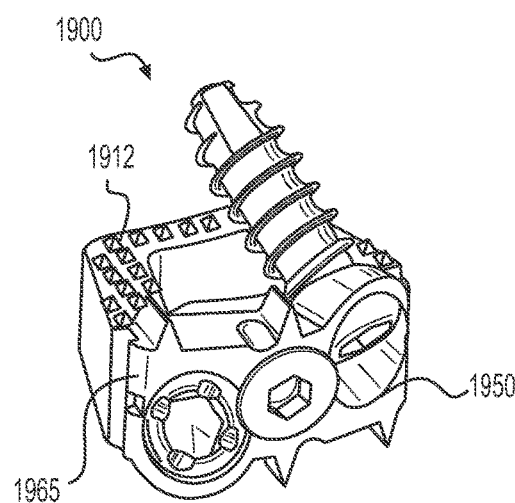
FIG. 21B is a perspective view of the embodiment shown in FIG. 21A.
Figure 21C:
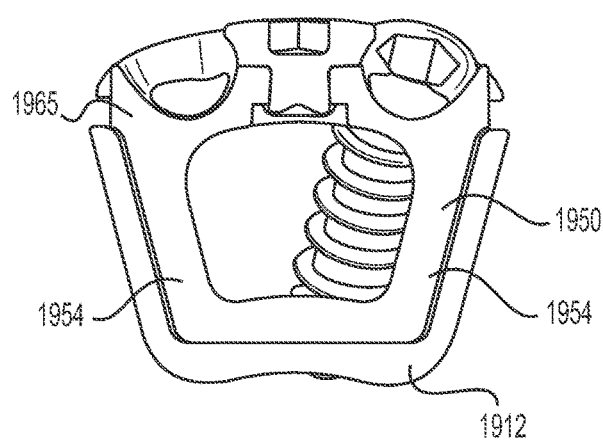
FIG. 21C is a cross sectional top view of the embodiment shown in FIG. 21B.
Figure 21D:
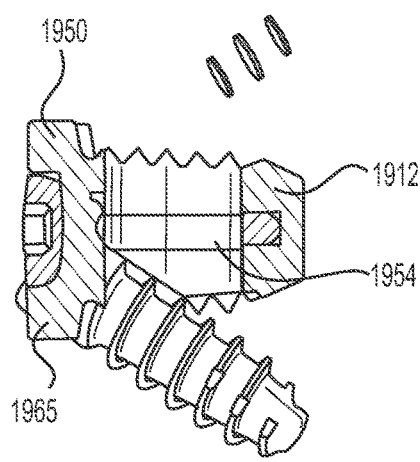
FIG. 21D is a cross sectional side view of the embodiment shown in FIG. 21B.

As shown in FIGS. 21A and 21C, the frame 1950 may be substantially in the form of a ring or loop, which includes front portion 1965 and arms 1954 extending from first and second ends of the front portion 1965. The arms 1954 join together to form a continuous ring having a single height dimension, and unlike, other embodiments described herein, lacks a raised rear portion. Thus, there is no separation or gap in the endplates. The endplate 1912 includes a recess or channel 1923 designed and configured to retain at least a portion of the ring and, in particular, the arms 1954 of the frame 1950. One or more pins (not shown) may be provided to secure the endplate 1912 to the frame 1950.

According to a twentieth embodiment, FIGS. 22A-22D depict an implant 2000 substantially similar or comparable to the structure of implants 1300, 1400 and 1800 discussed above. Although not identified by number, the other features discussed for the embodiments shown in FIGS. 15A-15B, FIGS. 16A-16C and FIGS. 20A-20B, respectively, for implants 11300, 1400 and 1800 are substantially the same for implant 2000. Instead of multiple endplates which surrounds the frame, a single unitary piece forming the entire endplate 2012 surrounds the frame 2050 for implant 2000. In this embodiment, the arms 2054 are completely surrounded and housed within the unitary endplate 2012.

Figure 22A:
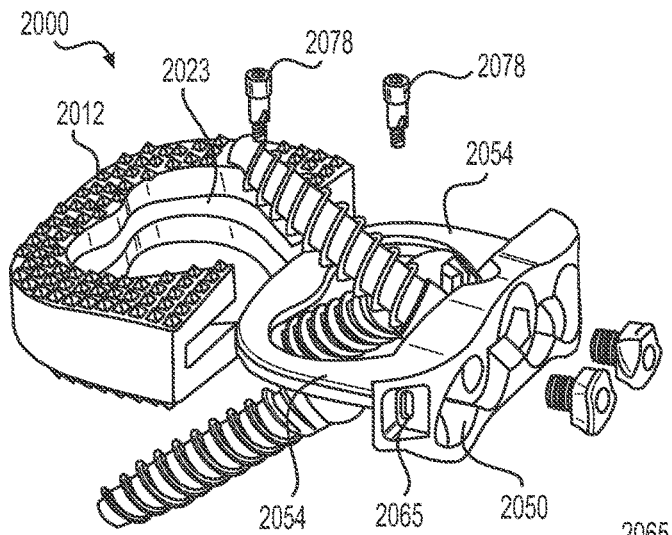
FIG. 22A is an exploded view of a twenty-second embodiment of a frame with a single endplate suitable for use in anterior lumbar applications.
Figure 22B:
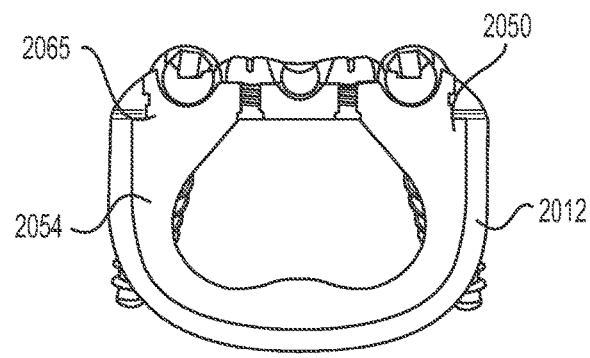
FIG. 22B is a cross sectional top view of the embodiment shown in FIG. 22A when assembled.
Figure 22C:
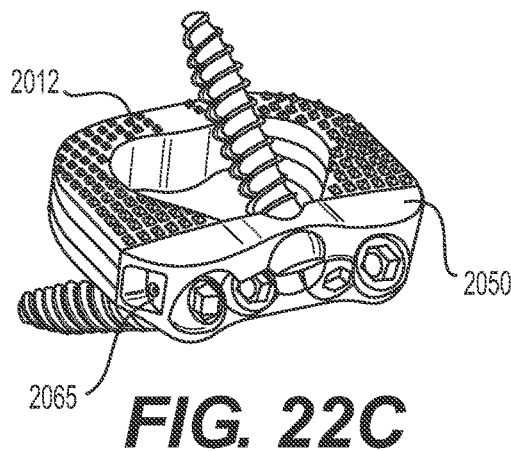
FIG. 22C is a perspective view of the embodiment shown in FIG. 22A when assembled.
Figure 22D:
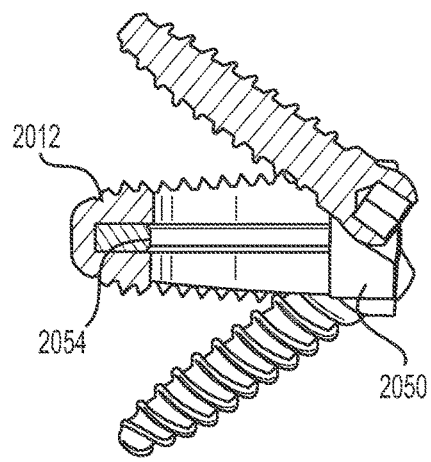
FIG. 22D is a cross sectional side view of the embodiment shown in FIG. 22C.

As shown in FIGS. 22A and 22B, the frame 2050 may be substantially in the form of a ring or loop, which includes front portion 2065 and arms 2054 extending from first and second ends of the front portion 2065. The arms 2054 join together to form a continuous ring having a single height dimension, and unlike, other embodiments described herein, lacks a raised rear portion. Thus, there is no separation or gap in the endplates. The endplate 2012 includes a recess or channel 2023 designed and configured to retain at least a portion of the ring and, in particular, the arms 2054 of the frame 2050. One or more pins 2078 may be provided to secure the endplate 2012 to the frame 2050.

FIGS. 23A-23D depict a twenty-first embodiment of an implant 2100, which is substantially similar or comparable to the structure of implants 1500 and 1700 discussed above. Although not identified by number, the other features discussed for the embodiments shown in FIGS. 17A-17C and FIGS. 19A and 19B, respective, for implants 1500 and 1700 are substantially the same for implant 1900. Instead of separating the endplates with the raised rear portion, separate top and bottom endplates 2112 are provided which form at least a portion of the top and bottom portions of the implant 2100, respectively.

Figure 23A:
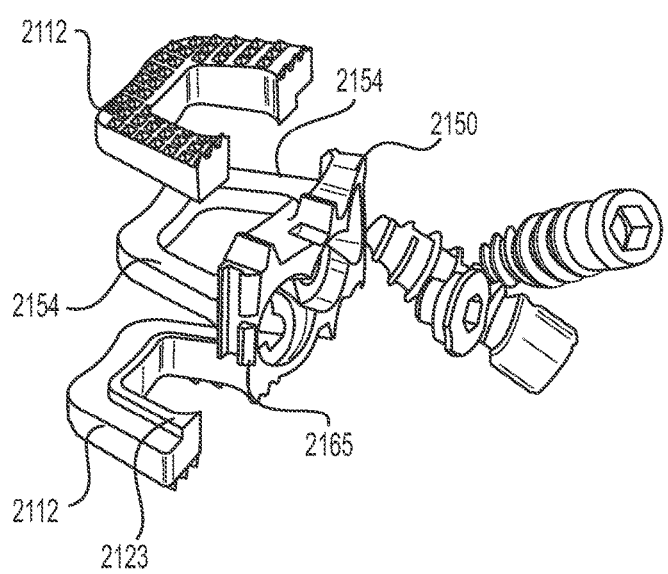
FIG. 23A is an exploded view of a twenty-third embodiment of a frame with top and bottom endplates suitable for use in a cervical application.
Figure 23B:
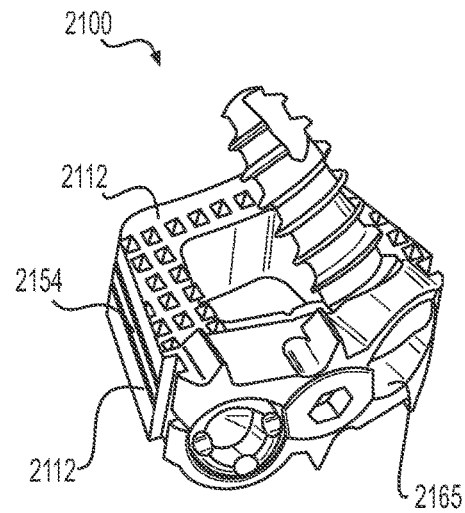
FIG. 23B is a perspective view of the embodiment shown in FIG. 23A when assembled.
Figure 23C:
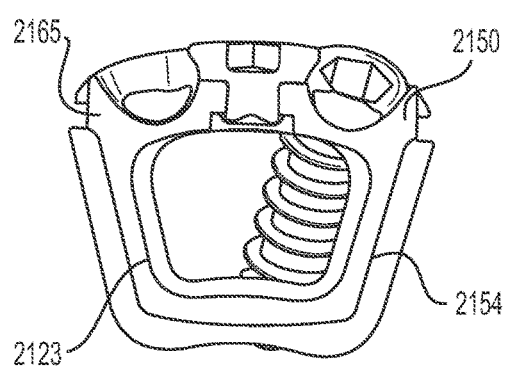
FIG. 23C is a cross sectional top view of the embodiment shown in FIG. 23B.
Figure 23D:
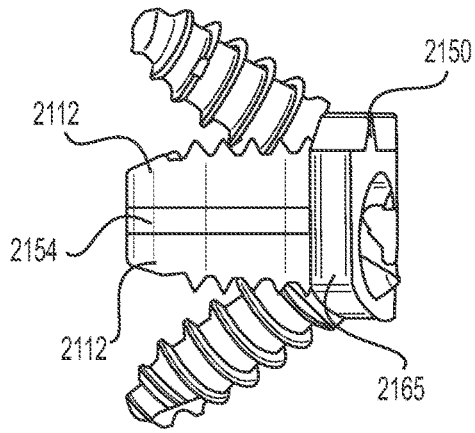
FIG. 23D is a side view of the embodiment shown in FIG. 23B.

As shown in FIGS. 23A and 23C, the frame 2150 may be substantially in the form of a ring or loop, which includes front portion 2165 and arms 2154 extending substantially perpendicularly from a rear face of the first and second ends of the front portion 2165. The arms 2154 join together to form a continuous ring having a single height dimension, and unlike, other embodiments described herein, lacks a raised rear portion. Thus, there is no separation or gap in the endplates based on the raised rear portion. There is a separation between the endplates 2112, however, due to the thickness of the arms 2154. The top and bottom endplates 2112 each include a raised lip 2123 designed and configured to retain at least a portion of the ring and, in particular, the arms 2154 of the frame 2150. The raised lip 2123 has a height greater than the interior surface of the endplate 2112, which at least partially surrounds a perimeter of an inner surface of the endplate 2112. Although the raised lip 2123 is only visible on the bottom endplate 2112, the top endplate 2112 may have a similar and corresponding lip 2123. One or more pins (not shown) may be provided to secure the top and bottom endplates 2112 to the frame 2150.

FIGS. 24A-24D depict a twenty-second embodiment of an implant 2200, which is substantially similar or comparable to the structure of implants 1500 and 1700 discussed above. Although not identified by number, the other features discussed for the embodiments shown in FIGS. 17A-17C and FIGS. 19A and 19B, respective, for implants 1500 and 1700 are substantially the same for implant 2200. Instead of separating the endplates with the raised rear portion, separate top and bottom endplates 2212 are provided which form at least a portion of the top and bottom portions of the implant 2200, respectively.

Figure 24A:
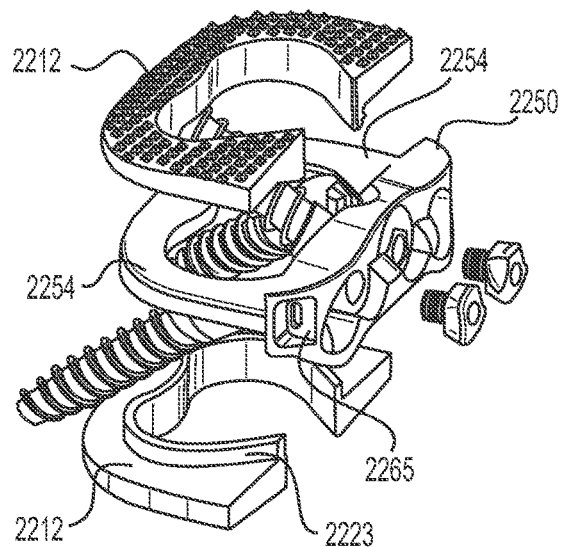
FIG. 24A is an exploded view of a twenty-fourth embodiment of a frame with top and bottom endplates suitable for use in an anterior lumbar application.
Figure 24B:
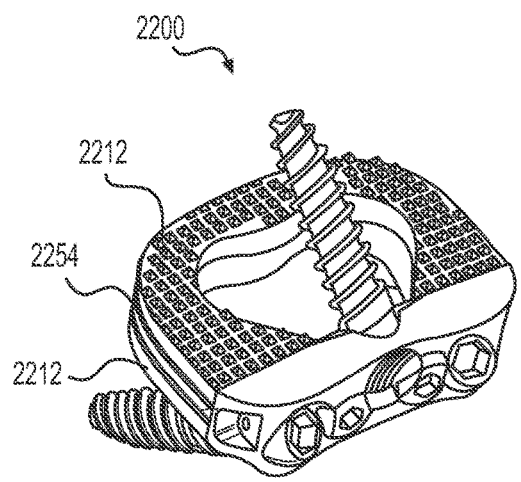
FIG. 24B is a perspective view of the embodiment shown in FIG. 24A when assembled.
Figure 24C:
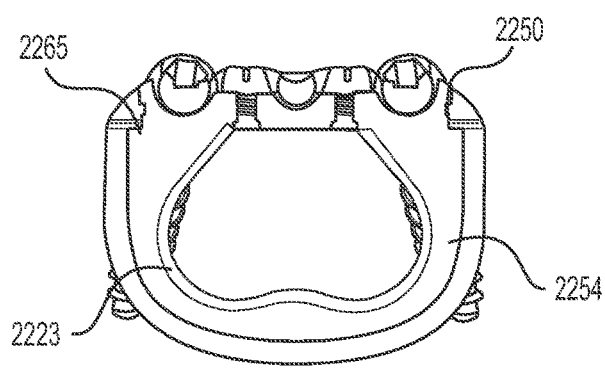
FIG. 24C is a cross sectional top view of the embodiment shown in FIG. 24B.
Figure 24D:
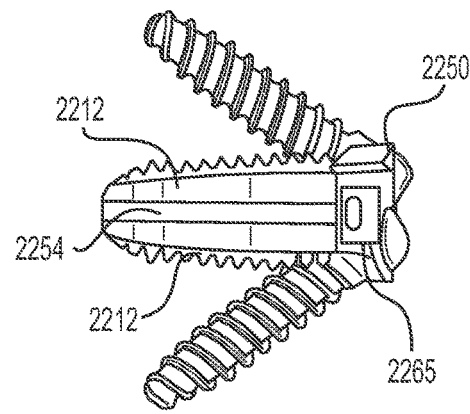
FIG. 24D is a side view of the embodiment shown in FIG. 24B.

As shown in FIGS. 24A and 24C, the frame 2250 may be substantially in the form of a ring or loop, which includes front portion 2265 and arms 2254 extending substantially perpendicularly from a rear face of the first and second ends of the front portion 2265. The arms 2254 join together to form a continuous ring having a single height dimension, and unlike, other embodiments described herein, lacks a raised rear portion. Thus, there is no separation or gap in the endplates based on the raised rear portion. There is a separation between the endplates 2212, however, due to the thickness of the arms 2254. The top and bottom endplates 2212 each include a raised lip 2223, which at least partially surrounds a perimeter of an inner surface of the endplate 2112 and mimics the central openings. The raised lip 2223 has a height greater than the interior surface of the endplate 2212, and is designed and configured to retain at least a portion of the ring and, in particular, the arms 2254 of the frame 2250. Although the raised lip 2223 is only visible on the bottom endplate 2212, the top endplate may have a similar and corresponding lip 2223 projecting from the interior surface which contacts the arm 2254. One or more pins (not shown) may be provided to secure the top and bottom endplates 2212 to the frame 2250.

The inserts, members, frames, spacers, and endplates described in this document may be comprised of any suitable materials. The spacers or endplates can be comprised of any material that is conducive to the enhancement of fusion between the two adjacent vertebrae. In one particular embodiment, the spacer or endplate is made of a biocompatible plastic, like polyether ether ketone (PEEK), polyetherketoneketone (PEKK), ultra-high molecular weight (UHMW) polyethylene, or other polymers and plastics known in the art which are physiologically compatible. Any other materials that are physiologically compatible may also be used such as bone or metal. The inserts, members, or frames can also be comprised of any physiologically compatible materials. In the preferred embodiment, the inserts, members, or frames are composed of a biocompatible metal, such as stainless steel, titanium, titanium alloys, surgical steel, and metal alloys, for example. Preferably, the inserts, members, or frames are formed from titanium or a titanium alloy. Any other materials that are physiologically compatible may also be used such as bone or plastic.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. An intervertebral implant for implantation in an intervertebral space between adjacent vertebrae, the implant comprising:
    a frame having a front portion and a plurality of arms extending from the front portion, the front portion at least partially defining a fastener aperture sized and dimensioned for receiving a fastener; and
    at least one endplate including at least one outer surface having a contact area configured to engage adjacent vertebrae, the at least one endplate being affixed to the frame such that the at least one endplate contacts at least a portion of the plurality of arms,
    wherein the frame includes at least one projection extending along a length of the plurality of arms and the at least one endplate defines at least one recess sized and configured to receive the at least one projection,
    wherein the frame includes a raised rear portion.

2. The implant of claim 1, wherein the front portion has a first height and the plurality of arms have a second height that is less than the first height.

3. The implant of claim 1, wherein the at least one endplate includes a plurality of endplates configured to be separated a lateral distance due to the raised rear portion.

4. The implant of claim 3, wherein the raised rear portion is substantially flush with the outer surface of the at least one endplate.

5. The implant of claim 1, wherein the at least one endplate includes a plurality of endplates configured to be separated a vertical distance due to a thickness of the plurality of arms.

6. The implant of claim 1, wherein the at least one endplate defines at least one channel extending along an inner perimeter sized and configured to receive at least a portion of the plurality of arms.

7. The implant of claim 1, wherein the at least one projection is a post extending outwardly from the plurality of arms and the at least one endplate includes at least one opening sized and configured to receive the at least one post.

8. The implant of claim 1, wherein the at least one endplate extends from an upper surface to a lower surface and completely surrounds at least one of the plurality of arms.

9. The implant of claim 1, wherein the front portion comprises a front surface and at least one eyebrow, wherein the eyebrow projects past a superior surface, an inferior surface, or both surfaces of the at least one endplate, and the fastener aperture for receiving the fastener traverses the front surface of the frame at an angle divergent to a horizontal plane.

10. The implant of claim 1, wherein the fastener is an anchor and/or a bone screw.

11. The implant of claim 1, wherein the plurality of arms join together to form the ring-like structure having a central opening.

12. The implant of claim 1, wherein the at least one endplate does not cover the front portion of the frame.

13. A stand-alone implant for implantation in a treated area of an intervertebral space between vertebral bodies of a spine, the implant comprising:
    a frame including a front portion having a first end and a second end, a first arm extending orthogonally from the first end of the front portion, and a second arm extending orthogonally from the second end of the front portion, wherein the first and second arms join together at a rear portion to form a continuous ring-like body, and at least one hole traversing the front portion for receiving a fastener; and
    at least one endplate secured to the frame such that the at least one endplate rests on at least one of the first and second arms, the at least one endplate forming a superior surface, an inferior surface, or both surfaces to form a contact area configured to engage adjacent vertebrae,
    wherein the first arm and the second arm include a first protrusion and a second protusion that is configured and dimensioned to fit into a first recess and a second recess formed in an interior surface of at least one endplate,
    wherein the frame includes a raised rear portion.

14. The implant of claim 13, wherein the implant defines an opening extending from the superior surface to the inferior surface of the implant configured to receive bone graft material.

15. The implant of claim 13, wherein the at least one endplate includes a plurality of endplates configured to be separated a lateral distance due to the raised rear portion.

16. The implant of claim 13, wherein the at least one endplate defines at least one channel extending along an inner perimeter sized and configured to receive at least a portion of the plurality of arms.

17. The implant of claim 13, wherein the frame includes at least one post extending outwardly from the plurality of arms and the at least one endplate includes at least one opening sized and configured to receive the at least one post.

18. An intervertebral implant for implantation in an intervertebral space between adjacent vertebrae, the implant comprising:
- a frame having a front portion and a plurality of arms extending from the front portion and joined together to form a ring-like structure, the front portion at least partially defining a fastener aperture sized and dimensioned for receiving a fastener; and
- at least one endplate including at least one outer surface having a contact area configured to engage adjacent vertebrae, the at least one endplate being affixed to the frame such that the at least one endplate contacts at least a portion of the plurality arms,
- wherein the endplate defines at least one channel extending along an inner perimeter sized and configured to receive at least a portion of the plurality of arms,
- wherein the plurality of arms includes projections connecting the plurality of arms and the at least one endplate,
- wherein the frame includes a raised rear portion that is flush with a surface of the at least one endplate.

* * * * *